(12) United States Patent
Kawai et al.

(10) Patent No.: US 7,468,529 B2
(45) Date of Patent: Dec. 23, 2008

(54) POROUS UV-EMITTING SEMICONDUCTOR ON POROUS SUBSTRATE AS STERILIZING FILTER MADE BY FILTERING SUSPENDED SEMICONDUCTOR PARTICLES

(75) Inventors: Chihiro Kawai, Itami (JP); Masami Tatsumi, Itami (JP)

(73) Assignee: Sumitomo Electric Industries, Ltd., Osaka (JP)

(*) Notice: Subject to any disclaimer, the term of this patent is extended or adjusted under 35 U.S.C. 154(b) by 244 days.

(21) Appl. No.: 10/500,975

(22) PCT Filed: Jul. 10, 2003

(86) PCT No.: PCT/JP03/08777

§ 371 (c)(1),
(2), (4) Date: Jul. 8, 2004

(87) PCT Pub. No.: WO2004/006969

PCT Pub. Date: Jan. 22, 2004

(65) Prior Publication Data

US 2005/0042743 A1 Feb. 24, 2005

(30) Foreign Application Priority Data

| Oct. 4, 2002 | (JP) | ................. | 2002-292533 |
| Nov. 5, 2002 | (JP) | ................. | 2002-321351 |
| Nov. 7, 2002 | (JP) | ................. | 2002-202837 |
| Mar. 28, 2003 | (JP) | ................. | 2003-090727 |
| May 26, 2003 | (JP) | ................. | 2003-148029 |

(51) Int. Cl.
*H01L 33/00* (2006.01)
*H01L 21/208* (2006.01)

(52) U.S. Cl. ............ 257/102; 422/186.3; 257/E33.018; 438/38

(58) Field of Classification Search ............. 422/186.3, 422/186; 257/102, E33.018, 81, E31.013; 438/38; 137/140; 210/510.1
See application file for complete search history.

(56) References Cited

U.S. PATENT DOCUMENTS 4,801,380 A * 1/1989 Parker et al. ........... 210/500.21

(Continued)

FOREIGN PATENT DOCUMENTS

EP 0 653 392 A1 5/1995

(Continued)

OTHER PUBLICATIONS

"Ultraviolet", The American Heritage Stedman's Medical Dictionary (2002) Retrieved Aug. 2, 2006, from xreferplus. http://www.xreferplus.com/entry/2800329.*

(Continued)

*Primary Examiner*—Lynne Gurley
*Assistant Examiner*—Andrew O. Arena
(74) *Attorney, Agent, or Firm*—McDermott Will & Emery LLP

(57) ABSTRACT

A filter for trapping, sterilizing, and decomposing organic matter, bacteria, viruses, and other harmful substances is provided at low cost and extremely high efficiency. A semiconductor material having a light emitting function is formed in the interior or on the surface of a porous ceramic material substrate by deposition from a suspension of semiconductor particles, and an electrode provided to serve as a filter. Voltage is applied so that ultraviolet light is emitted while a fluid is being filtered, and any harmful substances are filtered and simultaneously sterilized and decomposed.

32 Claims, 28 Drawing Sheets

U.S. PATENT DOCUMENTS

| | | | | |
|---|---|---|---|---|
| 4,959,142 | A | * | 9/1990 | Dempo .................. 210/167.29 |
| 4,963,750 | A | * | 10/1990 | Wilson ....................... 250/436 |
| 4,966,759 | A | * | 10/1990 | Robertson et al. ........... 422/186 |
| 5,266,215 | A | * | 11/1993 | Engelhard ................... 210/748 |
| 5,298,767 | A | * | 3/1994 | Shor et al. ..................... 257/77 |
| 5,331,180 | A | | 7/1994 | Yamada et al. |
| 5,569,932 | A | * | 10/1996 | Shor et al. ...................... 257/3 |
| 5,726,464 | A | * | 3/1998 | Kumomi et al. ............. 257/103 |
| 5,834,378 | A | * | 11/1998 | Kurtz et al. ................. 438/694 |
| 5,914,183 | A | * | 6/1999 | Canham .................. 428/312.6 |
| 5,939,732 | A | | 8/1999 | Kurtz et al. |
| 6,225,647 | B1 | * | 5/2001 | Kurtz et al. ................... 257/94 |
| 6,238,631 | B1 | * | 5/2001 | Ogata et al. ............... 422/186.3 |
| 2002/0074314 | A1 | * | 6/2002 | Bohn et al. .................... 216/56 |

FOREIGN PATENT DOCUMENTS

| | | |
|---|---|---|
| EP | 0 767 486 A2 | 4/1997 |
| JP | 2683452 | 11/1997 |
| JP | 2001-259434 A | 9/2001 |
| JP | 2002-75171 A | 3/2002 |
| JP | 2003-53195 A | 2/2003 |
| WO | WO 94/27929 | 12/1994 |
| WO | WO 00/03230 | 1/2000 |

OTHER PUBLICATIONS

N. Miura et al., "Electroluminescence of $ZnF_2$ Thin-Films Doped with Rare-Earth Ions", Japanese Journal of Applied Physics, vol. 31, Part 1, No. 1, Jan. 1992, pp. 51-59.

N. Miura et al., "Strong Ultraviolet-Emitting $ZnF_2$:Gd Thin Film Electroluminescent Device", Japanese Journal of Applied Physics, vol. 30, No. 10B, Oct. 1991, pp. L1815-L1816.

Supplementary European Search Report for Application No. EP 03 74 1323 dated Oct. 5, 2006.

* cited by examiner (a)

(b)

(c)

(a)

(b)

(a)

(b)

(a)

(b)

(a)

(b)

(c)

(d)

(e)

(a)

(b)

(a)

(b)

US 7,468,529 B2

POROUS UV-EMITTING SEMICONDUCTOR ON POROUS SUBSTRATE AS STERILIZING FILTER MADE BY FILTERING SUSPENDED SEMICONDUCTOR PARTICLES

TECHNICAL FIELD

This invention relates to a porous semiconductor, and more particularly to a porous semiconductor that has an ultraviolet light emitting function and is useful as a filter for trapping organic matter, bacteria, viruses, and other harmful substances, and for sterilizing and decomposing the trapped substances, and to a method for manufacturing this porous semiconductor. The present invention also relates to this porous semiconductor that has the function of emitting ultraviolet light of particularly high luminance, and to a method for manufacturing this porous semiconductor. Further, the present invention relates to a filter, a bioreactor, and an ultraviolet light source that make use of such a porous semiconductor. The present invention the present invention also relates to a porous semiconductor constituted by porous silicon nitride having the function of emitting ultraviolet light or visible light by electroluminescence, cathode luminescence, or photoluminescence.

BACKGROUND ART

Semiconductor materials and elements that emit light of a shorter wavelength have come to be required of semiconductor light emitting devices in recent years. In particular, elements with a large bandgap, that is, that emit ultraviolet light with a wavelength of roughly 400 nm or less, are expected to find use in a wide range of applications because they can be used as the light source of photocatalysts and can provide a sterilizing function.

GaN, AlN, ZnO, and diamond are among the known semiconductor materials that emit ultraviolet light. The bandgaps of these materials and the corresponding emission wavelengths are 3.39 eV and 366 nm for GaN, 6.2 eV and 200 nm for AlN, 3.35 eV and 370 nm for ZnO, and 5.47 eV and 227 nm for diamond. With an Al—Ga—N ternary semiconductor, the values can be varied between 3.3 and 6.2 eV and between 200 and 366 nm. The last few years have seen considerable applied research into light emitting diodes and laser diodes made from these semiconductors, as well as applied research into light receiving elements (photodiodes).

"Ultraviolet light" generally refers to electromagnetic waves with a wavelength of about 100 to 400 nm, and is classified by wavelength into UV-A (325 to 400 nm), UV-B (280 to 325 nm), and UV-C (100 to 280 nm). The portion of UV-C from 100 to 200 nm is called vacuum ultraviolet light. Radiation of 254 nm is known to have a powerful sterilizing action because it directly destroys the DNA of viruses, bacteria, and so forth, and is therefore used in UV lamps. Radiation of 180 to 254 nm is useful in water treatment, such as the cleaning of sewage. In addition, radiation of 333 to 364 nm is widely used for photolithography, and that of 200 to 400 nm for the curing of UV-setting resins. At present, these ultraviolet rays are mainly generated by mercury vapor lamps. The use of semiconductor light emitting diodes in place of mercury vapor lamps has recently been studied as a way to avoid using mercury, which is harmful to the environment, and some products have already seen practical use.

Meanwhile, an ultraviolet light source is also needed for photocatalysts whose main component is $TiO_2$ or the like. Photocatalysts are mainly composed of $TiO_2$ microparticles, and when irradiated with ultraviolet light, they generate oxygen radicals that react with and decompose the molecules that make up stains and organic matter. Photocatalysts have been used for sewage cleaning and air purification equipment, toxic gas decomposition apparatus, and so on. To obtain a photocatalytic action, the catalyst must be irradiated with ultraviolet light having an energy of at least 3.2 eV (equivalent to a wavelength of 388 nm or less), which is the bandgap of $TiO_2$ (anatase), and here again black lights and other such mercury vapor lamps have been used. And, semiconductor light emitting diodes have also been studied, with some being put to practical application. Photocatalysts that function with visible light have also been invented. With these, part of the $TiO_2$ in the material is doped with nitrogen, so that the material is excited by visible light of 400 to 500 nm and thereby exhibits a photocatalytic action. The effect, however, is weaker than that of a UV-excited type of photocatalyst.

To efficiently sterilize viruses and bacteria, as well as organic matter, these must first be trapped, and the trapped material must be collected together and then irradiated with ultraviolet light. The reason is that ultraviolet light attenuates in the air and in liquids. Particularly in the treatment of sewage and other liquids in which there is a large amount of suspended matter, the reach is extremely short, so UV irradiation is performed after the suspended matter has first been precipitated or filtered off with a filtration membrane. In gases, either a nitrogen atmosphere that has a low UV attenuation factor is used, or a mercury vapor lamp with high output is used to increase the reach. These methods are drive up the cost, however, which poses a serious obstacle to their practical application.

In recent years there has been an increasing need for filters to be ceramic filters that offer higher heat resistance, strength, and permeability. Such ceramic filters have been used, for example, in the fields of food and pharmaceuticals. Organic membranes used to be used in these fields, but ceramics offer heat resistance, pressure resistance, chemical resistance, and high separability not available with organic membranes, and are gradually supplanting organic membranes. Furthermore, porous membranes have been used, for example, as catalyst carriers or bioreactors for microbe cultivation carriers, and so on.

One of the various types of ceramic available, silicon nitride is a structural ceramic material that has high strength, toughness, thermal shock resistance, and chemical resistance, and is therefore extremely promising as a filter material. A filter consisting of porous $Si_3N_4$ has been invented, in which $Si_3N_4$ particles having a columnar structure are bonded together so as to form a three-dimensionally intertwined structure by means of a binder phase containing at least one of compound of rare earth element (which refers to scandium, yttrium, and lanthanide elements).

For example, in Japanese Patent No. 2,683,452, it is indicated that porous $Si_3N_4$ in which columnar $Si_3N_4$ crystal particles are randomly oriented via an oxide-based binder phase has high strength characteristics and exhibits high permeability when used as a filter. This porous $Si_3N_4$ is manufactured by the following process. An oxide of a rare earth element (used as a sintering auxiliary) and an $Si_3N_4$ powder are mixed in specific proportions and then molded and fired in an inert gas. "Rare earth element" refers to scandium, yttrium, and the elements with atomic numbers 57 to 71. When $Y_2O_3$ is used as an auxiliary, for instance, it is understood that columnar $Si_3N_4$ particles are grown and a porous structure is produced when the $Y_2O_3$ and the $SiO_2$ present at the surface of the raw material $Si_3N_4$ form a liquid phase at the firing temperature, in which part of the $Si_3N_4$ dissolves and is reprecipitated.

The above-mentioned $Si_3N_4$ filters are the same as ordinary filters in that their only function is to filter according to the pore size of the porous material. Specifically, particles of organic components, bacteria, viruses, and so forth that are smaller than the pores cannot be trapped by filtration. The only method available for trapping these and obtaining a clarified permeated liquid has been to make the pore size of the porous material smaller than these particles, bacteria, and viruses. When the pore size is decreased, however, the problem is that there is more pressure loss in the filtration process, and this greatly compromises the permeation performance. Another drawback is that if part of the porous material breaks apart and the pores become larger, bacteria and the like can become admixed into the permeated liquid.

In addition, the following problems were encountered with ultraviolet light emitting porous materials produced by the prior art discussed above.

Difficult Pore Control

Methods employed up to now for rendering porous a semiconductor having a wide bandgap were not easy because in every case controlling the pore size of the porous material entailed so many steps.

Low Strength

A ceramic that has been rendered porous by prior art has weak bonds between the particles, so its strength is inadequate.

Low Permeability

Permeability is low when a porous material comprising semi-bonded spherical particles is used as a filter.

Low Thermal Thermal Shock Resistance

Because strength is low, thermal shock resistance is also low.

DISCLOSURE OF THE INVENTION

The present invention was conceived in light of this situation, and it is an object thereof to provide a filter for trapping organic matter, bacteria, viruses, and other harmful substances, and for sterilizing and decomposing the trapped substances, efficiently and at low cost, to provide a porous semiconductor used in this filter, and to provide a method for manufacturing the same. It is another object of the present invention to provide a porous semiconductor having the function of emitting ultraviolet light of particularly high luminance, which is favorable for use as a filter, and a method with which this porous semiconductor can be manufactured easily, and a filter that makes use of this porous semiconductor. It is yet another object of the present invention to provide a porous semiconductor whose pore size is favorably controlled, and whose strength, permeability, and thermal shock resistance are all high.

The stated objects are achieved by the present invention as given below.

1. A porous semiconductor, comprising:
   a porous substrate having continuous pores; and
   a porous semiconductor layer having a light emitting function that works by electroluminescence, cathode luminescence, or photoluminescence, and having continuous pores.
2. A porous semiconductor according to 1, which emits ultraviolet light with a wavelength of 400 nm or less.
3. A porous semiconductor according to 2, wherein the ultraviolet light has a wavelength of 200 to 400 nm.
4. A porous semiconductor according to 3, wherein the ultraviolet light has a wavelength of 230 to 270 nm.
5. A porous semiconductor according to any of 1 to 4, wherein the semiconductor layer has a pn junction structure.
6. A porous semiconductor according to any of 1 to 5, wherein the porosity of the semiconductor layer is at least 30%.
7. A porous semiconductor according to any of 1 to 6, wherein an average pore size of the porous substrate and/or the porous semiconductor layer is from 0.0003 to 100 μm.
8. A porous semiconductor according to any of 1 to 7, wherein an insulating layer is formed on the front and/or back surface of the semiconductor layer.
9. A porous semiconductor according to any of 1 to 8, wherein the insulating layer is formed from a material having a photocatalytic function.
10. A porous semiconductor according to any of 1 to 9, wherein the semiconductor layer is made up of crystal particles, and a surface of these crystal particles is coated with particles having a photocatalytic function.
11. A filter composed of the porous semiconductor according to any of 1 to 10.
12. A filter according to 11, wherein the porous substrate is a porous ceramic or a metal having continuous pores, and a porous semiconductor layer is provided in the interior or on a surface of the substrate.
13. A filter according to 12, wherein a porosity of the porous substrate is at least 30%.
14. A filter according to 12 or 13, wherein a thickness of the porous semiconductor layer disposed on the surface of the porous substrate is from 1 to 1000 μm.
15. A filter according to any of 12 to 14, wherein an average pore size of the porous substrate is from 0.01 to 1000 μm.
16. A porous semiconductor according to any of 1 to 9, wherein the porous semiconductor layer is composed of numerous columns of semiconductor material erected on a surface of the porous substrate.
17. A porous semiconductor according to 16, wherein the pores in the porous substrate are through-holes perpendicular to a substrate plane.
18. A porous semiconductor according to 16 or 17, wherein an average pore size of the porous substrate is from 0.1 to 100 μm.
19. A porous semiconductor according to any of 16 to 18, wherein a pn junction is formed in a lengthwise direction of the columns.
20. A porous semiconductor according to any of 16 to 20, wherein the columns comprising a base component and a pointed component located on the distal end side of this base component.
21. A porous semiconductor according to any of 16 to 20, wherein an electroconductive porous film is disposed as an electrode at the distal ends of the columns and on an opposite surface of the porous substrate from the surface where the columns are formed.
22. A porous semiconductor according to any of 16 to 21, wherein an electroconductive porous film is disposed as one electrode at the distal ends of the columns, and the porous substrate is composed of an electroconductive material and constitutes another electrode.
23. A porous semiconductor according to 22 or 23, wherein a surface of the columns and/or a column-side surface of the electrode disposed at the distal ends of the columns is coated with particles having a photocatalytic function.
24. A filter that makes use of the porous semiconductor according to any of 15 to 24.
25. A porous semiconductor according to any of 1 to 10, wherein the porous semiconductor layer is formed by depositing semiconductor particles having a light emitting function on a surface of the porous substrate.

26. A porous semiconductor according to 25, comprising an electrode for injecting current into the porous semiconductor layer.

27. A porous semiconductor according to 25 or 26, wherein the porous semiconductor layer is composed of a deposited layer of p-type semiconductor particles and a deposited layer of n-type semiconductor particles to form a pn junction.

28. A porous semiconductor according to any of 25 to 27, wherein a surface of the semiconductor particles is coated with an insulating layer.

29. A method for manufacturing a porous semiconductor having a light emitting function and composed of a porous substrate having through-holes, and a porous semiconductor layer formed on a surface of this substrate, the method comprising at least steps of:
   (a) preparing a porous substrate and at least one of semiconductor particles having a light emitting function that works by electroluminescence, cathode luminescence, or photoluminescence;
   (b) producing a suspension of the semiconductor particles; and
   (c) filtering the suspension through the porous substrate and forming a deposited layer composed of semiconductor particles on the surface of the porous substrate.

30. A method for manufacturing a porous semiconductor according to 29, further comprising a step of forming an electrode for injecting current into the deposited layer.

31. A method for manufacturing a porous semiconductor according to 29 or 30, further comprising a step of performing a treatment for bonding together the individual semiconductor particles that form the deposited layer, after the step (c).

32. A method for manufacturing a porous semiconductor according to 31, wherein the treatment is a heat treatment.

33. A method for manufacturing a porous semiconductor according to 31, wherein the treatment is a treatment in which a semiconductor material is deposited in the vapor phase at the contact portions between the semiconductor particles.

34. A method for manufacturing a porous semiconductor according to any of 29 to 33, comprising a step of coating a surface of the semiconductor particles with an insulating layer or a material having a photocatalytic function, between the steps (a) and (b).

35. A method for manufacturing a porous semiconductor according to any of 29 to 34, wherein a step of coating a porous substrate surface with an insulating layer is added before the step (c), and a step of coating the surface of the deposited layer with an insulating layer is added after the step (c).

36. A method for manufacturing a porous semiconductor according to any of 29 to 35, wherein in the step (b), at least one of suspension of p-type semiconductor particles and at least one of suspension of n-type semiconductor particles are prepared, and in the step (c), these suspensions are alternately filtered through the porous substrate to form a deposited layer with a pn junction structure.

37. A method for manufacturing a porous semiconductor according to any of 29 to 36, wherein the average size of the semiconductor particles is from 0.01 to 5 µm.

38. A filter composed of the porous semiconductor according to any of 25 to 28.

39. A porous semiconductor according to any of 1 to 7, wherein an electrode is formed on a top or bottom surface of the porous substrate, a porous insulating layer, a porous semiconductor layer, and a porous insulating layer are laminated on the porous substrate, another electrode is formed on a top surface, the porous semiconductor layer emits ultraviolet light by electroluminescence when AC voltage is applied between the electrodes, and the porous semiconductor has a bandgap of at least 3.2 eV and is doped with gadolinium, which is the light emitting center.

40. A porous semiconductor according to any of 1 to 7, wherein an electrode is formed on a top or bottom surface of the porous substrate, the porous semiconductor layer is formed by dispersing semiconductor particles in an insulating layer, an electrode is formed on the porous semiconductor layer, the porous semiconductor layer emits ultraviolet light by electroluminescence when AC voltage is applied between the electrodes, and the semiconductor particles have a bandgap of at least 3.2 eV and are doped with gadolinium, which is the light emitting center.

41. A porous semiconductor according to 39 or 40, wherein a surface of the porous insulating layer or of the porous semiconductor layer formed by dispersing semiconductor particles in the insulating layer is covered by a porous layer having a photocatalytic function, or pore walls of the porous substrate are covered by a material having a photocatalytic function.

42. A porous semiconductor according to 39 or 41, wherein the porous insulating layer or the insulating layer in which the semiconductor particles are dispersed is formed from a material having a photocatalytic function.

43. A porous semiconductor according to any of 39 to 42, wherein the bandgap of the porous semiconductor layer or the semiconductor particles is at least 4.0 eV.

44. A porous semiconductor according to any of 39 to 43, wherein either the electrodes are porous or the structure of the electrodes has a porous structure.

45. A porous semiconductor according to 44, wherein the electrodes are composed of a porous transparent electroconductive film.

46. A method for manufacturing a porous semiconductor in which a porous insulating layer, a porous semiconductor layer, and a porous insulating layer are laminated on a porous substrate having continuous pores and having an electrode formed on its top or bottom surface, and another electrode is formed on the top surface, the porous semiconductor emitting ultraviolet light by electroluminescence when AC voltage is applied between the electrodes, the method comprising at least steps of:
   (a) preparing a suspension of gadolinium-doped semiconductor powder and a suspension of an insulator powder;
   (b) filtering the suspension of the insulator powder through the porous substrate to deposit a porous insulating layer on the porous substrate surface;
   (c) filtering the suspension of the semiconductor powder through the porous substrate to deposit a porous semiconductor layer on the insulating layer; and
   (d) further filtering the suspension of the insulator powder through the porous substrate to deposit a porous insulating layer on the semiconductor layer.

47. A method for manufacturing a porous semiconductor in which a porous semiconductor layer comprising semiconductor particles dispersed in an insulating layer is formed on a porous substrate having continuous pores and having an electrode formed on its top or bottom surface, and another electrode is formed on the top surface, the porous semiconductor emitting ultraviolet light by electroluminescence when AC voltage is applied between the electrodes, the method comprising at least the steps of:
   (a) preparing a gadolinium-doped semiconductor powder;
   (b) covering the semiconductor powder with an insulating layer and preparing another suspension thereof; and (c) filtering the suspension through the porous substrate to deposit a porous semiconductor layer on the porous substrate.

48. A filter composed of the porous semiconductor according to any of 39 to 45.

49. A bioreactor composed of the porous semiconductor according to any of 39 to 45.

50. An ultraviolet light source that makes use of the porous semiconductor according to any of 39 to 45.

51. A porous semiconductor according to any of 1 to 9, wherein the porous semiconductor layer is made of porous silicon nitride composed of columnar $Si_3N_4$ particles with an average aspect ratio of at least 3 and an oxide-based binder phase containing at least one of rare earth element, and emits visible light or ultraviolet light.

52. A porous semiconductor according to 51, wherein a surface of the columnar $Si_3N_4$ particles is covered with a film or particles having a photocatalytic function.

53. A porous semiconductor according to 51, wherein a film or deposited layer of particles having a photocatalytic function is formed on a surface of the porous semiconductor layer.

54. A porous semiconductor according to any of 51 to 53, which emits ultraviolet light having its peak wavelength at 300 to 320 nm.

55. A porous semiconductor according to any of 51 to 54, containing at least gadolinium as the rare earth element.

56. A porous semiconductor according to 55, further containing yttrium as the rare earth element.

57. A porous semiconductor according to any of 51 to 56, wherein an average pore size of the porous semiconductor layer is from 0.1 to 5 μm.

58. A porous semiconductor according to any of 51 to 57, wherein a three-point bending strength is at least 100 MPa.

59. A light emitting device having the porous semiconductor according to any of 51 to 58.

60. A filter that makes use of the porous semiconductor according to any of 51 to 58.

61. A porous semiconductor according to 1, wherein the porous substrate is columnar in shape and has formed therein in an axial direction a plurality of holes serving as passages for a fluid to be treated, the continuous pores lead from an inner wall of the holes to a side of the column, and the porous semiconductor layer is formed on the inner wall.

62. A porous semiconductor according to 1, wherein the porous substrate is a honeycomb structure, in the honeycomb structure are formed an inflow-side honeycomb passage and an outflow-side honeycomb passage separated by a partition, the continuous pores are formed inside the partition, and the porous semiconductor layer is formed on the inner walls of the inflow-side honeycomb passage.

1 Basic Structure of the Porous Semiconductor of the Present Invention

As a result of diligent research into performing sterilization and organic matter decomposition in the most efficient manner possible, the inventors discovered that the stated object can be achieved by using a filter having a light emitting function and in which the porous structure consists of a wide bandgap semiconductor material that emits ultraviolet light. Specifically, the present invention provides a porous semiconductor comprising a porous substrate having continuous pores, and a porous semiconductor layer having a light emitting function that works by electroluminescence, cathode luminescence, or photoluminescence, and having continuous pores. When electroluminescence is employed, either DC current injection or AC voltage application can be used.

The porous semiconductor of the present invention and the filter that makes use of this porous semiconductor will now be described. FIG. 1 is a diagram illustrating the structure of the filter of the present invention. This filter consists of a porous substrate and a film-form porous semiconductor layer. When bacteria or organic matter suspended in a fluid is filtered with a light emitting filter composed of a porous semiconductor membrane, any bacteria or organic matter particles larger than the pores of the porous semiconductor membrane are trapped. An electrode is formed in the porous semiconductor layer, and when voltage is applied to this, it emits light through electroluminescence. In FIG. 1b this electroluminescence is indicated by the black arrows. The trapped bacteria and organic matter particles are sterilized and decomposed by this. Alternatively, if the pores of the porous semiconductor membrane are large, the decomposition and sterilization can be performed during permeation through the membrane.

Instead of applying voltage through an electrode, sterilization and decomposition can be similarly accomplished by photoluminescence if the material is irradiated with a laser beam or the like, or by cathode luminescence if the material is irradiated with an electron beam.

There is no need to use a substrate if the only goal is sterilization or the decomposition of organic matter, but since light emitting materials such as GaN and diamond are expensive, using a substrate is preferable from a cost perspective. The porous semiconductor layer may be formed on the surface of the substrate or in the interior of the substrate. An advantage to using a substrate is that the semiconductor film does not need to be made strong as long as a high-strength porous substrate is used.

In particular, sterilization is possible when the porous semiconductor layer emits ultraviolet light of 254 nm. The shorter is the wavelength of ultraviolet light, the higher is its energy, so in terms of organic matter decomposition, a shorter wavelength is preferred because it enhances the function of directly breaking chemical bonds. Deep ultraviolet light of about 180 to 260 nm is ideal for decomposing organic matter. Meanwhile, ultraviolet light of 300 to 400 nm or higher has little ability to directly break chemical bonds, but it is still possible to decompose organic matter by such light with coating the porous semiconductor layer with photocatalyst particles such as $TiO_2$. Specifically, $TiO_2$ generates active oxygen radicals when excited by absorbing this ultraviolet light, and these radicals react with the organic matter and decompose it. It is also possible to generate ozone by ultraviolet irradiation, and use this ozone for sterilization and so forth.

For this function to be realized, it is necessary to select a semiconductor material that will emit light of a wavelength corresponding to the activation of a photocatalyst. As mentioned above, the light emission wavelengths of various materials are 227 nm for diamond, 366 nm for GaN, 200 nm for AlN, and about 370 nm for ZnO, and with an Al—Ga—N ternary semiconductor, the values can vary from 200 to 366 nm. For instance, a semiconductor with a large bandgap such as GaN, ZnO, or AlN can be used (Japanese Journal of Applied Physics, Vol. 31 (1992), publication accepted Oct. 19, 1991, pp. 51-59; Japanese Journal of Applied Physics, Vol. 30 (1992), publication accepted Aug. 20, 1991, pp. L1815-L1816). Favorable semiconductor materials in the present invention are GaN, ZnO, AlN, diamond, Ga—Al—N mixed crystals, ZnS, CdS, ZnSe, $ZnF_2$:Gd, AlN:Gd, diamond:Gd, and $CaF_2$:Gd (:Gd means doped with gadolinium). Other examples are oxides that include a rare earth element. Of these, a case of using a gadolinium-doped semiconductor material will later be described in detail.

In actual practice, impurity elements are added to these materials, so there is a fundamental shift in the emission wavelength to the shorter or longer wavelength side, but a porous semiconductor layer that emits light of the targeted wavelength can be obtained by controlling the impurity content by some known method. The electrical resistance can be controlled in addition to the bandgap of the semiconductor membrane by doping the porous semiconductor layer with any of various impurity elements. Also, the light emission efficiency can be improved by giving the porous semiconductor membrane a laminated structure and forming a pn junction, which is the same as with an ordinary light emitting diode. GaN, for example, will be p-type if magnesium is added as the doping impurity, and will be n-type if silicon is added, and the bandgap of the GaN itself can be increased by adding boron.

The shape of the crystal grains that make up the porous semiconductor layer may be spherical, but columnar grains or whiskers with a high aspect ratio are also favorable. In general, whiskers have high crystallinity with few crystal defects such as impurities or dislocations, resulting in higher intensity of emission at a wavelength corresponding to the bandgap characteristic of the semiconductor (band end emission).

When the porous semiconductor of the present invention has a porous semiconductor membrane in which such columnar or whisker crystals are three-dimensionally intertwined with each other, the strength of the porous membrane is higher, and this affords greater reliability. In addition, using a filter structured such as this allows better permeability to be achieved than with a filter made up of spherical grains. The aspect ratio here is preferably at least 3. Below this, high permeability and high strength will not be obtained.

Also, the porous semiconductor layer must have continuous pores (open pores), and the porosity is preferably at least 30%. This is because filtration resistance will be too high below 30%.

The pore size of the porous semiconductor layer preferably averages 0.0003 μm (3 Å) to 100 μm. When bacteria or viruses are to be trapped, roughly all of them can be trapped if the pore size is 0.01 μm or less. A range of 0.001 μm (10 Å) to 10 μm is called ultrafiltration and microfiltration, and is particularly favorable for trapping organic matter, bacteria, viruses, suspended matter, and so forth. As to the size of bacteria and viruses, Staphylococcus is about 0.9 μm, E. coli about 1 μm, typhus bacteria about 0.6 μm, smallpox bacteria about 0.2 μm, and most bacteria about 0.5 to 1 μm, so the pore size of the porous semiconductor layer should be controlled to a size at which these can be trapped.

If the pore size is less than 0.001 μm, the product can also be used as a gas separation membrane. For instance, with a mixture of two or more gases including a toxic gas, just the toxic gas can be passed through the pores, during which time the pore walls emit ultraviolet light and decompose the toxic gas. To produce micropores, the crystal grains that make up the semiconductor membrane must be extremely fine, but since a quantum size effect appears at such small scales, light of a wavelength shorter than the band edge of the semiconductor material being used can also be produced. The thickness of the porous semiconductor layer is preferably 1 to 1000 μm. In particular, if the particles have a core/shell structure in which a plurality of semiconductor particles whose size is 10 μm or less are dispersed in a single large particle, then the quantum size effect and quantum confinement effect will be very pronounced, which is preferable in that the light emission intensity will be higher.

The porous substrate that supports that porous semiconductor layer must be resistant to ultraviolet light and have enough heat resistance to allow the formation of a semiconductor membrane, so a porous ceramic or metal is used. If the substrate is made from a metal or an electrically conductive ceramic such as SiC or GaN, then it will serve as an electrode at the same time, which is convenient in the production of a light emitting element. Furthermore, if the substrate is porous high-strength $Si_3N_4$ in which $\beta$-$Si_3N_4$ grains grown in the form of columns are three-dimensionally intertwined, then the substrate thickness can be reduced, which affords a reduction in pressure loss during filtration. Preferred materials for the substrate of the present invention are SiC, AlN, $Si_3N_4$, silicon, SUS 316, $Al_2O_3$, and GaN.

The average pore size of the porous substrate is preferably 0.01 to 1000 μm. Below 0.01 μm, pressure loss during filtration will be large and permeation performance will suffer. If 1000 μm is exceeded, though, it will be difficult to form the porous semiconductor layer. The porosity of the porous substrate is preferably at least 30%, just as with the porous semiconductor layer.

Using a filter such as this allows a system that used to require a filtration membrane and a light emitting source to comprise just a single component, which not only greatly lowers the cost, but also leads to reductions in steps and installation space. Also, since a semiconductor light emitting diode generates little heat, modification of the filtration liquid that would otherwise be caused by elevated temperatures can be minimized.

When the porous semiconductor of the present invention is used as a filter, a ceramic is preferred as the substrate of the filter. In the actual industrial use of a ceramic filter, it is desirable for it to be in the form of a module in which the semiconductor membrane surface area per unit of volume has been increased in order to make the filtration apparatus more compact. Specifically, the performance of a filter can be expressed as the product of the amount of permeation per unit of surface area times the membrane surface area. With this in mind, the inventors developed a filter formed in what is called a monolithic shape, a cross section of which is in the shape of a lotus root, for example, as will be shown in the examples given below. With a monolithic shape, the filter is in the form of a column when viewed as a whole, and there are a plurality of holes extending along the axis of the column. Specifically, a plurality of circular or polyhedral holes are made in the axial cross section of the column of a porous ceramic substrate (support) with large pores, and these holes serve as passages for the raw liquid or the fluid to be treated. The ends of the monolithic column may be either open or closed. A filtration layer with a small pore diameter, that is, a semiconductor layer, is formed on the insides of these passages. In some cases, an intermediate layer is formed which has a pore size in between those of the substrate and the filtration layer. The clarified liquid that has been filtered flows out from the side of this filter. This affords a larger surface area per unit of volume. With an ordinary microfiltration filter, the pore size of the ceramic porous substrate is at least 10 μm, while that of the filtration layer is 1 μm or less.

The porous substrate can also be formed as a honeycomb structure. A honeycomb structure can be used to advantage in the purification of a gas. In this case, the fluid being treated flows into the inflow-side honeycomb passage, and is guided to an outflow-side honeycomb passage through continuous pores in a partition provided with a porous semiconductor layer. This honeycomb structure may also be formed in a monolithic shape.

2 Method for Manufacturing the Porous Semiconductor

The method for manufacturing the porous semiconductor of the present invention will now be described.

The porous semiconductor layer of the present invention can be manufactured by a variety of methods, but the following description will be for particular cases in which it is manufactured using chemical transport, CVD, sublimation, and electrical heating methods, for example.

(1) Chemical Transport

A chemical transport method can be performed using the apparatus shown in FIG. 2, for instance. As shown in FIG. 2, a mixed powder of ZnO powder and graphite powder is placed in a boat inside a tube furnace, and heated at a temperature of 900 to 925° C. in an argon gas flow and under atmospheric pressure to generate zinc gas and carbon monoxide. When an $Si_3N_4$ porous substrate (25 mm diameter×1 mm) that has been coated with gold is placed a little away from the center of the furnace, the generated gas is transported and reacts on the substrate, causing ZnO whiskers with excellent crystallinity to precipitate. The following reactions occur in the high temperature (900 to 925° C.) and low temperature portions of the furnace.

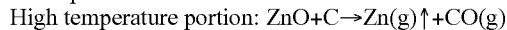
High temperature portion: $ZnO+C \rightarrow Zn(g)\uparrow +CO(g)$
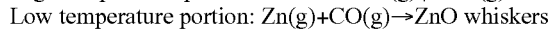
Low temperature portion: $Zn(g)+CO(g) \rightarrow ZnO$ whiskers This forms porous $Si_3N_4$ coated with ZnO nano-whiskers, as is depicted schematically within the circle in FIG. 2. An electrode is formed on this as shown in FIG. 1, and voltage is applied, which generates ultraviolet light with a wavelength of 370 nm corresponding to the bandgap of ZnO.

(2) CVD

CVD can be performed using the apparatus shown in FIG. 3a, for instance. A suspension is prepared by dispersing a GaN powder in an alcohol, and this suspension is filtered through the porous substrate, which produces a porous substrate having a porous deposited layer (cake layer) of GaN as shown in FIG. 3b. The porous substrate is placed in a furnace and held at about 600° C. Liquid gallium placed somewhere else in the furnace is heated to about 850° C., in which state HCl gas and $H_2$ gas (carrier gas) are introduced, which generates $GaCl_3$ gas. This is transported onto the substrate, where it reacts with $NH_3$ gas introduced through a separate port, which results in the necking of the GaN particles formed on the porous substrate and produces a porous GaN film (FIG. 3c).

(3) Sublimation

Sublimation can be performed using the apparatus shown in FIG. 4, for instance. AlN powder is charged into a crucible and heated to a high temperature of 2100° C. to generate aluminum gas and $N_2$ gas. When a ceramic porous substrate is placed at a location about 200° C. cooler than the crucible, a porous film composed of AlN microcrystals is produced on the porous substrate. This process is usually called sublimation, and is used to grow SiC single crystals, but if the precipitation rate is adjusted so as not to be extremely high, then a porous polycrystalline film will be produced rather than single crystals. The AlN thus produced will be columnar in shape, or in the form of flat hexagons.

(4) Electrical Heating

As shown in FIG. 5, a suspension is prepared by dispersing a powder of ZnO in water, and this suspension is filtered through the porous substrate to form a deposited layer of ZnO called a cake layer on the substrate surface. An electrode is formed on the ZnO cake layer, and this is electrically heated, which raises the surface temperature to 1000° C. or higher and generates zinc vapor and oxygen or $H_2O$ vapor, which once again reacts and condenses on the substrate surface, producing ZnO whiskers.

A powder of silver or gold may also be mixed with the ZnO powder and similarly heated electrically. In this case, whiskers are produced by what is known as a VLS (vapor-liquid-solid phase) mechanism in which the produced gas species is dissolved in the liquid metal (melted by heating) and then precipitates. An advantage to this method is that the metal phase is interspersed between the whiskers, or between the whiskers and the substrate, resulting in a strong bond.

(5) Other

Another method for producing a porous semiconductor is to anodize the above-mentioned wide-bandgap semiconductor substrate so as to form micropores in the surface layer, perpendicular to the substrate. The anodization can be applied for the following process. First, a commonly used light emitting diode (solid) having a pn junction is produced, and before an electrode is formed on this, through-holes are formed by anodization or microworking so as to render the diode porous. Pores formed by anodization are particularly fine (from just a few angstroms to a few thousand angstroms), making this method better for the purpose of obtaining light emission of a wavelength shorter than the wavelength corresponding to the bandgap of the semiconductor being used. Also, this method can be considered particularly good at imparting a gas separation function because fine through-holes are formed perpendicular to the substrate.

3 Structure of a Filter Made Using a Porous Semiconductor

The structure of a filter actually produced using the above-mentioned porous semiconductor will now be described. The porous semiconductor is basically composed of a porous substrate and a porous semiconductor layer. From the standpoint of its function as a filter, it must be provided with a filtration layer that handles the filtration duties and a light emitting layer having a light emitting function.

(1) Structure in Which the Filtration Layer Doubles as the Light Emitting Layer

As shown in FIG. 6(a), a porous semiconductor layer is formed on the surface of a porous substrate, and this porous semiconductor layer serves as both a filtration layer and a light emitting layer. An electrode is formed on the surface of the porous substrate and the porous semiconductor layer. If the electrode covers the entire surface, then no filtration function will be possible, so the electrode is made comb-shaped. If the electrode is made of an indium tin oxide conductive material (ITO film), then the ITO film may cover the entire surface as long as it has a porous structure. The material to be trapped that is present in the liquid or gas is trapped by the filtration layer, and at the same time is decomposed or sterilized by the ultraviolet light that is generated.

(2) Structure in Which the Filtration Layer and Light Emitting Layer are Different As shown in FIG. 6(b), the substrate itself serves as the filtration layer, and a comb-shaped electrode is formed on both sides of the porous semiconductor layer serving as the light emitting layer. In this structure, the other electrode is embedded in the filtration layer in order to impart electric potential directly to the light emitting layer. The matter to be trapped that is present in the liquid or gas is trapped by the filtration layer, and the clarified fluid is irradiated with ultraviolet light. With this type of filter, the trapped matter is not directly irradiated with ultraviolet light, and instead the clarified fluid that has passed through the filtration layer is irradiated with the ultraviolet light, which is an effective way to kill any bacteria and so forth remaining in the clarified fluid.

If a conductive liquid is what is being filtered, then the applied voltage will pass not only through the semiconductor layer, but also through the liquid, so in this case the higher the electrical conductivity of the semiconductor layer or the substrate is raised, the more current will flow through the semiconductor layer and contribute to light emission.

Also, a commonly used pn junction structure, quantum well structure, or the like may be used for the light emitting layer in the above-mentioned (1) and (2) in order to improve the performance as a light emitting diode, that is, to achieve higher light emitting efficiency at a lower power level. FIG. 7(a) is an example of this, in which a porous GaN layer formed on a porous SiC substrate is divided into three layers, and light is emitted from the electron and hole pairs injected into the active layer. With a structure such as this, as the thickness of the p-GaN layer is reduced, it becomes easier for the ultraviolet light generated from the light emitting layer to reach the surface of the p-GaN layer, so the decomposition and sterilization of organic matter, bacteria, and so forth are carried out more efficiently. Also, as shown in FIG. 7(b), it is preferable for a pn junction to be formed from AlN, which has a larger bandgap than the AlGaN that makes up the active layer, because the ultraviolet light generated from the active layer will pass through the AlN more easily.

4 Porous Semiconductor in which the Porous Semiconductor Layer is Made up of Columns The inventors also discovered that, in regard to performing sterilization and organic matter decomposition extremely efficiently, a porous semiconductor and a filter with superior light emitting function can be obtained by employing a porous structure in which the wide-bandgap semiconductor material that emits ultraviolet light is composed of columns. Specifically, a preferred aspect of the present invention provides a porous semiconductor, comprising a porous substrate having continuous pores, and a porous semiconductor layer having a light emitting function that works by electroluminescence, cathode luminescence, or photoluminescence, and having continuous pores, wherein the porous semiconductor layer is composed of numerous columns of semiconductor material erected on the surface of the porous substrate.

The porous semiconductor in this aspect will be described through reference to the drawings.

FIG. 13 is a schematic diagram illustrating the basic conceptual structure of the porous semiconductor of the present invention. This porous semiconductor comprises a porous substrate and columns that serve as a porous semiconductor layer, which are grown perpendicular to the porous substrate plane. When any bacteria or organic matter suspended in a fluid is filtered using this porous semiconductor as a filter, those bacteria and organic matter larger than the average pore size of the porous substrate are trapped. An electrode may be formed on the porous semiconductor, and when voltage is applied to this electrode, light is emitted by electroluminescence, resulting in the sterilization and decomposition of any trapped bacteria and organic matter. Instead of applying voltage through an electrode, sterilization and decomposition can be similarly accomplished by photoluminescence if the material is irradiated with a laser beam or the like, or by cathode luminescence if the material is irradiated with an electron beam.

The present invention has the function of trapping organic matter, bacteria, viruses, and so forth on the surface or in the interior of a filter, then directing ultraviolet light at the trapped matter to sterilize or decompose it. From the standpoint of a filter, it is preferable to achieve 100% physical trapping by means of the relation between the pore size of the porous material and the size of the bacteria, viruses, or other trapped material, and an advantage is that even if part of the filter structure should be destroyed and the matter to be trapped pass through the filter, it will still be decomposed or sterilized by the ultraviolet light. FIGS. 18(a) and 18(c) correspond to this type of filter. In FIG. 18, the black circles represent the particles that are to be trapped. FIG. 18(a) shows a filtration layer that doubles as a light emitting layer. In FIG. 18(c) the filtration layer and the light emitting layer are separate, and the particles are trapped on the surface of the light emitting layer or the surface of the filtration layer.

This filter can function as a filter even if its pore size is larger than the bacteria, viruses, etc. In this case, as the matter passes through the filter without being trapped, it is decomposed or sterilized by ultraviolet irradiation. With a filter of this type, the pore size can be larger than the matter to be trapped, so an advantage is that this filter offers excellent permeation performance with gases and liquids. The larger are the pores in the porous semiconductor layer, the higher the permeation performance, but if the pores are too large, the distance between the irradiating ultraviolet light and the matter to be trapped may be so long that the light is attenuated. FIGS. 18(b) and 18(d) correspond to this type of filter. In FIG. 18, the white circles represent the remains of the particles that have been decomposed or sterilized. In (b) and (d), the matter that is to be decomposed or sterilized by ultraviolet irradiation passes through the filtration layer and the light emitting layer, during which time it is decomposed or sterilized.

Because of the above, the present invention can also be used as follows. Relatively large suspended matter and so forth is trapped by the filtration function of the filter, while relatively small matter that is to be decomposed or sterilized is decomposed or sterilized by ultraviolet irradiation as it passes through the porous semiconductor layer.

The sterilizing action is particularly powerful when the porous semiconductor layer emits ultraviolet light of 254 nm as above, and it is therefore preferable in terms of sterilization for the semiconductor layer to emit ultraviolet light of 230 to 270 nm. Furthermore, deep ultraviolet light of about 180 to 260 nm is optimum for the decomposition of organic matter. Although ultraviolet light of 300 to 400 nm has only a minimal function of directly breaking chemical bonds, organic matter can be decomposed in this case by coating the surface of the columns and/or the column-side surface of the electrode disposed at the distal ends of the columns with particles having a photocatalytic function. Specifically, the particles having the photocatalytic function absorb this ultraviolet light, and the light excites them to generate active oxygen radicals, which react with the organic matter and decompose it. $TiO_2$ is an example of particles that have a photocatalytic function.

The above-mentioned metal and ceramic materials are preferred as the porous substrate, and if the substrate is made from a metal or a conductive ceramic such as SiC or GaN, then it will also serve as an electrode, which is convenient in the production of a light emitting element. Also, it is preferable to use a silicon substrate in the growth of ZnO whiskers as the columns because the whiskers will tend to grow perpendicularly.

It is preferable for the pores in the porous substrate to be through-holes perpendicular to the substrate plane, and it is also preferable for the average pore size to be 0.1 to 100 µm. If the average pore size is less than 0.1 µm, there will be more pressure loss during filtration, and this decreases permeation performance. On the other hand, if 100 µm is exceeded, then large particles that cannot be decomposed or sterilized by ultraviolet light will also end up passing through. Making the pores through-holes which are perpendicular to the substrate plane also minimizes pressure loss during filtration, which affords a filter with higher permeation performance.

If the semiconductor layer is in the form of columns, and especially columns that are pointed at their distal ends, there will be an electron containment effect at the distal ends during the application of electric power, which results in better light emitting efficiency. The columns may be a single whisker with a columnar structure. Since whiskers have high crystallinity and few impurities or defects, they allow the light to be emitted more efficiently.

It is preferable for the semiconductor layer composed of columns or oriented whiskers to be one or more of ZnO, GaN, AlN, and diamond. The following are examples of how these are produced.

(1) Method for Manufacturing a Porous Semiconductor When the Columns are Diamond The following process is a known method for producing columnar diamond (see Japanese Patent Publication 2002-75171). First, this will be described through reference to FIG. 14. As shown in FIG. 14(a), a substrate 21 composed of monocrystalline Ib diamond (001) is readied. Then, in the step in FIG. 14(b), a resist layer 22 is formed on the substrate 21, over which is disposed a photomask 23 on which circular shades 23a have been formed two-dimensionally. The pitch of the shades 23a on the photomask 23 is about 1 to 50 μm, for example. A two-dimensional pattern corresponding to the locations of the shades 23a of the photomask 23 is then formed by lithography in the resist layer 22.

After this, in the step shown in FIG. 14(c), mask components 24 corresponding to the a pattern of the resist layer 22 are formed by lithography. In the step shown in FIG. 14(d), the substrate 21 is subjected to reactive ion etching (RIE) to form a plurality of columns 25 composed of monocrystalline diamond. The columns 25 have a circular cross section in the example illustrated here, but may instead be quadrangular, triangular, etc. The height of the columns 25 is about 1 to 20 μm, the diameter of the columns 25 is preferably about 0.5 to 10 μm, and the ratio of the height of the columns 25 to their diameter (hereinafter referred to as the "aspect ratio") is preferably about 1 to 5. The reason reactive ion etching is used to form the columns 25 is that not only can protruding columns 25 be formed easily, but the portion where the columns 25 are not formed can be smoothly etched. $O_2$ alone or a mixture of $CF_4$ and $O_2$ can be used favorably as the reaction gas used in the reactive ion etching.

A method other than reactive ion etching may also be used in forming the columns 25, examples of which include ion beam etching, electron cyclotron resonance (ECR) etching, and etching by inductive coupled plasma (ICP).

Then, in the step shown in FIG. 14(e), the columns 25 are subjected to plasma etching in a microwave plasma to form electron emission components 30. The plasma etching is preferably conducted in a gas of 100% oxygen, at a reaction temperature between room temperature and about 200° C., and at a reaction chamber pressure of 0.1 to 40 Pa (close to 5 Pa is particularly good), or in a mixed gas of $CF_4$ (mol)/$O_2$ (mol)≦approximately 0.25, at a reaction temperature between room temperature and about 200° C., and at a reaction chamber pressure of 0.1 to 40 Pa (close to 5 Pa is particularly good). Also, the plasma etching may be performed in a DC plasma, arc jet plasma, flame plasma, or other such plasma rather than in a microwave plasma. Furthermore, the substrate 21 was composed of monocrystalline diamond in this example, but a heteroepitaxial diamond substrate or a highly oriented film substrate may be used instead.

It is also possible to form the substrate from polycrystalline diamond of random orientation, although the characteristics of the light emitting element will suffer somewhat. Also, the substrate 21 is not limited to a (001) substrate, and may instead be a (100), (110), or (111) substrate.

The inventors discovered a method for manufacturing a porous semiconductor composed of a porous substrate and columnar diamond on the basis of the above technology. This will be described through reference to FIG. 15. First, a diamond monocrystalline film is formed on a conductive silicon substrate. This is joined to a porous substrate by a suitable method. The shape of the photomask is devised so as to form shades on the diamond film surface in the shape shown in FIG. 15(a). Specifically, the shade structure comprises circular aluminum shades connected by thin wires. When this is etched, the diamond portion with no shade is etched, forming holes, and the silicon of the substrate is also etched, which finally forms the columns shown in FIG. 15(b).

At this point, the diamond under the thin wires of the shades also ends up being etched, so that in the end only linear shades remain, and the diamond disappears from underneath these. As shown in FIG. 15(c), as the etching proceeds, the diamond becomes pointed, with the aluminum shades remaining at the distal ends. As a result, as shown in FIG. 15(d), the columns each consist of a base component composed of silicon and a pointed component located at the distal end side of this base component. The aluminum shades serve as an upper electrode just as they are. The porous substrate joined to the silicon substrate at the outset serves as the back electrode.

When voltage is applied to a structure such as this, ultraviolet light is emitted by electroluminescence. Basically, the wavelength corresponding to the bandgap of diamond is about 227 nm, but this bandgap can be increased by adding impurities to the diamond, thereby shifting the emitted light to around 254 nm.

Sterilization can be carried out efficiently when the porous semiconductor emits ultraviolet light of 254 nm. As shown in FIG. 16, it can be seen that if a pn junction is formed in advance during the formation of the diamond film, since the pn junction is formed in the lengthwise direction of the columns, it will be possible to emit ultraviolet light at a high level of energy efficiency as current injection electroluminescence. To obtain p-type diamond, boron is effective as the dopant, while phosphorus or sulfur is effective in order to obtain n-type diamond. Alternatively, both of these dopants can be used at the same time. The steps in FIGS. 16(b) to 16(d) are the same as those described in FIG. 15.

(2) Method for Manufacturing a Porous Semiconductor When the Columns are ZnO

A substrate can be directly coated with ZnO whiskers that can be oriented. For instance, ZnO whiskers that can be oriented can be obtained by sublimating $Zn(C_5H_7O_2)_2$, which is an alkoxide of zinc, as the raw material at about 130° C., transporting this with $N_2$ gas, and spraying it from a slit nozzle perpendicularly on the porous substrate. Adhesion to the substrate will be better if the substrate temperature is about 550 to 600° C. Because it involves growing whiskers at atmospheric pressure, this method is very practical as a low-cost process for obtaining a porous semiconductor.

Just as with diamond, the light emission efficiency will be higher if a pn junction is formed in the growth direction of the ZnO whiskers. Aluminum or gallium should be added to the raw material gas to produce an n-type material, and nitrogen, phosphorus, arsenic, or the like should be added to produce a p-type material.

Furthermore, the columns used in the present invention are not limited to diamond or ZnO, and may be GaN, AlN, or mixed crystals of these.

5 Porous Semiconductor in which the Porous Semiconductor Layer is Formed by Depositing Semiconductor Particles The inventors also discovered that, in regard to performing sterilization and organic matter decomposition extremely efficiently, obtaining a porous semiconductor by the deposition of semiconductor particles as another preferred aspect of the present invention is an effective way to solve the problems discussed above. Specifically, as another preferred aspect, the present invention provides a porous semiconductor comprising a porous substrate having continuous pores, and a porous semiconductor layer having a light emitting function that works by electroluminescence, cathode luminescence, or photoluminescence, and having continuous pores, wherein the porous semiconductor layer is formed by depositing semiconductor particles having a light emitting function on the surface of the porous substrate.

FIG. 22 illustrates the basic structure of a filter in which the porous semiconductor of the present invention is used. The present invention comprises a porous substrate and a porous semiconductor layer. When any bacteria or organic matter suspended in a fluid is filtered through a light emitting filter composed of a porous semiconductor, those bacteria and organic matter larger than the pore size of the porous substrate are trapped. When an electrode is formed on the porous semiconductor and voltage is applied to this electrode, light is emitted through electroluminescence, and irradiation with this light results in the sterilization and decomposition of any trapped bacteria and organic matter. Photoluminescence produced by laser beam irradiation or cathode luminescence produced by electron beam irradiation can also be utilized.

The porous semiconductor layer may be formed on the surface of the substrate or in the interior of the substrate. If the substrate has high conductivity, a back electrode should be formed on the back side of the substrate. If the substrate has low conductivity, an electrode may be formed between the porous semiconductor layer and the porous substrate, unlike in FIG. 22. The electrode may be porous by making use of a porous material, or the material may be solid but formed in a porous structure. One example of this would be a mesh shape.

In FIG. 22, the particles 1 represent small particles that are to be decomposed or sterilized, while the particles 2 represent relatively large particles that are not to be decomposed or sterilized. FIG. 22(a) is a diagram of when the diameter relationships are such that the pore size of the filtration/light emitting layer (porous semiconductor layer)<diameter of particles 1<diameter of particles 2. All of the particles here are trapped by the filter function of the porous semiconductor layer, and the particles 1 are decomposed or sterilized by ultraviolet light. In this case, basically all of the particles are physically trapped by the filter function, and when this is used to purify a gas as in FIG. 23, for example, if there is no ultraviolet light irradiation function, then anything that is first trapped on the surface of the filter will be released back into the gas, which lowers the purification efficiency. When an ultraviolet light irradiation function is provided, all of the particles that reach the filter surface or the vicinity thereof are decomposed or sterilized.

Meanwhile, FIG. 22(b) is a diagram of when the diameter relationships are such that the diameter of particles 2>pore size of the filtration/light emitting layer>diameter of particles 1. Only the larger particles 2 are trapped by the filter function of the porous semiconductor layer, while the smaller particles 1 pass through the filtration layer and the porous substrate, but are decomposed or sterilized by ultraviolet light while passing through the filtration layer. An advantage in this case is that since the pore size of the filtration layer is larger than in the case of FIG. 22(a), basically the filter has higher permeation performance.

The ultraviolet light wavelength and function in the filter are as discussed above. The shorter the wavelength, the more effectively organic matter is decomposed, but even with ultraviolet light of 300 to 400 nm or higher, decomposition will be possible if the porous semiconductor layer is coated with $TiO_2$ photocatalyst particles. For this function to be realized, it is necessary to select a semiconductor material that will emit light of a corresponding wavelength as discussed above. In addition to selection of the material, doping with any of various known impurity elements and controlling the amount of impurity are other ways to produce a porous semiconductor film that will emit light of the desired wavelength and to control the electrical resistance. Also, the porous semiconductor film can have a layered structure and a pn junction can be formed by doping with a suitable impurity, which further raises the light emitting efficiency.

A method for manufacturing a porous semiconductor film such as this will now be described through reference to FIG. 24, using as an example a case in which GaN is used as the semiconductor material. First, GaN powder is dispersed in an alcohol or other liquid to prepare a suspension, and this is filtered through a porous substrate to form a porous deposited layer (cake layer) of GaN on the porous substrate surface. Naturally, a porous substrate having an average pore size smaller than the pore size of the GaN powder is selected in this case. To form a pn junction structure, first form a cake layer of n-type powder, and then form a cake layer of a p-type powder, as shown in FIG. 25.

When a GaN powder is simply laminated, rather than employing a pn junction structure, light can be emitted by sending alternating current through the electrode. It is said that since the GaN powder is oxidized in the air and an oxide film formed on its surface, the GaN powder is embedded in an oxide insulating layer, and therefore when AC voltage is applied, light is emitted through the interaction of charges as the interface between the GaN and the oxide layer, for example.

An insulating layer may also be formed in another step on the GaN powder surface. The material of the insulating layer may be $SiO_2$, or it may be an oxide of gallium such as $Ga_2O_3$. An oxide of gallium is easier because it can be formed merely by heating a GaN powder in the air. Coating the porous substrate with an insulating layer as well, rather than just the porous semiconductor layer or the surface of the semiconductor particles, is also effective. The insulating layer may be any substance having a photocatalytic function, such as $TiO_2$. Efficiency is extremely high in this case because the ultraviolet light generated from the semiconductor particles can excite the photocatalyst directly. The thickness of the photocatalyst layer is preferably no more than 1 μm, but a thicker layer may sometimes be used if the photocatalyst particles are smaller. Any standard sol-gel method or vapor phase method is more than adequate for applying the insulating layer. Meanwhile, when a pn junction structure is formed, light can be emitted by sending current through directly.

The average size of the semiconductor particles is preferably from 0.01 to 5 μm. If the particles are larger than 5 μm, the mechanical strength of the cake layer will decrease, making handling more difficult, and at the same time numerous crystal defects will be introduced into the powder, resulting in a decrease in luminous intensity at the band ends of the semiconductor. If the particles are smaller than 0.01 μm, the cake layer will tend to crack and destroy the film during the drying of the cake layer. It is good to add a tiny amount of binder component to the suspension in order to prevent cracking.

Furthermore, it is undesirable for the semiconductor particles to be smaller than 0.01 µm because capture of the carriers (electrons or holes) will occur at the particle surface, which generally decreases the light emission efficiency. This is because asymmetric electron pairs called dangling bonds on the particle surface trap (capture) the carriers. Thus, even if the particles are smaller than 0.01 µm, if the particle surface is surrounded with another substance, the quantum size effect inherent in nanoparticles will come into play and the luminous intensity will be higher. Most effective of all is a core/shell structure in which a plurality of nanoparticles are dispersed in matrix particles of a certain size. The shell here may be made of either inorganic or organic material, but if it is a semiconductor or insulator with a larger bandgap than the semiconductor particles serving as the core, there will be quantum confinement in which the carriers are confined in the core particles, resulting in even higher light emission efficiency.

It is preferable for the porous semiconductor layer to be thinner. Greater thickness requires greater voltage to emit light. Nevertheless, a thick porous semiconductor layer can be favorable in that the surface area of the semiconductor particles will be greater, which results in higher efficiency of decomposition or sterilization when the product is used as a filter.

At this stage at which just a cake layer has been formed, the GaN powder particles are merely touching each other, so the luminous intensity will not be that high when voltage is applied after electrode formation. To increase the luminous intensity, it is preferable to place the sample after cake layer formation in an ordinary GaN film coating furnace, and perform a treatment that will suitably fill in the gaps between the GaN particles. The following is an example of how this treatment can be performed.

The porous substrate on which a cake layer has been formed is placed in the furnace, and the substrate is held at about 600° C. Liquid gallium that has been placed somewhere else inside the furnace is heated to about 850° C., and in this state HCl gas and $H_2$ gas (carrier gas) are introduced, which generates $GaCl_3$ gas. This is transported onto the substrate, where it reacts with $NH_3$ gas introduced through a separate port, which results in the necking of the GaN particles formed on the porous substrate and produces a porous GaN film. This treatment forms a tough skeleton of GaN, so the injected current can participate in light emission without any great loss.

The porous substrate that supports the porous semiconductor film is preferably one of the above-mentioned ceramic or metal materials, and the average pore size is again preferably 0.01 to 1000 µm.

6 Porous Semiconductor Having an Insulating Layer

As another preferred aspect having sufficient light emitting brightness, the present invention provides a porous semiconductor comprising an insulating layer, or comprising a porous semiconductor layer in which semiconductor particles are dispersed in an insulating layer.

Specifically, the present invention provides a porous semiconductor, comprising a porous substrate having continuous pores, and a porous semiconductor layer having a light emitting function that works by electroluminescence, cathode luminescence, or photoluminescence, and having continuous pores, wherein an electrode is formed on a top or bottom surface of the porous substrate, a porous insulating layer, a porous semiconductor layer, and a porous insulating layer are laminated on the porous substrate, another electrode is formed on the top surface, the porous semiconductor layer emits ultraviolet light by electroluminescence when AC voltage is applied between the electrodes, the porous semiconductor has a bandgap of at least 3.2 eV, and is doped with gadolinium, which is the light emitting center, or a porous semiconductor, comprising a porous substrate having continuous pores, and a porous semiconductor layer having a light emitting function that works by electroluminescence, cathode luminescence, or photoluminescence, and having continuous pores, wherein an electrode is formed on the top or bottom surface of the porous substrate, the porous semiconductor layer is formed by dispersing semiconductor particles in an insulating layer, an electrode is formed on the porous semiconductor layer, the porous semiconductor layer emits ultraviolet light by electroluminescence when AC voltage is applied between the electrodes, the semiconductor particles have a bandgap of at least 3.2 eV, and are doped with gadolinium, which is the light emitting center.

FIG. 29 illustrates the concept of a double-insulated structure pertaining to this aspect of the present invention. In FIG. 29, 1 is an electrode, 2 is a porous insulating layer, 3 is a porous semiconductor layer, and 4 is a porous substrate. If the porous substrate is conductive, then using a back electrode as shown in FIG. 29(b) is also possible.

FIG. 30 illustrates a particle dispersion type of structure that is another concept pertaining to the present invention. In FIG. 30, 1 is an electrode, 2 is a porous insulating layer, 5 is semiconductor particles, 4 is a porous substrate, and 6 is a porous light emitting layer (porous semiconductor layer). Although the surface of the semiconductor particles 5 is covered by the insulating layer 2 in this case, the structure may instead comprise semiconductor particles mixed with insulating layer particles. The layer of semiconductor particles covered by the insulating layer, or the mixed layer of semiconductor particles and insulating layer particles, on the whole forms the porous semiconductor layer of the present invention.

$ZnF_2$:Gd is known as a semiconductor material that emits ultraviolet light of high luminance. The inventors discovered that a porous semiconductor that emits light of higher luminance than would be achieved with porous GaN, ZnO, or the like can be obtained by making this semiconductor material porous.

In particular, this aspect is characterized in that a semiconductor whose bandgap is at least 3.2 eV is doped with gadolinium. When voltage is applied between the electrodes, electrons called hot electrons are injected into the semiconductor layer, and these are accelerated by the electric field and excite the gadolinium ions from their ground state. When the excited gadolinium ions make the transition back to their ground state, they emit light in a wavelength equivalent to the amount of energy lost. In the case of gadolinium, the wavelength of the emitted light is about 311 nm, so the light is ultraviolet. Ultraviolet light of 311 nm is particularly effective at decomposing dioxins.

Here, the bandgap of the semiconductor doped with gadolinium is at least 3.2 eV. If it is less than 3.2 eV, then all of the 311 nm ultraviolet light emitted from the gadolinium will be absorbed by the semiconductor and cannot be taken off to the outside. Basically, it is preferable for the bandgap of the semiconductor combined with the gadolinium (the light emitting center) to be at least 4.0 eV. In this case the semiconductor will transmit all light of at least 310 nm, so absorption drops to zero.

Of the semiconductors having this bandgap, the most effective material is $ZnF_2$. Also, with AlN-GaN-based mixed crystals, a bandgap of 4.0 eV or higher can be achieved by raising the proportion of aluminum. Naturally, AlN may also be used. Diamond is also favorable because of its large bandgap of 5.47 eV. Another candidate material is MgS. The use of a semiconductor material such as the above allows much more intense ultraviolet light to be generated than when GaN, ZnO, or the like is used.

There are no particular restrictions on the insulating layer, but examples of materials that can be used include $Ta_2O_5$, $TiO_2$, $Al_2O_3$, $SiO_2$, $BaTiO_3$, $PbTiO_3$, $PbZrO_3$, $SrTiO_3$, and $Si_3N_4$. A resin having properties as a dielectric may also be used. It is preferable for the insulating material to have a higher dielectric constant because the voltage applied to the semiconductor layer will be higher, on the other hand, a drawback to a higher dielectric constant is that the semiconductor will be more prone to insulation breakdown, so such material has conflicting characteristics. Of the above materials, if one is selected that will exhibit a photocatalytic function upon irradiation of ultraviolet light, such as $TiO_2$, then organic matter and harmful gas components and so forth can be decomposed. Ultraviolet light emitted from the light emitting center excites $TiO_2$, generating radicals and holes, and these decompose organic matter. Especially when the surface of the semiconductor particles is uniformly covered by $TiO_2$, all of the ultraviolet light emitted from the semiconductor particles excites the $TiO_2$, so this is the most efficient approach for a photocatalytic function to be exhibited.

If $TiO_2$ is not used for the insulating layer, ways for supporting a photocatalytic material include forming a porous $TiO_2$ layer on the surface of the insulating layer, and covering the pore walls of the porous substrate with $TiO_2$. For the photocatalytic action to be exhibited more efficiently, it is important to increase the surface area of the $TiO_2$ layer so as to increase the surface area in contact with the gas or liquid being treated. To this end, if the $TiO_2$ particles that make up the $TiO_2$ layer are made smaller in size, or if $TiO_2$ is used for the insulating layer in a particle dispersion type of structure, then it is important for the semiconductor particles themselves to be made into microparticles.

$TiO_2$ is generally anatase, which affords an excellent photocatalytic function, but a rutile type, which has a somewhat smaller bandgap than an anatase type, may be used instead. A photocatalyst that works by visible light, such as one based on Ti—O—N, may also be used. In this case, the light emitted from the porous semiconductor layer need not be ultraviolet light, and may instead be visible light.

If the semiconductor particles are made extremely fine, the bandgap of the semiconductor material widens and a quantum size effect appears, so light is emitted at a shorter wavelength (higher energy level) than that corresponding to the bandgap originally had by the material. Also, the threshold voltage at which light is emitted will decrease in this case, so less power will be consumed, or light will be emitted at a high luminance. Therefore, making the semiconductor particles into microparticles is an effective way to improve the performance of the finished product. Particles having the above-mentioned core/shell structure are particularly favorable.

Either the electrode itself is porous, or the electrode structure is porous. Examples of porous structures include a mesh and a spiral. If an indium tin oxide-based transparent conductive film (ITO film) is used for the electrode, then the ultraviolet light emitted from the light emitting layer can be taken off to the outside without any loss, so this is effective when the light emitting layer is provided on the outside of the insulating layer.

The porous semiconductor pertaining to the present invention can be produced by a variety of methods. Examples include a method in which the powder that makes up the semiconductor or the insulating layer is filtered through the porous substrate to form a porous layer called a cake layer, a method in which pores are formed in a solid semiconductor film by an electrochemical method such as anodization, and a method in which semiconductor whiskers are used.

The semiconductor (such as $ZnF_2$:Gd) that makes up the light emitting layer is obtained, for example, by mixing a $ZnF_2$ powder and a $GaF_3$ powder in a specific composition, and then firing this mixture in an inert gas. $GdCl_3$, $GaO_2$, or the like may be used instead of $GdF_3$. The same applies in the case of AlN:Gd. Another method is to dope diamond with gadolinium by injecting ions.

7 Porous Semiconductor Made up of Porous Silicon Nitride

As another favorable aspect, the inventors invented a porous material whose base material is porous silicon nitride ($Si_3N_4$) and that emits visible or ultraviolet light, and perfected a porous semiconductor in which this material is used as the porous semiconductor layer. Specifically, this is a porous semiconductor, comprising a porous substrate having continuous pores, and a porous semiconductor layer having a light emitting function that works by electroluminescence, cathode luminescence, or photoluminescence, and having continuous pores, wherein the porous semiconductor layer is made of porous silicon nitride composed of columnar $Si_3N_4$ particles with an average aspect ratio of at least 3 and an oxide-based binder phase containing at least one of rare earth element, and emits visible light or ultraviolet light.

Because it is constituted as above, the porous $Si_3N_4$ of the present invention offers the following advantages.

Ease of Pore Control

The pore size of the porous material of the present invention can be easily controlled because it is determined by the structure of the porous $Si_3N_4$ itself.

High Strength

The structure has high strength because the strength is determined by the structure of the porous $Si_3N_4$ itself.

High Permeation Performance

The permeation performance when the porous material is used as a filter is high because this performance is determined by the pore size and shape of the porous $Si_3N_4$.

Low Thermal Shock Resistance

Because the strength is high and the coefficient of thermal expansion of the porous $Si_3N_4$ is small, the thermal shock resistance is high.

With the present invention, it was discovered that if gadolinium, out of the many rare earth elements, is used as a sintering auxiliary in the production of the porous material by sintering columnar $Si_3N_4$ particles, an oxide-based binder phase itself will have the function of emitting ultraviolet light of 400 nm or less. $Si_3N_4$ dissolves and reprecipitates in the $SiO_2$-rare earth oxide-based liquid phase formed in the above-mentioned sintering process, part of the silicon and nitrogen remains in the liquid phase, so a compound based on Si—O—N-rare earth element is produced in the binder phase after the porous structure is formed. For instance, with a $Y_2O_3$ auxiliary system, $YSiO_2N$, $YNSiO_2$, $Y_2Si_2O_7$, $Y_2Si_3N_4O_3$, $Y_{4.67}(SiO_4)_3O$, $Y_8Si_4N_4O_{14}$, or the like is produced. Some of these are amorphous, and some are crystalline.

These oxides and acid nitrides have a large bandgap, and have potential as a matrix material for emitting ultraviolet light. When gadolinium is added to one of these materials and the product is irradiated with an electron beam or ultraviolet light with a wavelength of 300 nm or less as the excitation light source, for example, the energy had by these excitation light rays excites the electrons in the gadolinium ions directly or indirectly from a ground state to an excited state, and energy is released in the form of light in the transition back to a ground state. In general, the wavelength of light emitted from gadolinium ions is about 311 nm.

Porous $Si_3N_4$ can be produced as follows.

After the $Si_3N_4$ powder and an oxide of a rare earth element (used as a sintering auxiliary) are mixed in a specific composition, the mixture is molded and sintered in an inert gas. "Rare earth element" here refers to scandium, yttrium, and elements of atomic numbers 57 to 71. For instance, when $Gd_2O_3$ is used as an auxiliary, the $SiO_2$ present on the surface of the $Si_3N_4$ raw material and the $Gd_2O_3$ form a liquid phase at the sintering temperature, part of the $Si_3N_4$ dissolves in this, $Si_3N_4$ particles grow in columnar form during reprecipitation, and a porous structure is created. The liquid phase component solidifies in the cooling process, and is present as a binder phase on the surface of the $Si_3N_4$ particles or at the interface between $Si_3N_4$ particles. The binder phase is an Si—O—N—Gd-based oxide or oxynitride, and can be $GdSiO_2N$, $GdN-SiO_2$, $Gd_2Si_2O_7$, $Gd_2Si_3N_4O_3$, $Gd_{4.67}(SiO_4)_3O$, $Gd_8Si_4N_4O_{14}$, or the like. These are amorphous or crystalline. Light is emitted as a result of energy transition between the ground state and the excited state of the $4f$ or $5d$ orbital of gadolinium ions (the light emitting center) present in the compound serving as the matrix. When gadolinium is added, relatively inexpensive yttrium may be added at the same time (producing a $Gd_2O_3$—$Y_2O_3$ auxiliary). There will be a slight decrease in the luminous intensity of the ultraviolet light in this case.

The surface of the $Si_3N_4$ particles of the above-mentioned porous $Si_3N_4$ may be covered with particles or a film having a photocatalytic function. With this structure, the visible or ultraviolet light emitted from the fluorescent phase present on the surface of the $Si_3N_4$ particles or at the interface between the $Si_3N_4$ particles directly irradiates the photocatalyst, so the photocatalytic function can be obtained with extremely high efficiency.

The photocatalyst is generally a $TiO_2$-based material that exhibits its function when exposed to ultraviolet light, but photocatalysts that exhibit their function when exposed to visible light have also been developed in recent years. When a rare earth element other than gadolinium is added, visible light can generally be emitted, such as red ($Eu^{3+}$) or blue ($Eu^{2+}$) with europium, green with terbium or erbium, and blue with thulium, so if these elements are contained, a photocatalyst that functions with visible light should be used. However, a photocatalyst that exhibits its function when exposed to visible light does not function as a photocatalyst as well as a photocatalyst that exhibits its function when exposed to ultraviolet light. Also, when visible light is emitted, the porous $Si_3N_4$ itself can be used as various kinds of display-use fluorescent material.

In addition to decomposing organic matter, killing bacteria, and other such objectives, the photocatalytic function can also include an effect whereby the photocatalyst imparts a super-hydrophilic property. For instance, when a waste liquid whose main component is water is to be filtered with a porous $Si_3N_4$ filter, a filter having superior permeation performance can be used in order to lower resistance during passage through the filter.

Also, a deposited layer of particles or a film having a photocatalytic function may be formed on the surface of the porous $Si_3N_4$, rather than on the surface of the individual $Si_3N_4$ particles. In this case, the porous $Si_3N_4$ serving as the light emitting layer will be separate from the photocatalyst layer, so the extent to which the photocatalyst is irradiated with the emitted visible or ultraviolet light will be lower than when the surface of the individual $Si_3N_4$ particles are covered with the photocatalyst. Accordingly, this structure may be employed, but there will be a relative decrease in photocatalytic function.

The most favorable aspect of the present invention is to generate ultraviolet light by adding gadolinium. When gadolinium is added, ultraviolet light of 311 nm will be emitted most strongly, but the wavelength may sometimes shift to the longer side depending on the type of matrix species, the crystallinity, and so forth. In general, the higher is the crystallinity of the matrix semiconductor material, the sharper is the spectrum and the higher is the luminous intensity of the emission having a peak near 311 nm.

The average aspect ratio of the columnar grains of the porous $Si_3N_4$ thus produced is preferably at least 3. Below 3, the JIS three-point bending strength of the porous material will be less than 100 MPa, the thermal shock resistance will decrease, and the material will lose porosity during sintering, with the porosity dropping to less than 30% and permeation performance decreasing. The aspect ratio can basically be controlled by varying the ratio between the amount of $SiO_2$ on the raw material $Si_3N_4$ powder surface and the rare earth compound serving as the auxiliary, the amount of carbon-containing component used as a binder during powder mixing, the sintering temperature, and other such conditions. The sintering temperature is determined by the temperature at which a liquid phase appears. For example, with a $Y_2O_3$ auxiliary system, the liquid phase appearance temperature of a $SiO_2$—$Y_2O_3$ system is about 1750° C., so the amount of columnar $Si_3N_4$ particles produced can be increased by setting the temperature higher than this.

It is preferable for the amount of sintering auxiliary to be greater because the amount of binder phase present on the surface of the $Si_3N_4$ particles will increase and so will the luminous intensity, but if the amount of auxiliary is too large, no columnar $Si_3N_4$ particles will be produced. The suitable amount of sintering auxiliary is about 4 to 15 wt % with respect to the $Si_3N_4$ powder. Below this range it will be difficult to produce columnar $Si_3N_4$ particles.

The aspect ratio tends to increase at a high sintering temperature or with a composition rich in rare earth compound. When the carbon content is high, the $SiO_2$ on the $Si_3N_4$ surface is reduced by the carbon, which results in a composition that is richer in rare earth compound and a higher aspect ratio. α-type $Si_3N_4$ powder is usually used as the raw material, but a β-type may be used instead. The α-type dissolves in the liquid phase more readily, so columnar particles tend to grow better and result in a higher aspect ratio.

The larger is the particle size of the raw material powder, the coarser are the columnar grains and the greater their pore size. To obtain a porous material with a sharp pore size distribution, it is preferable to use α-type $Si_3N_4$ powder, which has a smaller particle size distribution at submicron size. The average pore size of the porous $Si_3N_4$ produced here is preferably about 0.1 to 5 μm. To further increase the pore size, a tiny amount of an element that will promote particle growth, such as iron, may be added to the auxiliary.

The porous $Si_3N_4$ of the present invention has the function of emitting ultraviolet light under application of AC voltage, for example, so when it is used as a filter combined with a photocatalyst, the result is a ceramic filter having a novel function in which the permeation performance is high, treatment capability is excellent, strength and thermal shock resistance are both high, resulting in higher reliability, and sterilization and organic matter decomposition can be carried out simultaneously. Particularly in the filtration of an aqueous liquid such as wastewater, the filter will be super-hydrophilic, which affords even higher permeation performance.

Also, ultraviolet light can be generated when neodymium or thulium is used as the rare earth element in the porous silicon nitride of the present invention, for example, and visible light can be generated when yttrium, europium, or Terbium is used. In this case the product can be used as a lightweight, high-strength, highly reliable fluorescent material. A porous material may also be made from SiAlON, which is $Si_3N_4$ that contains aluminum and oxygen.

BEST MODE FOR CARRYING OUT THE INVENTION

The present invention will now be described further through examples, but is not limited to or by these examples.

EXAMPLE 1

A substrate was produced by sputtering a 50 Å coating of gold onto a porous plate of SUS316 with a diameter of 25 mm and a thickness of 1 mm. The substrate had a porosity of 50% and a pore size of 10 μm diameter. A mixture of graphite powder and ZnO powder with an average particle size of 1 μm diameter was placed in an aluminum boat, and this was inserted along with the substrate into a tube furnace held at a temperature of 925° C. under an argon gas flow at atmospheric pressure, and heated for 30 minutes. The raw material powder was placed at the center of the furnace tube, while the substrate was placed downstream from the center where the temperature was kept somewhat lower.

Whiskers were produced on the surface of the heated substrate. X-ray analysis revealed the whiskers to be ZnO. The following Samples 1 and 2 were produced from the obtained sample.

Sample 1: An electrode was formed on the substrate surface and the surface of the whiskers of the sample.

Sample 2: Titanium isopropoxide $(Ti(OC_2H_5)_4)$, which is an alkoxide reagent of titanium, was dissolved in ethanol to prepare a solution. This solution was sprayed onto the surface of the ZnO whiskers of the sample, after which this product was heated for 1 hour at a temperature of 500° C. in the air to coat the ZnO surface with $TiO_2$. An electrode was then formed on the substrate surface and the surface of the whiskers. The above Samples 1 and 2 were evaluated as follows.

① Evaluation of Light Emission Characteristics

Figure 8:
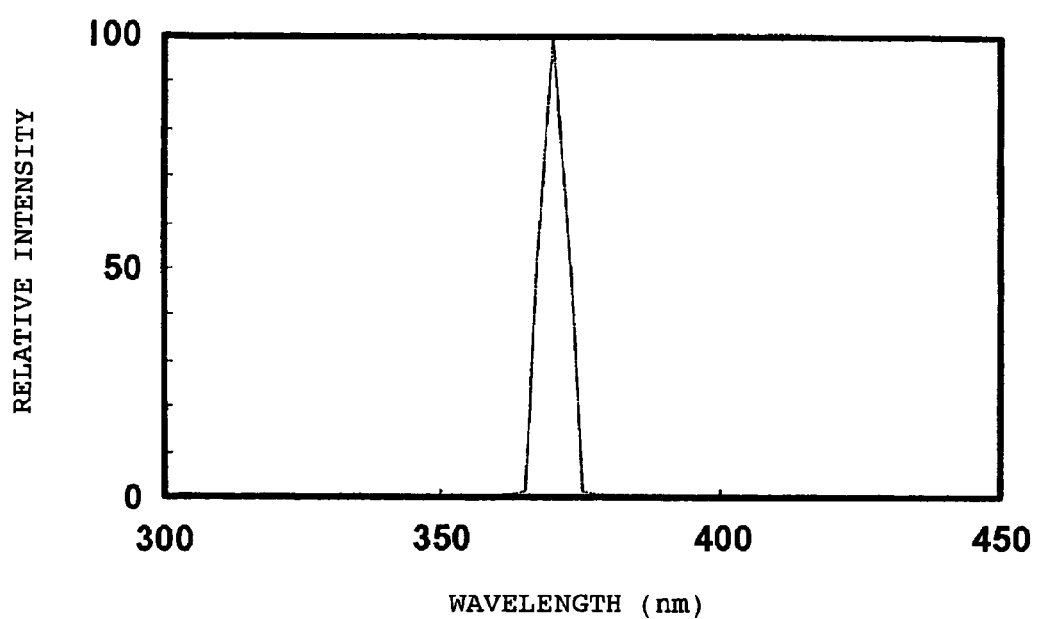
FIG. 8 is a graph of the emission spectrum of the porous semiconductor obtained in Example 1.

Current was applied to Sample 1, and the light emission wavelength and intensity were measured. These results are shown in FIG. 8. As shown in the graph, only emission at a wavelength of 370 nm, which corresponds to the band end wavelength of ZnO, was confirmed.

② Evaluation of Filtration Characteristics

As shown in FIG. 9(a), an SUS holder was filled with Sample 2. Meanwhile, diesel particulate (DP) with an average particle size of 5 μm was sprayed into the tank shown in FIG. 9(b), which had a volume of 10 liters, to produce a gas with a concentration of 100 ppm. The SUS holder of FIG. 9(a) charged with the sample was linked to the tank as shown in FIG. 9(b). While voltage was applied to Sample 2, gas was supplied from the whisker side of Sample 2, and circulating filtration was performed for 2 hours. The DP concentration in the tank was measured after 2 hours and found to be zero. Furthermore, substantially no DP was present on the ZnO surface. However, when circulating filtration was performed without applying voltage, the DP concentration after 2 hours did not drop to zero, instead stopping at 30 ppm, and a large amount of DP was present on the ZnO surface.

It can be seen from the above results that when voltage was applied, ultraviolet light with a wavelength of 370 nm was emitted, the $TiO_2$ photocatalyst absorbed this ultraviolet light, and the DP was decomposed by the photocatalytic action. The reason that the concentration decreased to 30 ppm when no voltage was applied is understood to be that part of the DP was trapped in the ZnO whisker layer.

EXAMPLE 2

Figure 1:
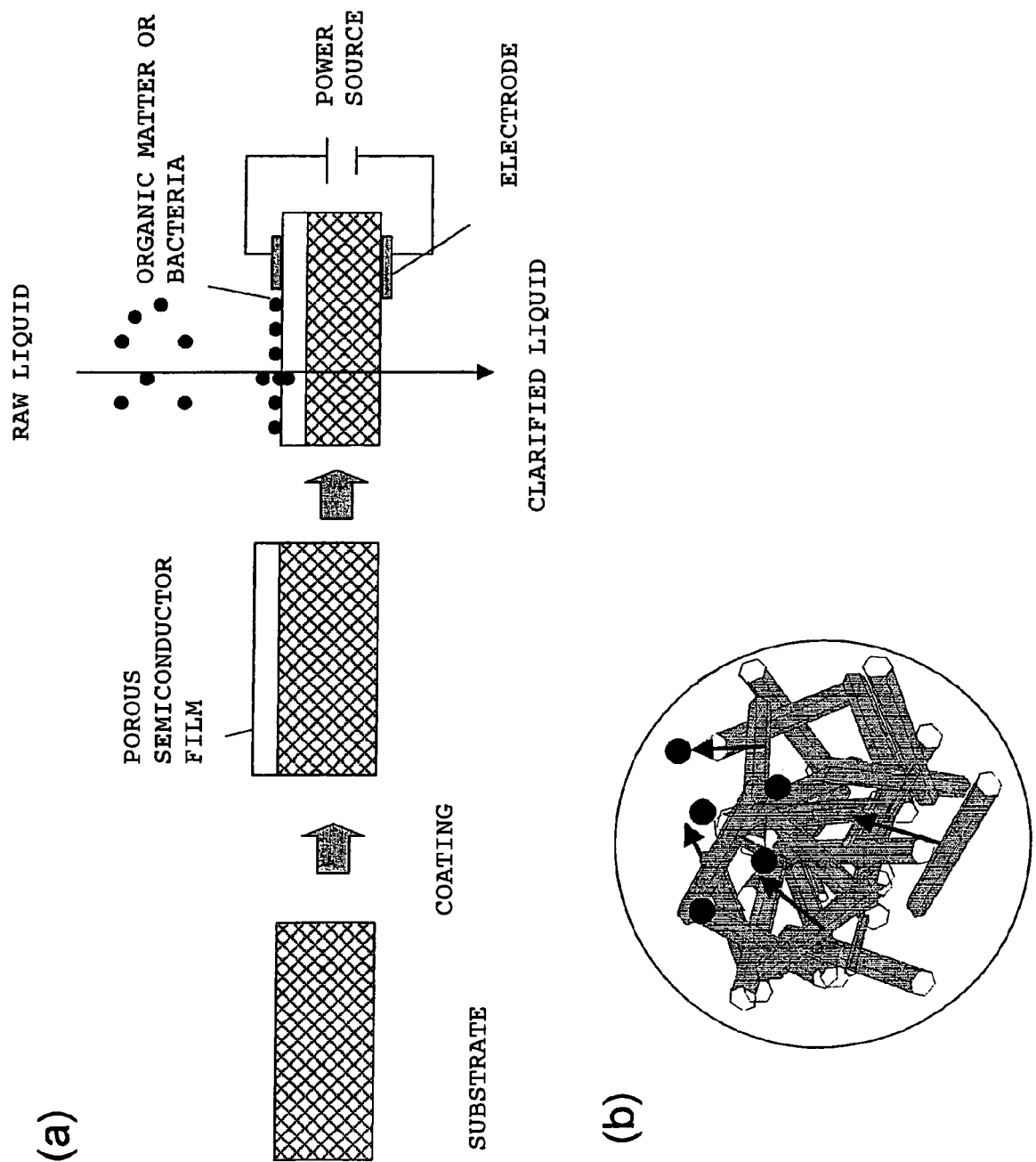
FIG. 1 is a schematic diagram illustrating the structure and action of the filter of the present invention.
Figure 2:
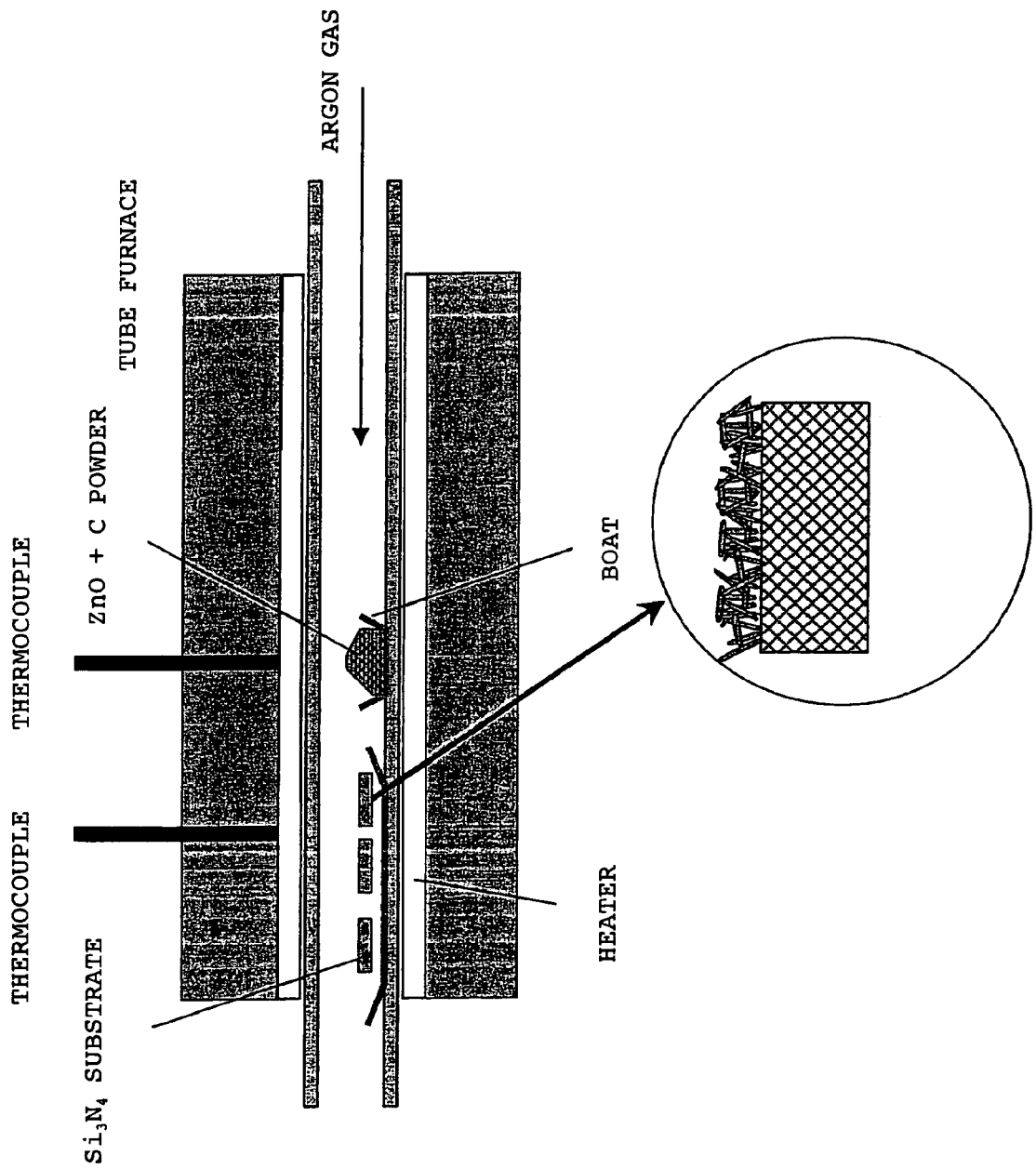
FIG. 2 is a simplified diagram of the apparatus used to obtain the filter of the present invention by chemical transport.
Figure 3:
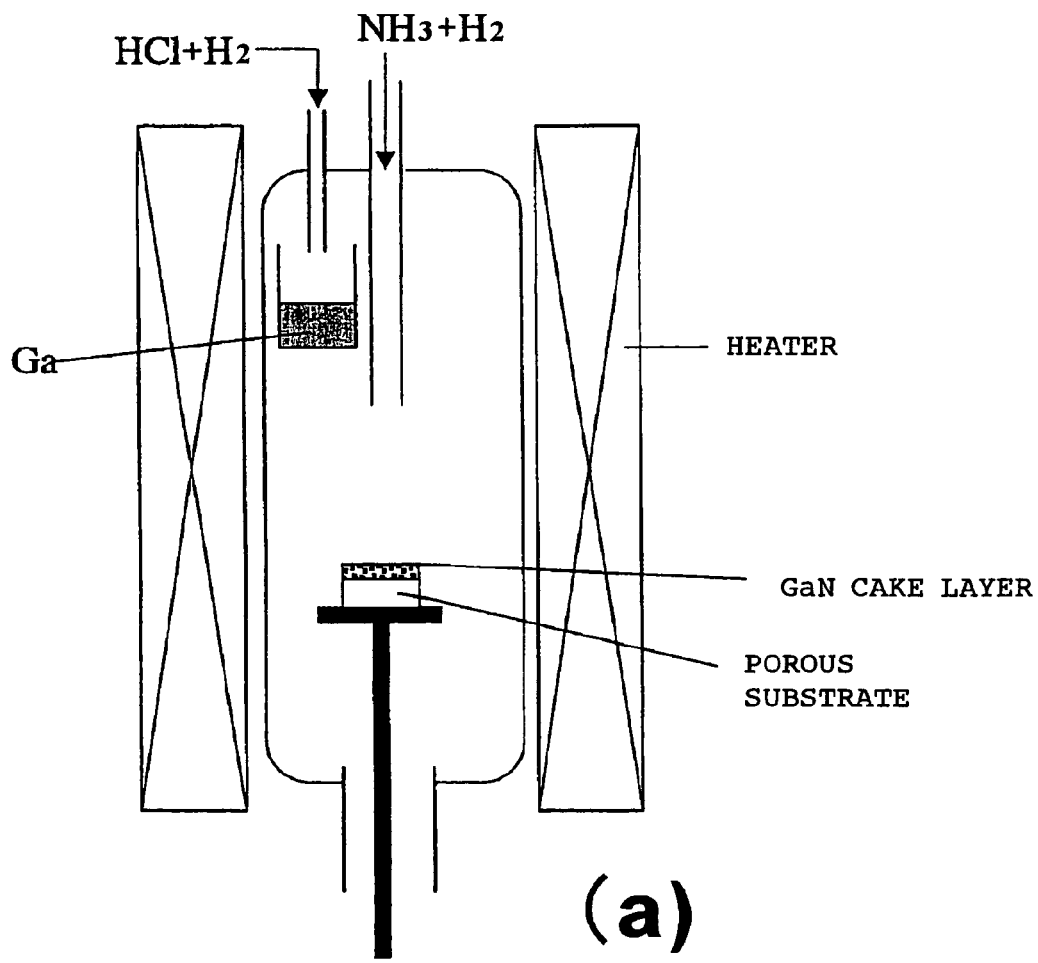
FIG. 3 is a simplified diagram of the apparatus used to obtain the filter of the present invention by CVD.
Figure 3:
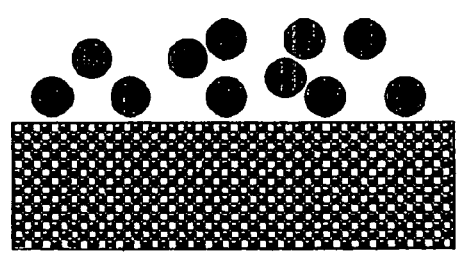
Figure 3:
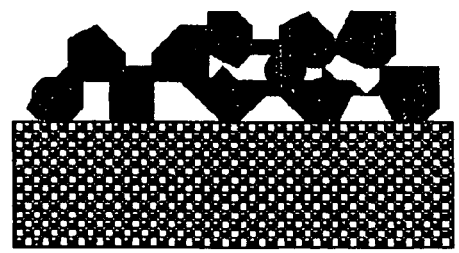
Figure 4:
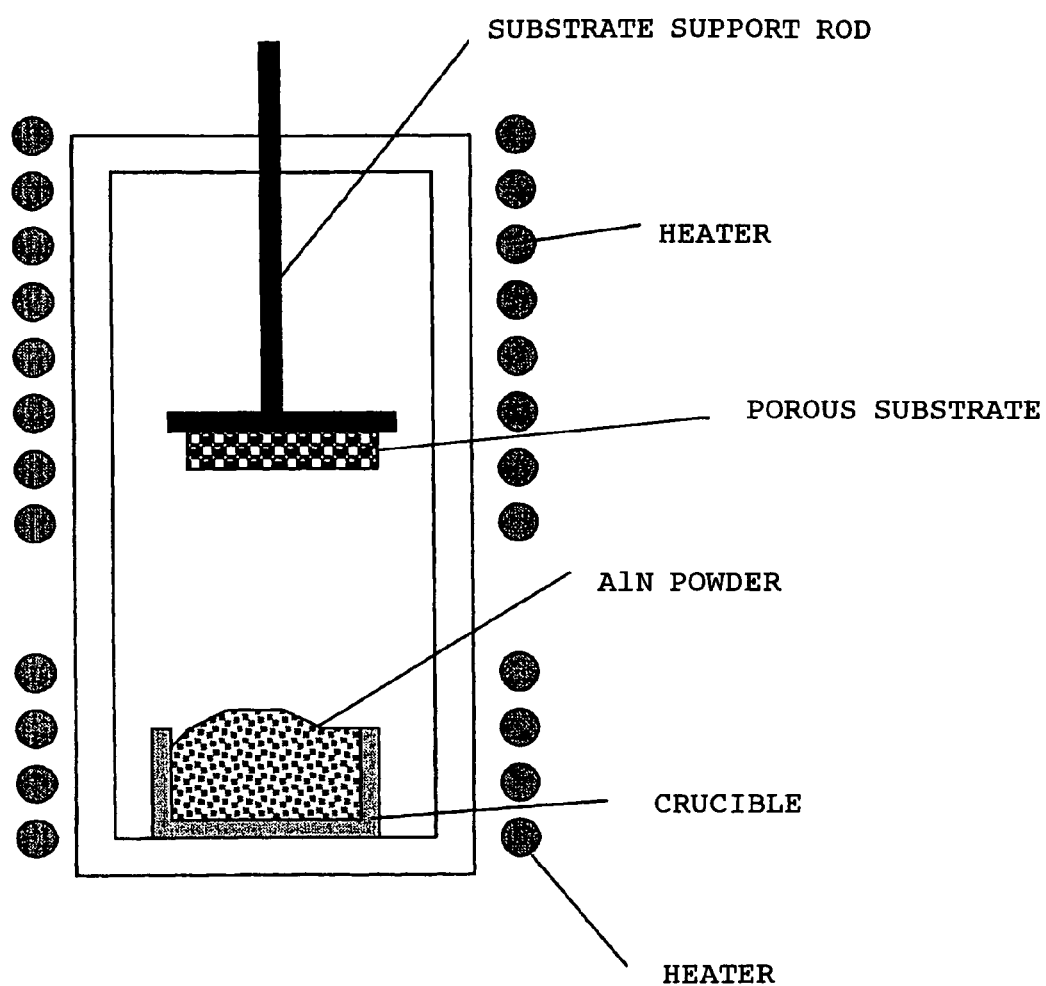
FIG. 4 is a simplified diagram of the apparatus used to obtain the filter of the present invention by sublimation.
Figure 5:
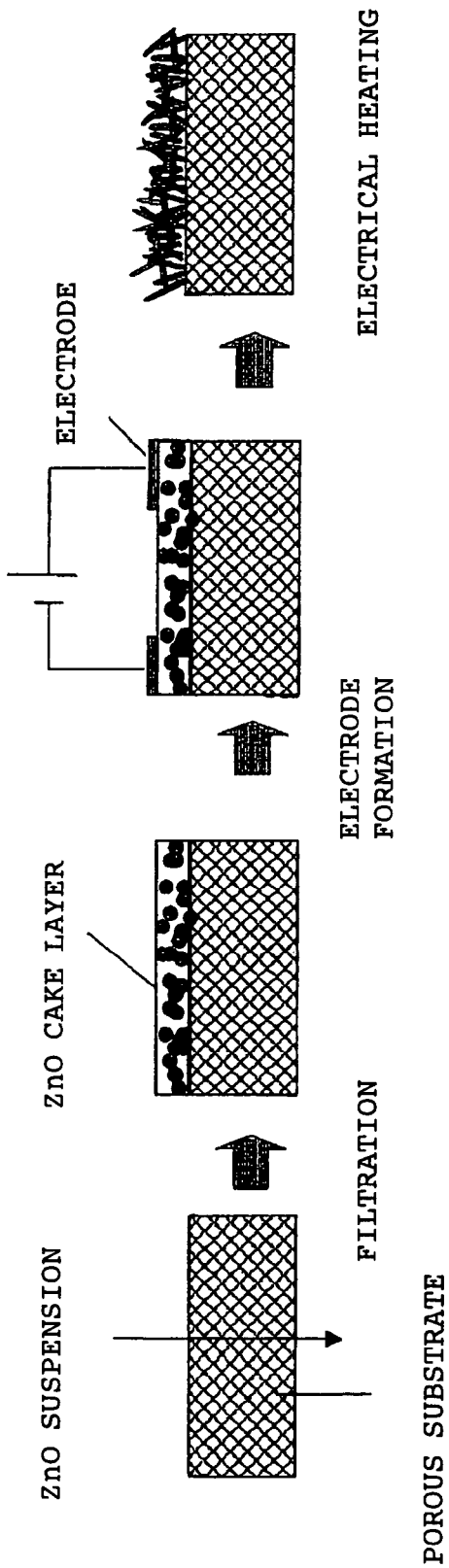
FIG. 5 is a simplified diagram of the apparatus used to obtain the filter of the present invention by electrical heating.
Figure 6:
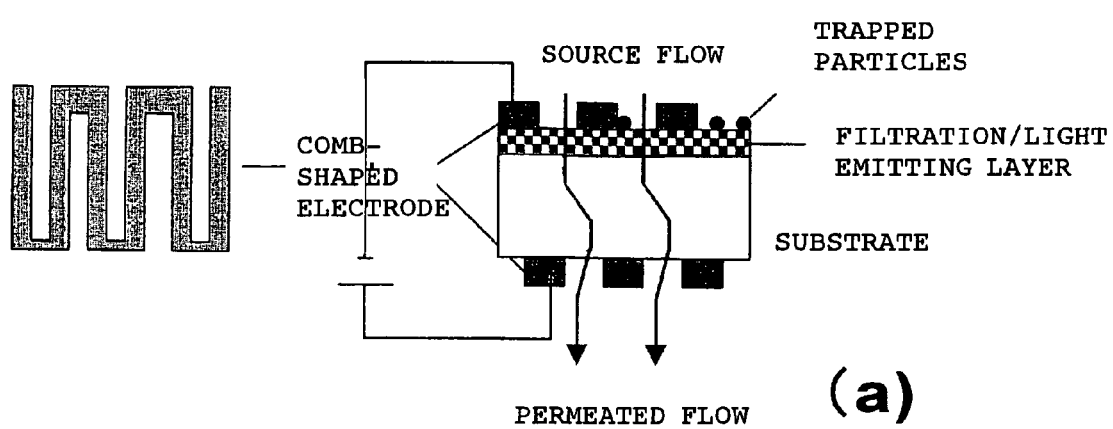
FIG. 6 is a schematic diagram illustrating the structure and action when an electrode has been attached to the filter of the present invention.
Figure 6:
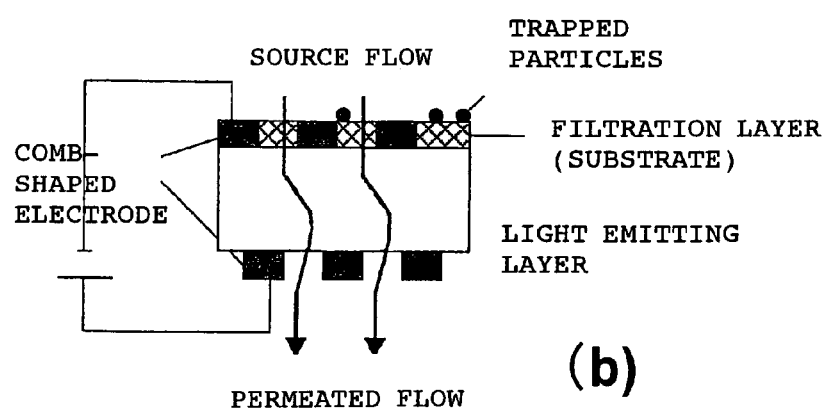
Figure 7:
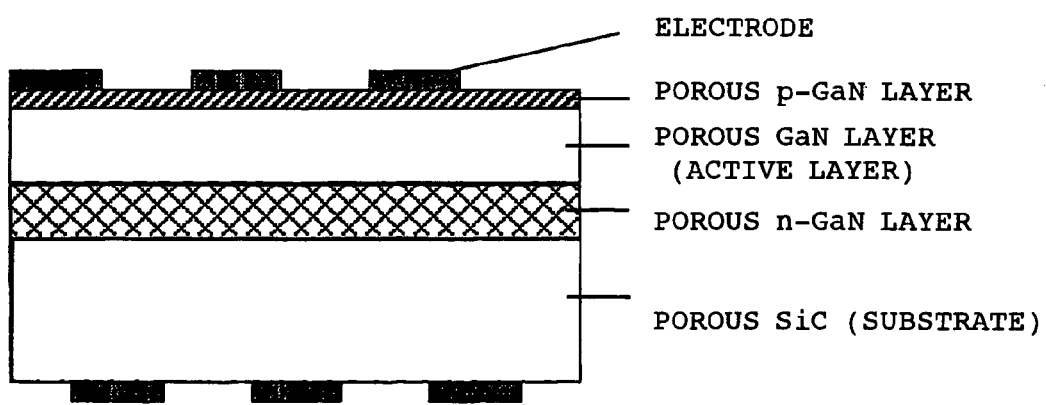
FIG. 7 is a schematic diagram illustrating the structure of the filter of the present invention having a pn junction.
Figure 7:
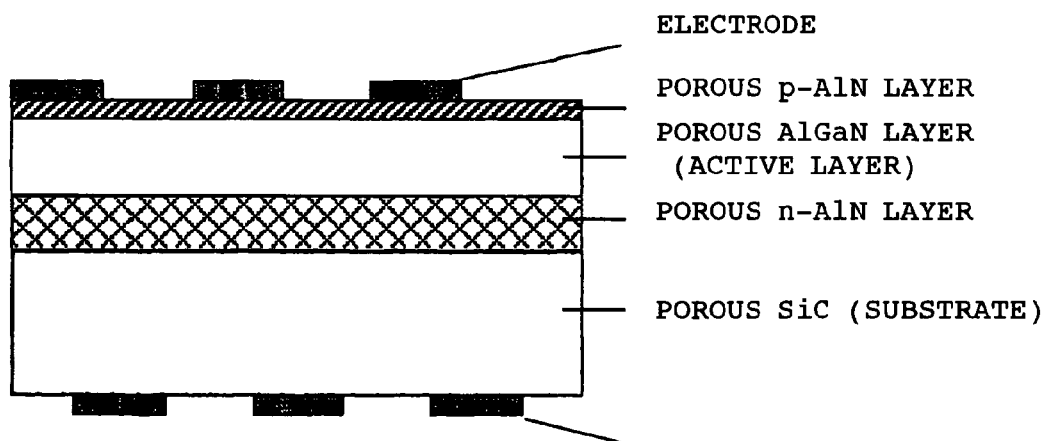

Porous SiC with a diameter of 25 mm and a thickness of 1 mm was used as the substrate. The porosity was 50% and the pore size was 10 μm. As shown in FIG. 4, AlN powder (with a purity of 99.99%, containing 0.01% magnesium as an impurity) packed in a crucible and a porous SiC substrate were placed a super-high-temperature furnace. The pressure inside the furnace was lowered to close to a vacuum, after which the raw material area was heated to between 2000 and 2200° C., and the substrate area to 1900° C. $N_2$ was then introduced and the pressure inside the furnace was held at 40 kPa. This state was maintained for 2 hours, after which the system was cooled to room temperature.

Whiskers were produced on the surface of the heated substrate. X-ray analysis revealed the whiskers to be AlN. The product of forming an electrode on the substrate surface and the surface of the whiskers of the sample obtained when the temperature in the raw material area was 2200° C. was termed "Sample 3," and the product of forming an electrode on the sample obtained when the temperature in the raw material area was 2000° C. was termed "Sample 4." These Samples 3 and 4 were evaluated as follows.

① Evaluation of Light Emission Characteristics

Figure 10:
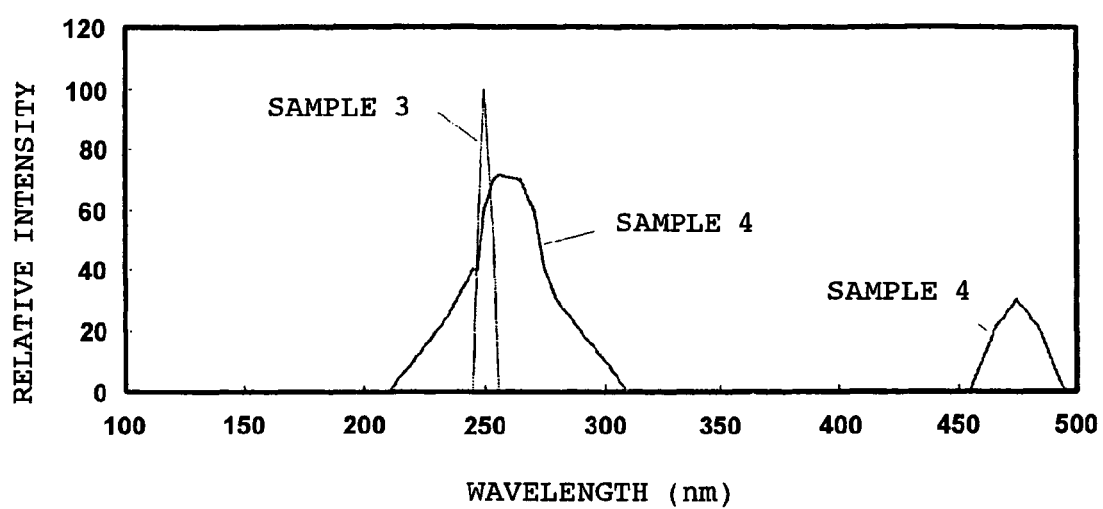
FIG. 10 is a graph of the emission spectrum of the porous semiconductor obtained in Example 2.

Current was applied to Samples 3 and 4, and the light emission wavelength and strength were measured. These results are shown in FIG. 10.

It was confirmed that Sample 3 was AlN whiskers with extremely high crystallinity, and that only light with a wavelength of 254 nm, which is close to the band end wavelength of 200 nm of AlN, was emitted. With Sample 4, light was emitted not only at 254 nm, but also near 470 nm, which seemed to indicate that the crystallinity was somewhat poor and that light was also being emitted from a deep level thought to originate in crystal defects.

② Evaluation of Filtration Characteristics

Figure 9:
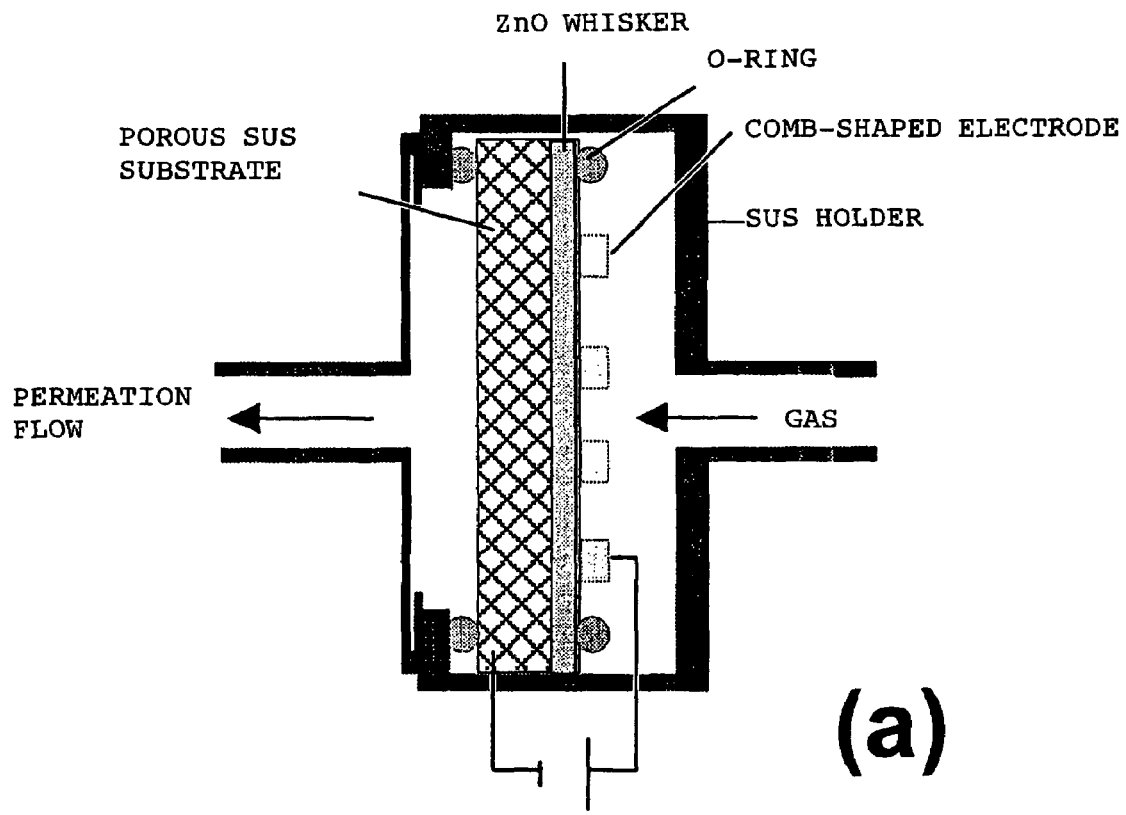
FIG. 9 is a simplified diagram of the apparatus used in the evaluation tests.
Figure 9:
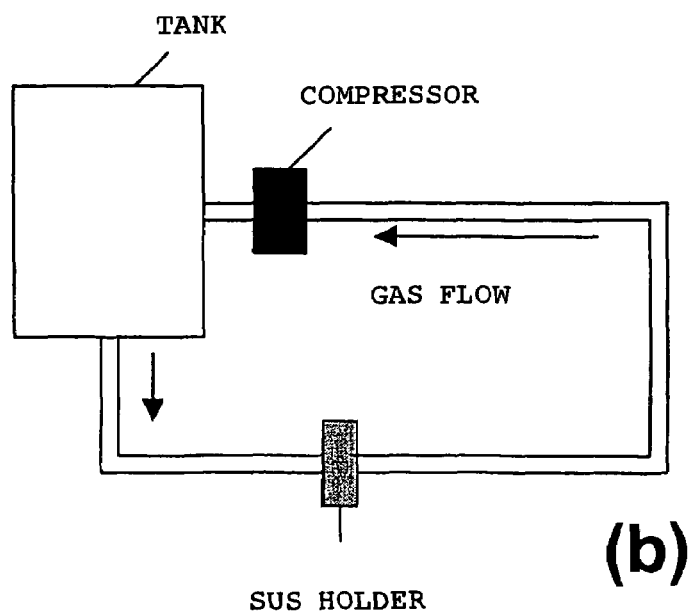

*E. coli* (average size of 0.5 μm) were sprayed into the tank shown in FIG. 9(*b*), which had a volume of 10 liters, to produce a gas with a concentration of 100 ppm. The SUS holder of FIG. 9(*a*) charged with the sample was linked to the tank as shown in FIG. 9(*b*). While voltage was applied to Samples 3 and 4, gas was supplied from the whisker side of the sample, and circulating filtration was performed for 5 hours. The *E. coli* concentration in the tank was measured after 5 hours and found to be zero with Sample 3, but 5 ppm with Sample 4. Numerous dead *E. coli* were also present on the AlN whisker layer surface of Samples 3 and 4. Thus it can be seen that the higher is the luminous intensity of 254 nm, the better is the sterilization effect.

Meanwhile, when circulating filtration was performed without applying any voltage, the *E. coli* concentration did not decrease greatly, remaining at 50 ppm, and a large quantity of live *E. coli* were present on the AlN surface of Sample 4. The above results tell us that the *E. coli* in the gas were trapped in the AlN whisker layer by circulating filtration, but when no voltage was applied, although the concentration did decrease to 50 ppm, live *E. coli* remained on the AlN whisker layer surface. It is believed that when voltage was applied, ultraviolet light with a wavelength of 254 nm was generated and directly destroyed the DNA of the *E. coli,* wiping out the bacteria.

EXAMPLE 3

Figure 11:
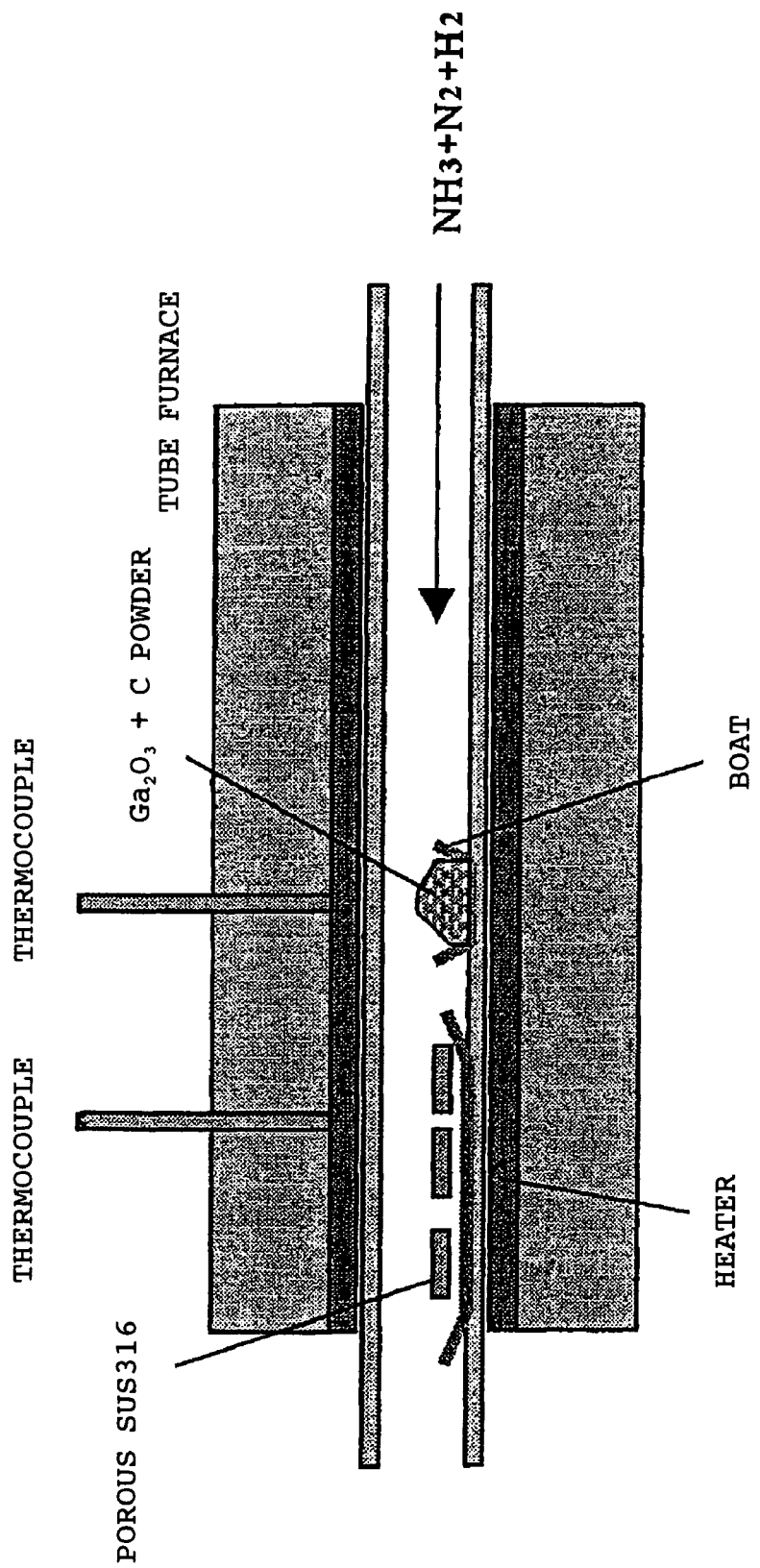
FIG. 11 is a simplified diagram of the apparatus used to manufacture the GaN porous semiconductor in Example 3.

Porous SUS316 with a diameter of 25 mm and a thickness of 1 mm was used as the substrate. The porosity was 40% and the pore size was 3 μm. As shown in FIG. 11, a mixture of graphite powder and $Ga_2O_3$ powder with an average particle size of 1 μm was placed in an aluminum boat, and this was inserted along with the substrate into a tube furnace held at a temperature of 900° C. under an $NH_3$—$N_2$—$H_2$ gas flow, and heated for 1 hour. The raw material powder was placed at the center of the furnace tube, while the substrate was placed downstream where the temperature was kept at 650° C., which is lower than that of the center. Whiskers were produced on the surface of the heated substrate. X-ray analysis revealed the whiskers to be GaN.

The following Samples 5 and 6 were produced from the obtained sample.

Sample 5: An electrode was formed on the substrate surface and the surface of the whiskers of the sample.

Sample 6: Titanium isopropoxide ($Ti(OC_2H_5)_4$), which is an alkoxide reagent of titanium, was dissolved in ethanol to prepare a solution. This solution was sprayed onto the surface of the GaN whiskers of the sample, after which this product was heated for 1 hour at a temperature of 500° C. in the air to coat the GaN surface with $TiO_2$. An electrode was then formed on the substrate surface and the surface of the whiskers. The above Samples 5 and 6 were evaluated as follows.

① Evaluation of Light Emission Characteristics

Figure 12:
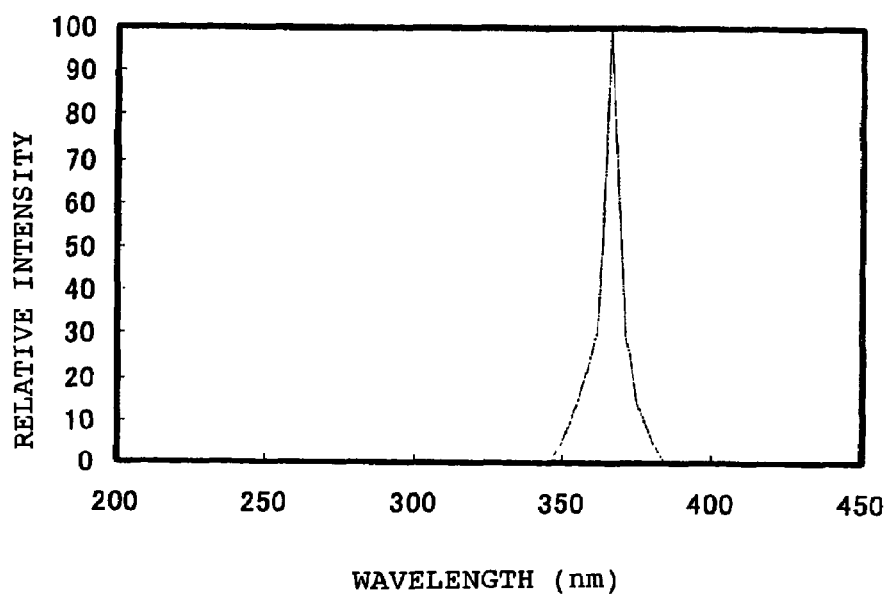
FIG. 12 is a graph of the emission spectrum of the GaN porous semiconductor obtained in Example 3.
Figure 13:
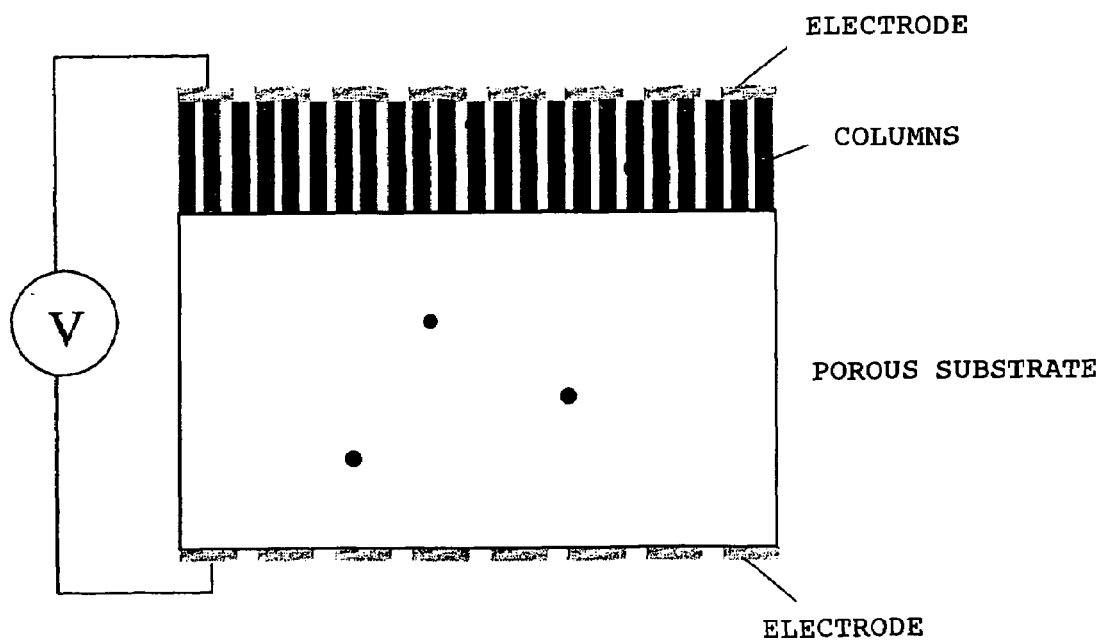
FIG. 13 is a diagram illustrating an example of the basic conceptual structure of the porous semiconductor of the present invention.
Figure 14:
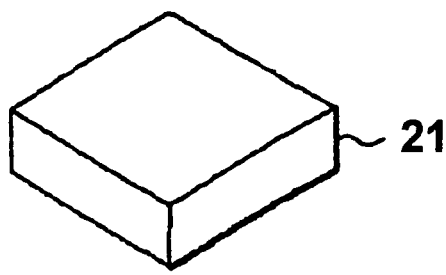
FIG. 14 illustrates the steps involved in the process of producing diamond in columnar form.
Figure 14:
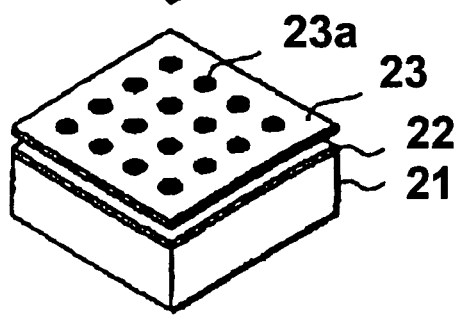
Figure 14:
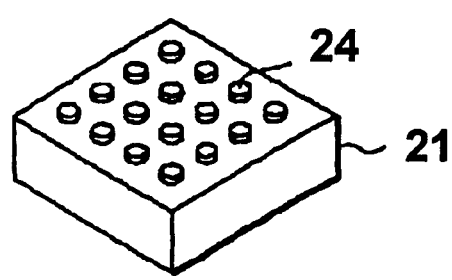
Figure 14:
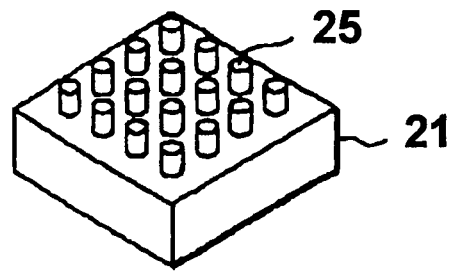
Figure 14:
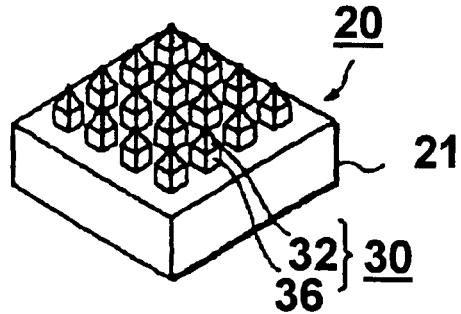
Figure 15:
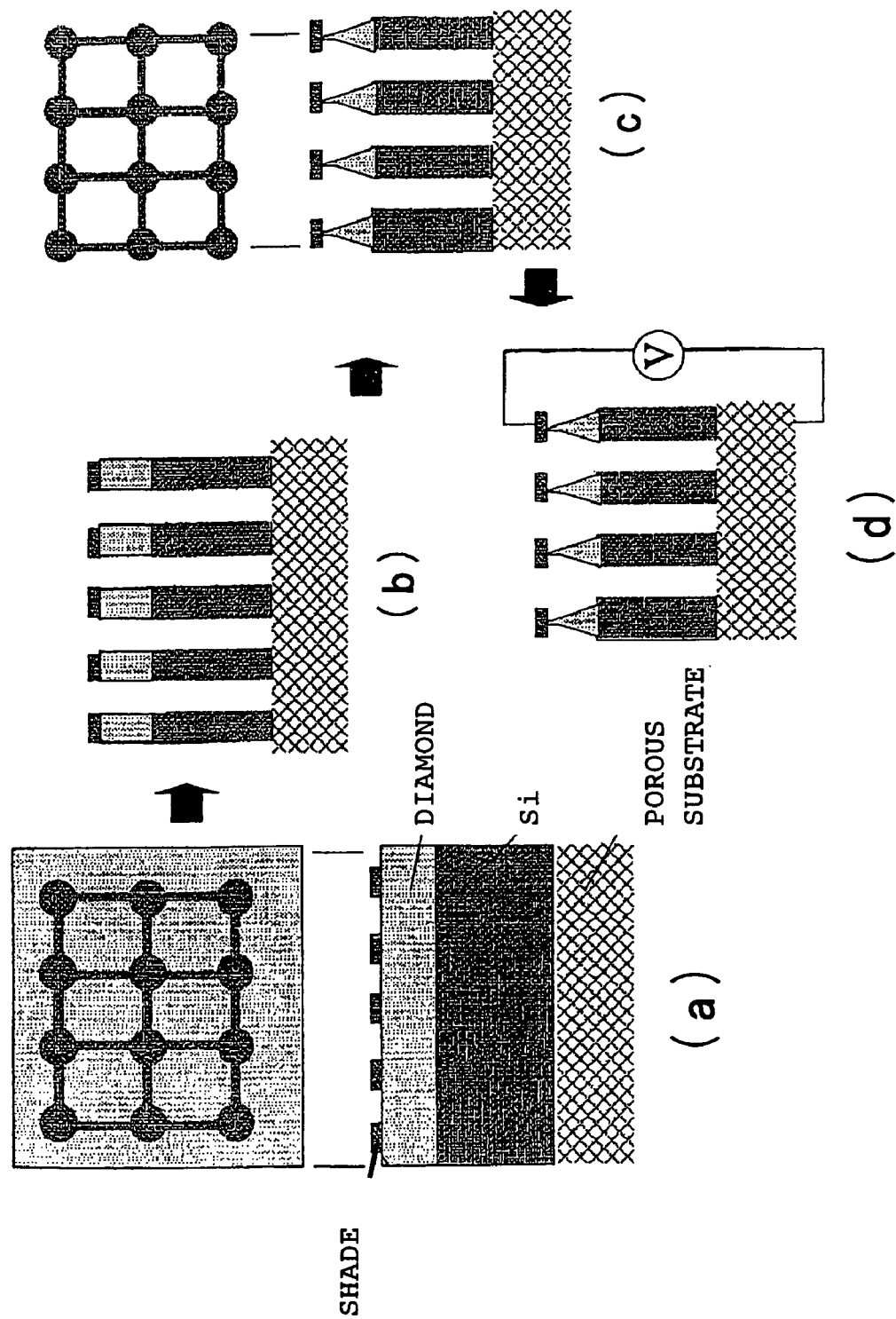
FIG. 15 illustrates the steps involved in the process of manufacturing a porous semiconductor in which the columns are diamond.
Figure 16:
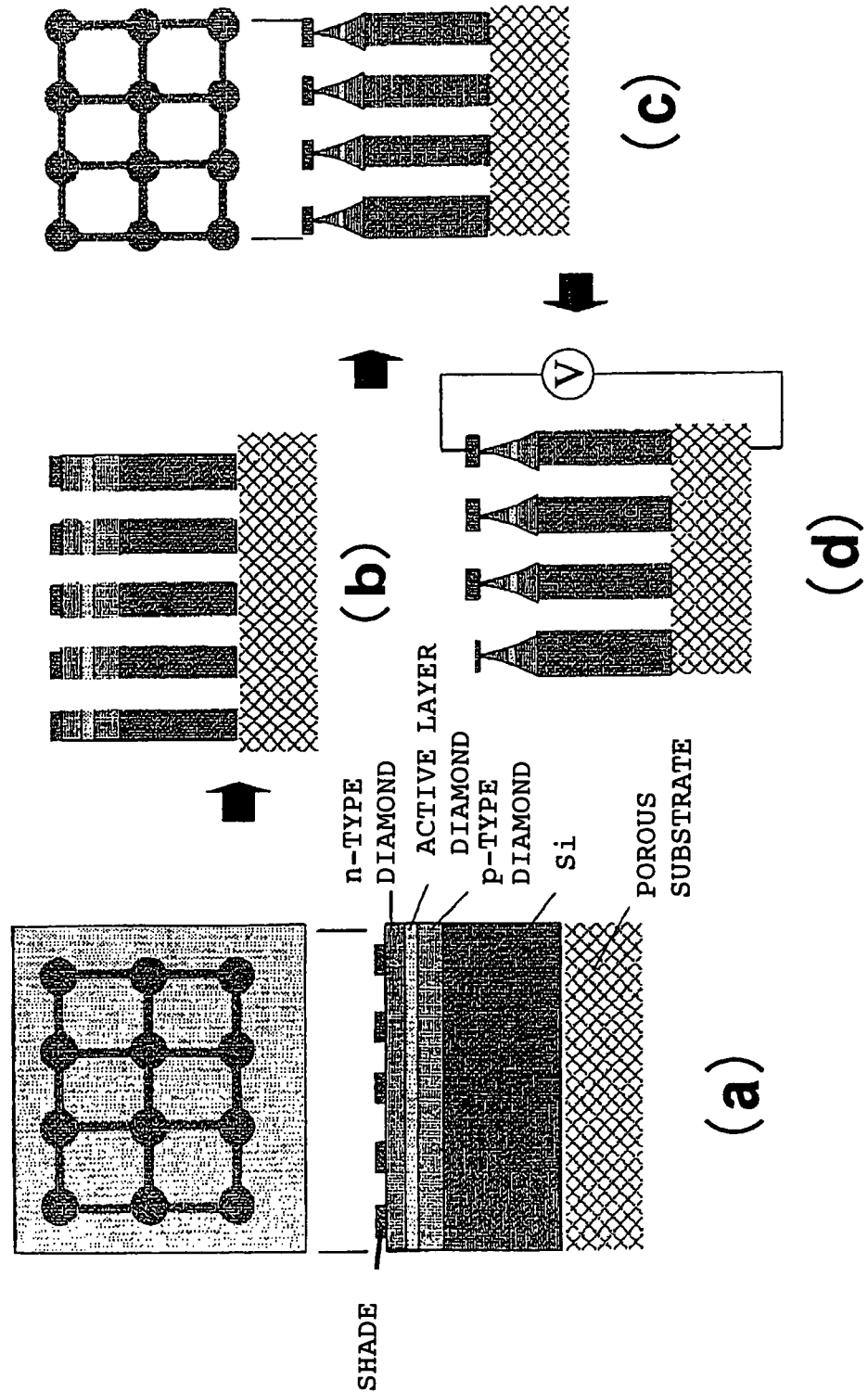
FIG. 16 illustrates the steps involved in the process of manufacturing a porous semiconductor in which the columns are diamond formed with a pn junction.

Current was applied to Sample 5, and the light emission wavelength and intensity were measured. These results are shown in FIG. 12. As shown in the graph, only emission at a wavelength of 367 nm, which corresponds to the band end wavelength of GaN, was confirmed.

② Evaluation of Filtration Characteristics

NOx gas was sprayed into the tank shown in FIG. 9(*b*), which had a volume of 10 liters, to produce a gas with a concentration of 100 ppm. Meanwhile, Sample 4 was charged into the SUS holder shown in FIG. 9(*a*). The SUS holder of FIG. 9(*a*) charged with the sample was linked to the tank as shown in FIG. 9(*b*). While voltage was applied, gas was supplied from the whisker side of the sample, and circulating filtration was performed for 2 hours. The NOx concentration in the tank was measured after 2 hours and found to be zero. On the other hand, when circulating filtration was performed without applying voltage, the NOx concentration after 2 hours remained unchanged at 100 ppm.

It can be seen from the above results that when voltage was applied, ultraviolet light with a wavelength of 367 nm was emitted, the $TiO_2$ photocatalyst absorbed this ultraviolet light, and the DP was decomposed by the photocatalytic action.

EXAMPLE 4

This is an example in which diamond was used in the form of columns, and corresponds to a porous semiconductor layer made up of columns.

First, a silicon substrate with a thickness of 8 μm was readied by pre-joining it to a porous stainless steel substrate having a porosity of 50% and an average pore size of 0.2 μm, and monocrystalline diamond was grown on the (100) plane thereof. Phosphorus or boron was used as a dopant. A mask was formed two-dimensionally on this (100) substrate by photolithography, comprising tiny disks of aluminum with a diameter of 3 μm and fine wires with a width of 0.5 μm that linked these disks. The disk pitch was 5 μm. The diamond film was structured such that an n-type layer was formed in a thickness of 2 μm over silicon, and a p-type layer with a thickness of 2 μm was formed over this.

Next, the substrate was subjected to reactive ion etching for 4 hours at 5.3 Pa and 220 W in a gas with a composition of $CF_4$ (mol)/$O_2$ (mol)=0.002, which formed circular columns with a diameter of 3 μm and a height of 12 μm.

Figure 17:
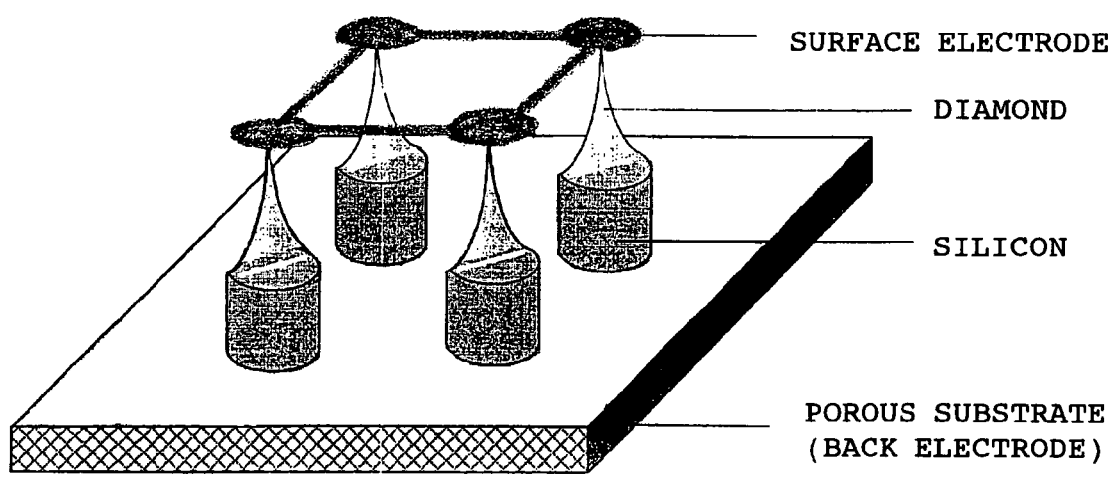
FIG. 17 is a diagram illustrating the structure of the porous semiconductor produced in Example 4.
Figure 18:
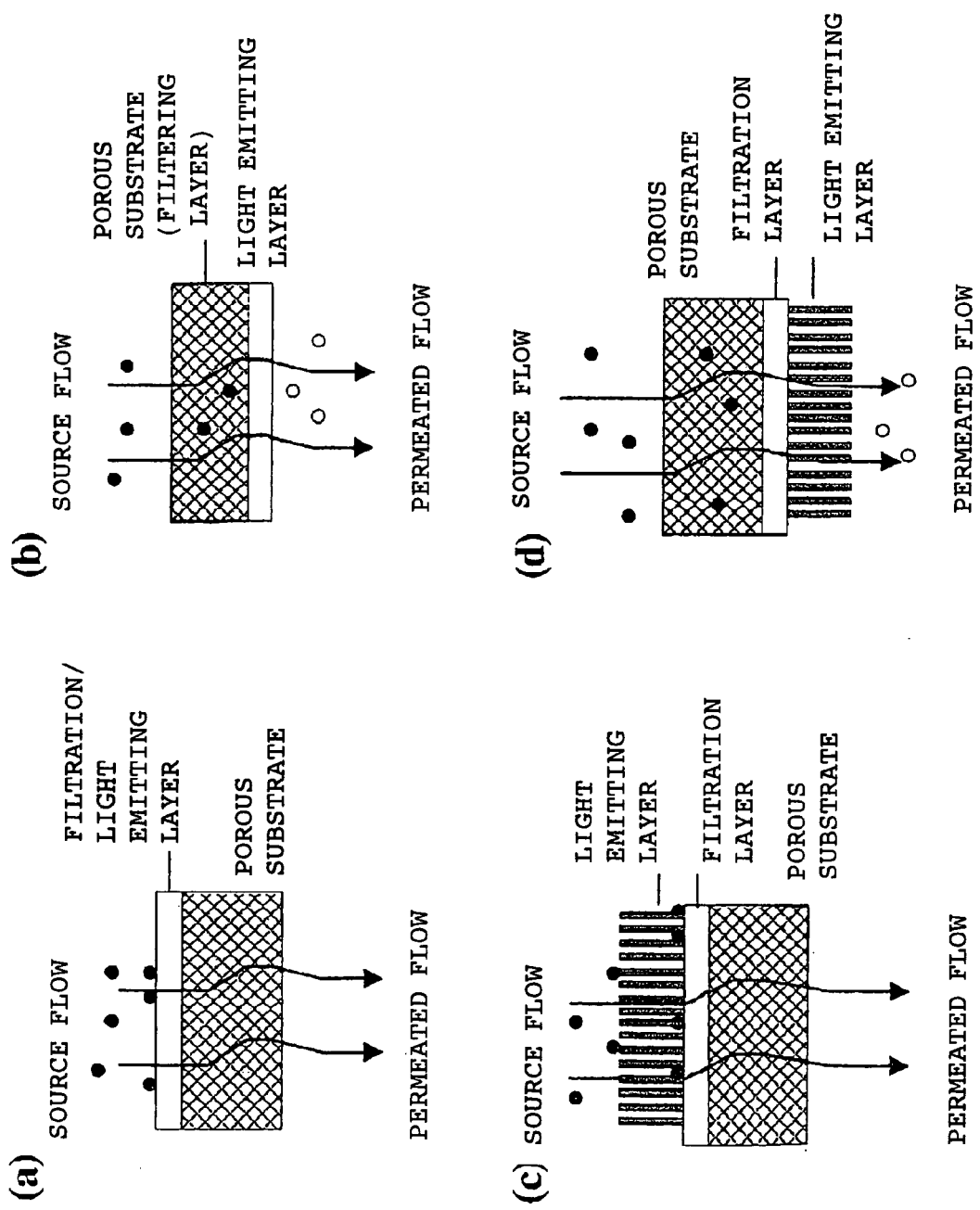
FIG. 18 is a diagram illustrating a usage mode of the porous semiconductor of the present invention.

After the formation of these columns, they were subjected to plasma etching for 5 hours at a substrate temperature of approximately 1045° C., a pressure of 13.3 kPa, and a microwave power of 440 W in a gas with a composition of $CO_2$ (mol)/$H_2$ (mol)=0.005. As a result, the porous semiconductor shown in FIG. 17 was obtained, in which the structure comprised a stand of columns in the planar orientation of the diamond, each having a portion at which its shape depends on the planer orientation of the diamond, and a pointed component located at the distal end of this portion. The diameter of the diamond columns was 3 μm, the height was 12 μm, the pitch was 5 μm, and the diameter at the tip of the pointed component was 0.5 μm. A mesh-like aluminum electrode remained on the surface of the diamond columns. The porous semiconductors produced above were evaluated as follows.

Figure 19:
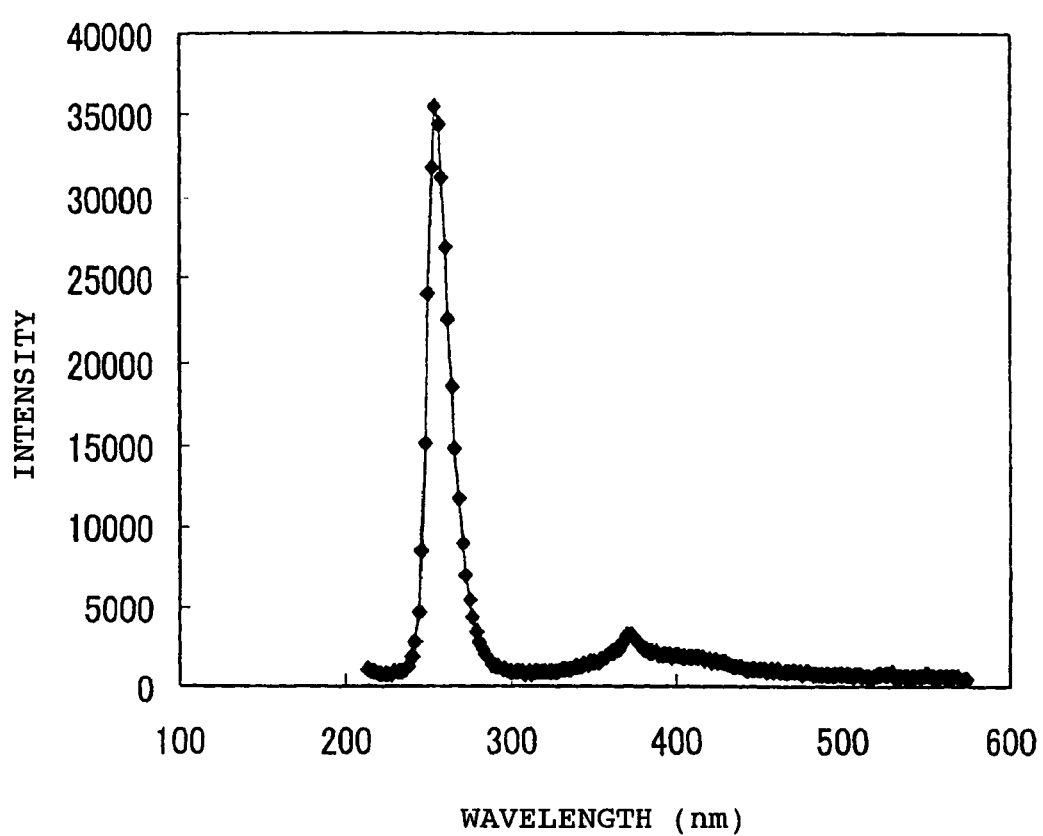
FIG. 19 is a graph of the emission spectrum of the porous semiconductor produced in Example 4.

① Voltage was applied and the emission wavelength and intensity were measured. The results are given in FIG. 19. A spectrum having a light emitting center at 254 nm was obtained.

② *E. coli* (average size of 0.5 μm) were sprayed into an air cylinder with a volume of 10 liters to produce a gas with a concentration of 100 ppm, and while voltage was applied, the gas was supplied from the column side of the porous semiconductor, and circulating filtration was performed for 5 hours. The *E. coli* concentration in the tank was measured after 5 hours. For the sake of comparison, the same filtration was also performed without applying any voltage.

As a result, the *E. coli* concentration was zero when voltage was applied. Numerous dead *E. coli* were present on the porous substrate surface. On the other hand, when no voltage was applied, the *E. coli* concentration did not decrease greatly, remaining at 50 ppm, and a large quantity of live *E. coli* were present on the porous substrate surface.

The above results tell us that the *E. coli* in the gas were trapped on the porous substrate surface by circulating filtration, but when no voltage was applied, although the concentration did decrease to 50 ppm, live *E. coli* remained on the porous substrate surface. It is believed that when voltage was applied, ultraviolet light with a wavelength of 254 nm was generated and directly destroyed the DNA of the *E. coli*, wiping out the bacteria.

EXAMPLE 5

This is an example in which the porous semiconductor layer corresponds to columns of ZnO.

Figure 20:
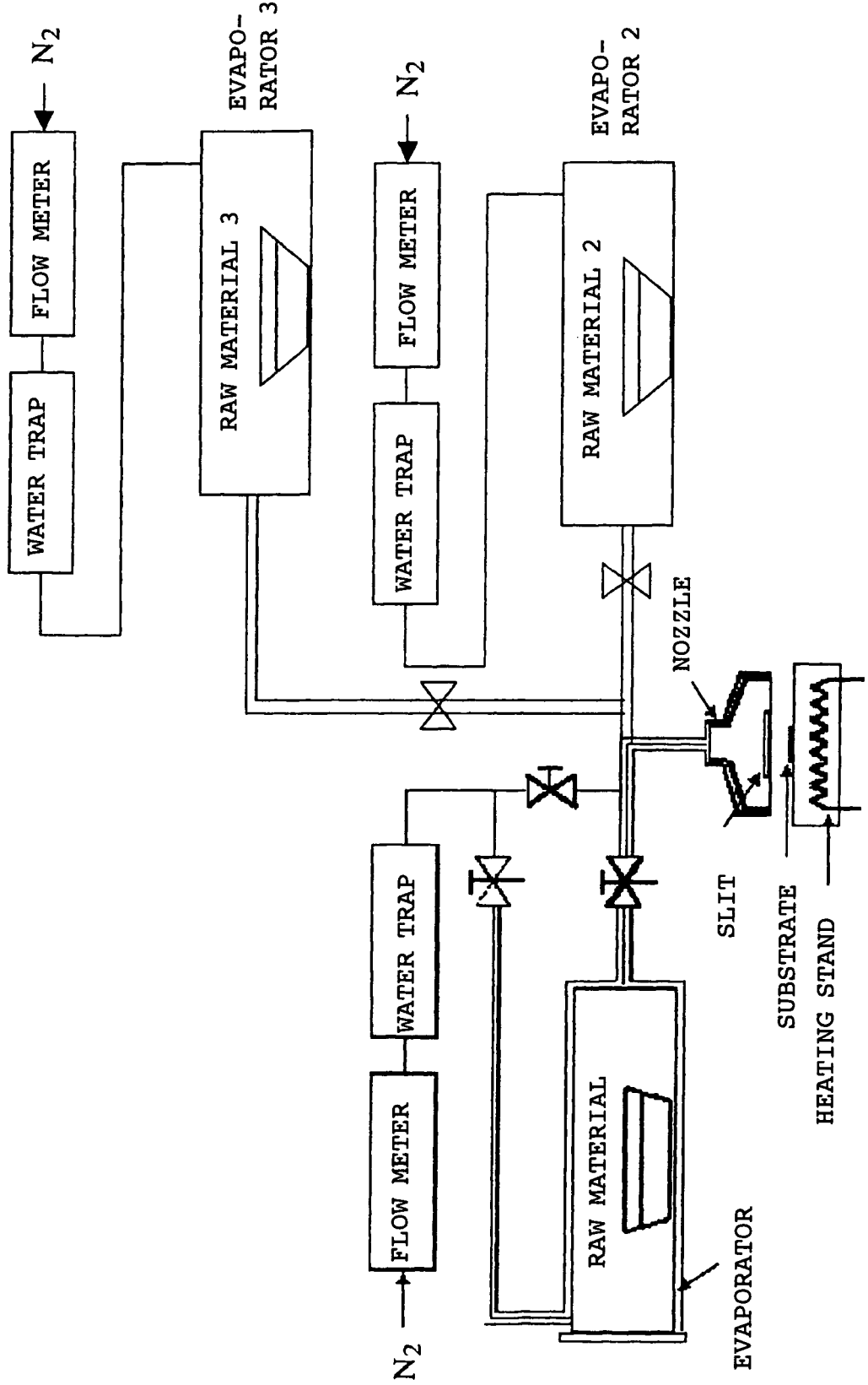
FIG. 20 is a simplified diagram of the apparatus for manufacturing the porous semiconductor in Example 5.

Porous SiC with a diameter of 25 mm and a thickness of 0.5 mm was used as the substrate. The porosity was 50% and the average pore size was 0.2 μm. As shown in FIG. 20, An evaporator was charged with $Zn(C_5H_7O_2)_2$ (the main raw material), the contents were heated to 130° C. and sublimated, then transported by argon gas and sprayed for 35 minutes from a slit nozzle perpendicular to a porous substrate kept at 600° C. on a heating stand equipped with a heater. The nozzle scanned at a rate of 5 mm/min.

Meanwhile, $Al(OC_2H_5)_3$ (raw material 2) was charged into a second evaporator and evaporated at a temperature of 210° C., while $PO(OC_2H_5)_3$ (raw material 3) was charged into a third evaporator and evaporated at a temperature of 120° C. During the first 15 minutes of spraying, a tiny amount of $Al(OC_2H_5)_3$ component was added, which was followed by 5 minutes with no doping, and during the next 15 minutes a tiny amount of $PO(OC_2H_5)_3$ component was added. This grew ZnO whiskers perpendicular to the substrate, producing Sample 7. For comparison, whiskers were similarly grown without doping, and the product was termed Sample 8. As a result, whiskers with a diameter of 0.5 μm and a length of 10 μm were grown at a spacing of 10 μm perpendicular to the substrate. X-ray analysis revealed the whiskers to be ZnO grown along the c axis of the substrate.

A gold foil mesh (porous, with through-holes having an average diameter of 5 μm, and a porosity of 50%) with a diameter of 25 mm and a thickness of 1 μm was placed on the surface of the ZnO whisker film produced above, and this was heated in a vacuum at a temperature of 1100° C. to bond the mesh to the whisker film. This product was evaluated as follows.

Evaluation: A voltage of 5 V was applied, and the emission wavelength and intensity were measured.

Figure 21:
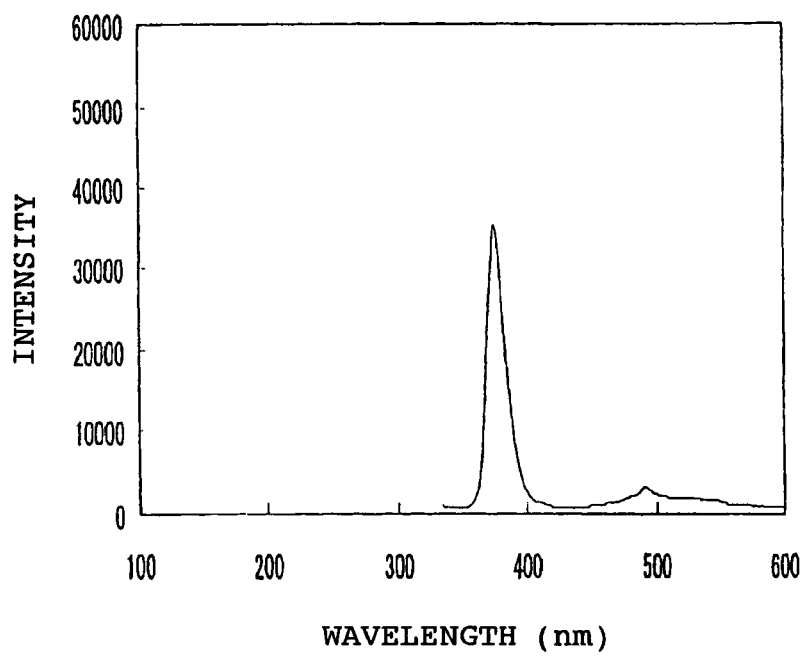
FIG. 21 is a graph of the emission spectrum of Samples 7 and 8 produced in Example 5.
Figure 21:
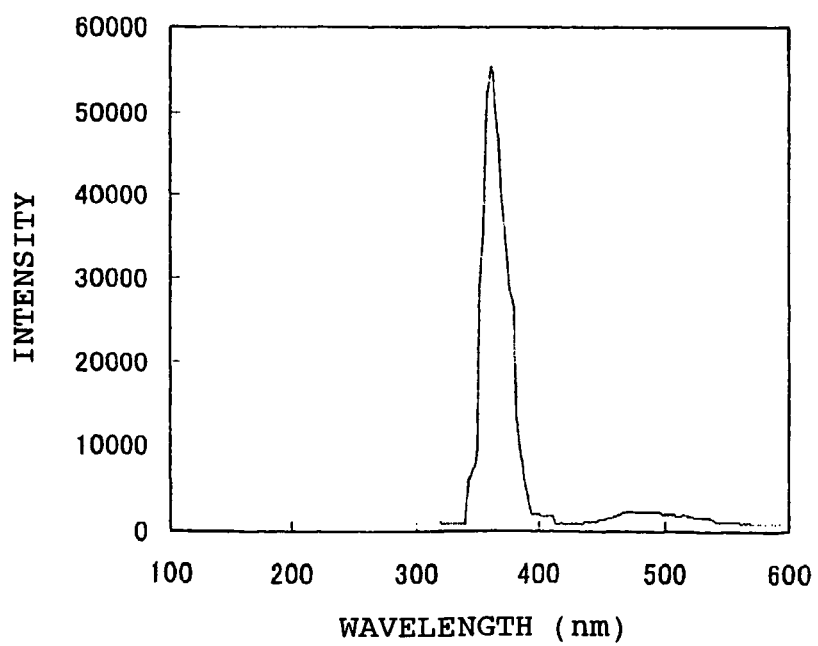
Figure 22:
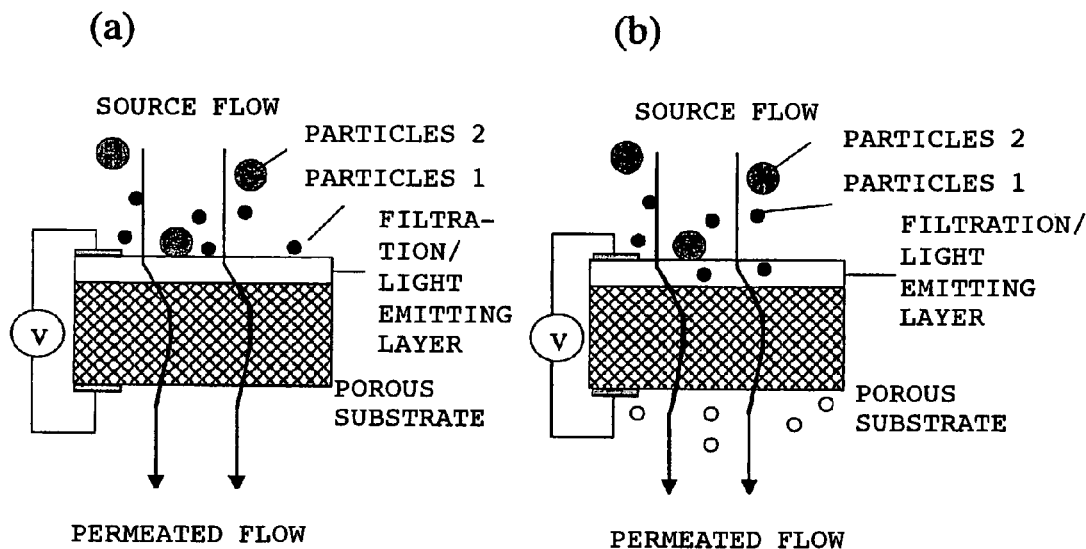
FIG. 22 is a diagram illustrating the basic structure and a usage mode of the porous semiconductor of the present invention.

FIG. 21 gives a comparison of the emission intensity of Sample 8(*a*) and Sample 7(*b*). A spectrum having the light emitting center at approximately 370 nm was obtained for both Samples 7 and 8, but the emission intensity was higher for Sample 7 (FIG. 21(*b*)) than for Sample 8 (FIG. 21(*a*)). The reason is believed to be that a p-i-n junction was formed in Sample 7, so light was emitted at a higher level of energy conversion efficiency.

EXAMPLE 6

The porous semiconductor of Example 6 was produced as follows and used to make a device, which was evaluated. Here, the porous semiconductor layer was formed by deposition of semiconductor particles.

Production of Device (1) Step 1

Porous SiC with a diameter of 25 mm and a thickness of 1 mm was used as the porous substrate. The porosity was 50% and the average pore size was 2 μm.

(2) Step 2

A GaN powder with an average particle size of 3 μm and a purity of 99.999% was placed in a sapphire crucible and heat treated for 0 or 2 hours at a temperature of 950° C. and in a vacuum (degree of vacuum $10^{-4}$ Pa). The heat treated GaN powder was dispersed in a 10% ethanol solution of titanium isopropoxide ($Ti(OC_2H_5)_4$), after which just the powder was recovered from the suspension and dried. The powder was then heat treated in the air for 1 hour at 500° C. to coat the GaN powder surface with a 0.8 μm porous $TiO_2$ film. A specific amount of $TiO_2$-coated GaN powder and 2 wt % (with respect to the powder) methyl cellulose (used as an organic binder) were dispersed in ethanol to produce a suspension with a concentration of 300 ppm.

(3) Step 3

The suspension of Step 2 was filtered through the porous substrate of Step 1 to coat the substrate with a porous GaN layer of 2 μm. The pressure differential before and after filtration was 0.1 MPa. After this, the product was dried at room temperature, and then heat treated in the air at a temperature of 450° C.

(4) Step 4

An electrode was produced by coating the back of the porous substrate and the GaN layer surface with a mesh of gold by sputtering.

Device Evaluation (1) Evaluation of Electroluminescence

Figure 26:
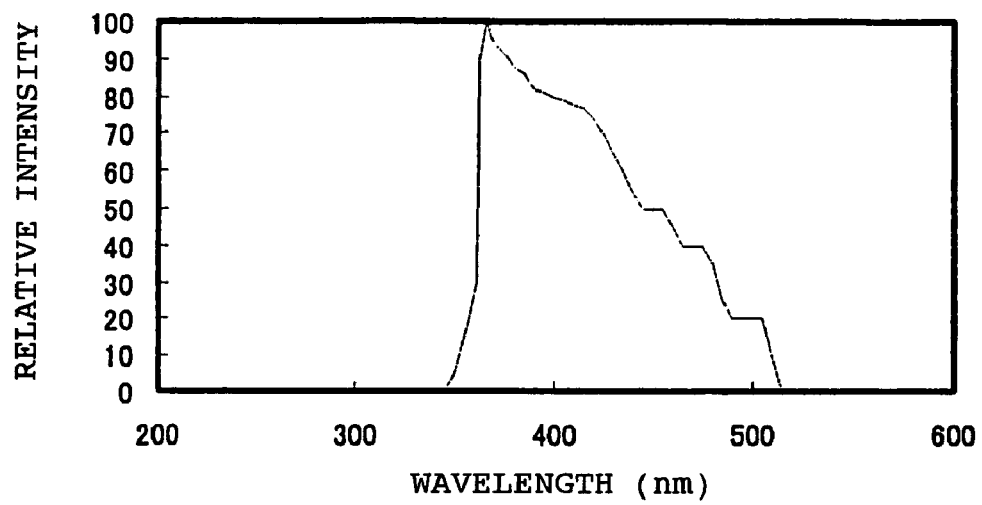
FIG. 26 is a graph of the emission spectrum of the porous semiconductor produced in Example 6.
Figure 26:
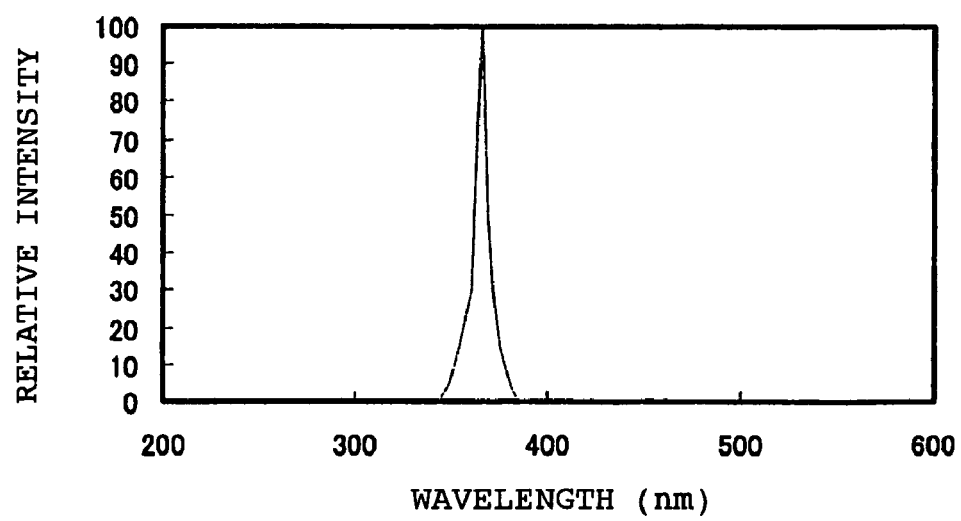

Current was injected into the device produced above, and the electroluminescence was measured. Current injection was performed by applying an AC voltage of 80 V. FIG. 26 is graphs of the spectrum obtained as the measurement result. FIG. 26(a) is when no heat treatment was performed in Step 2, and the luminous intensity had a broad spectrum, but in FIG. 26(b) in which the heat treatment was performed, only the band end emission of GaN was seen. The reason is believed to be that the heat treatment increased crystallinity.

(2) Evaluation of Harmful Substance Removal Performance

Figure 23:
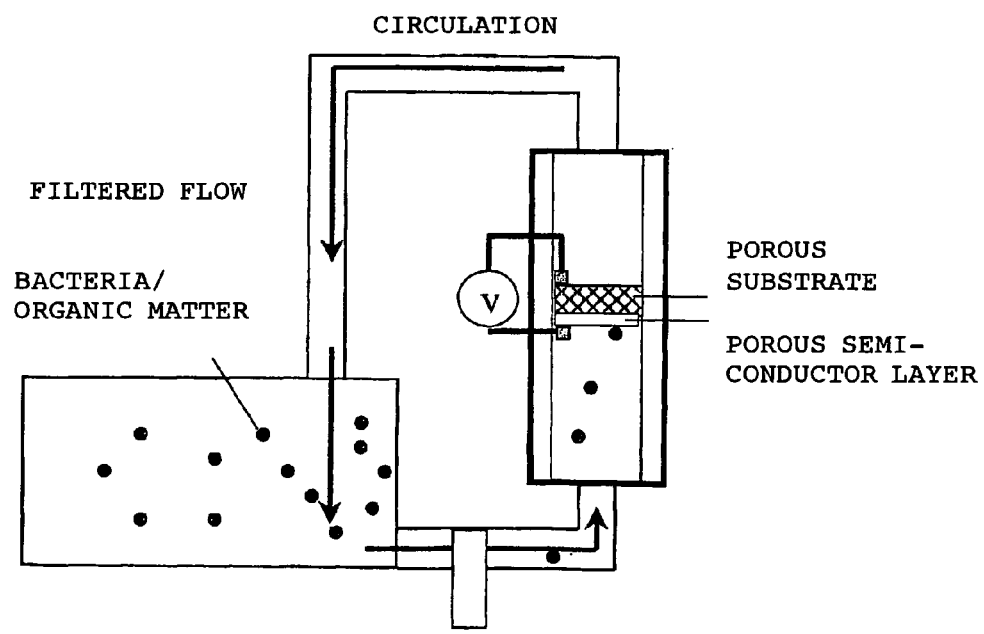
FIG. 23 is a diagram illustrating a usage mode when the porous semiconductor of the present invention is used to treat a fluid.
Figure 24:
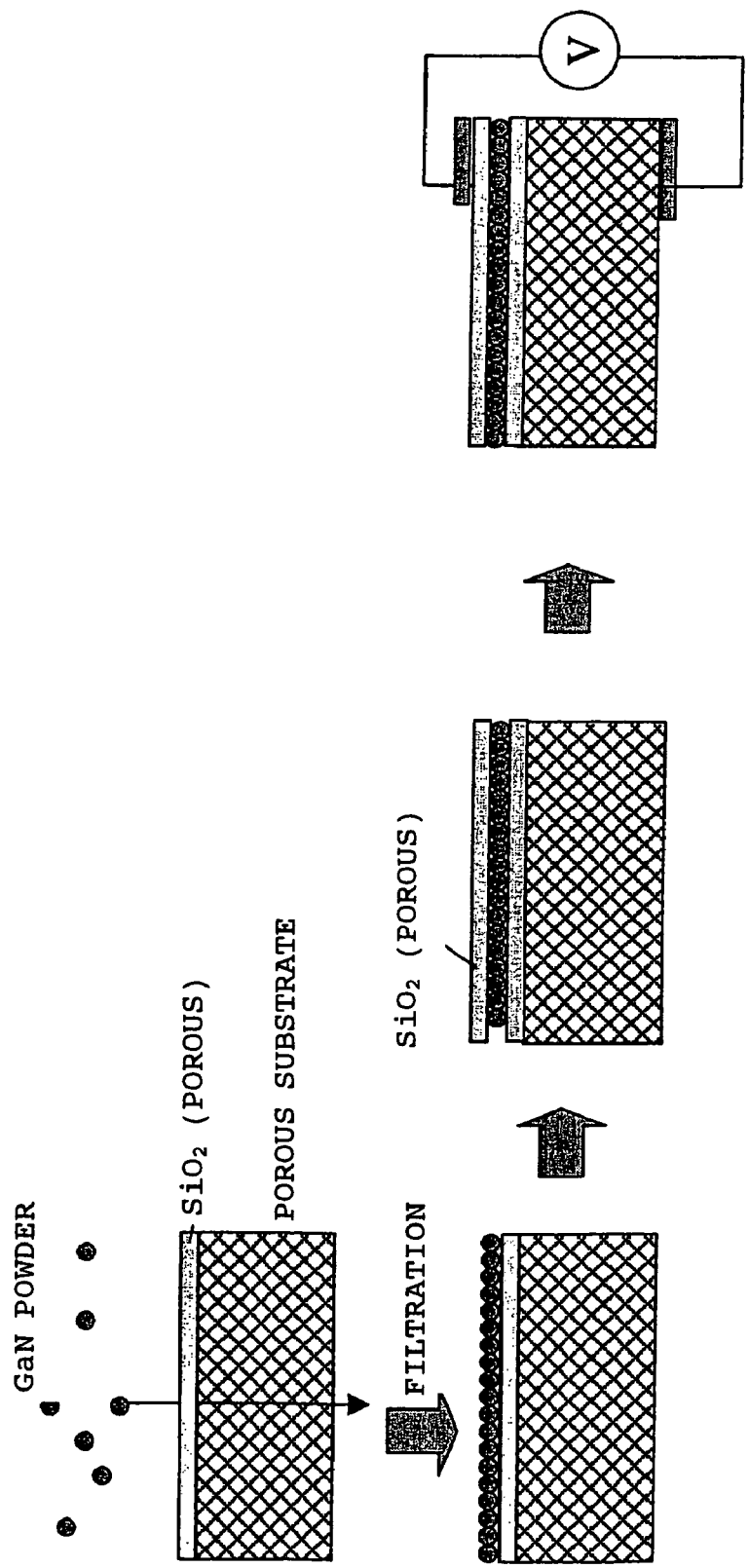
FIG. 24 illustrates the steps involved in the manufacture of a porous semiconductor layer when GaN is used as the semiconductor material.
Figure 25:
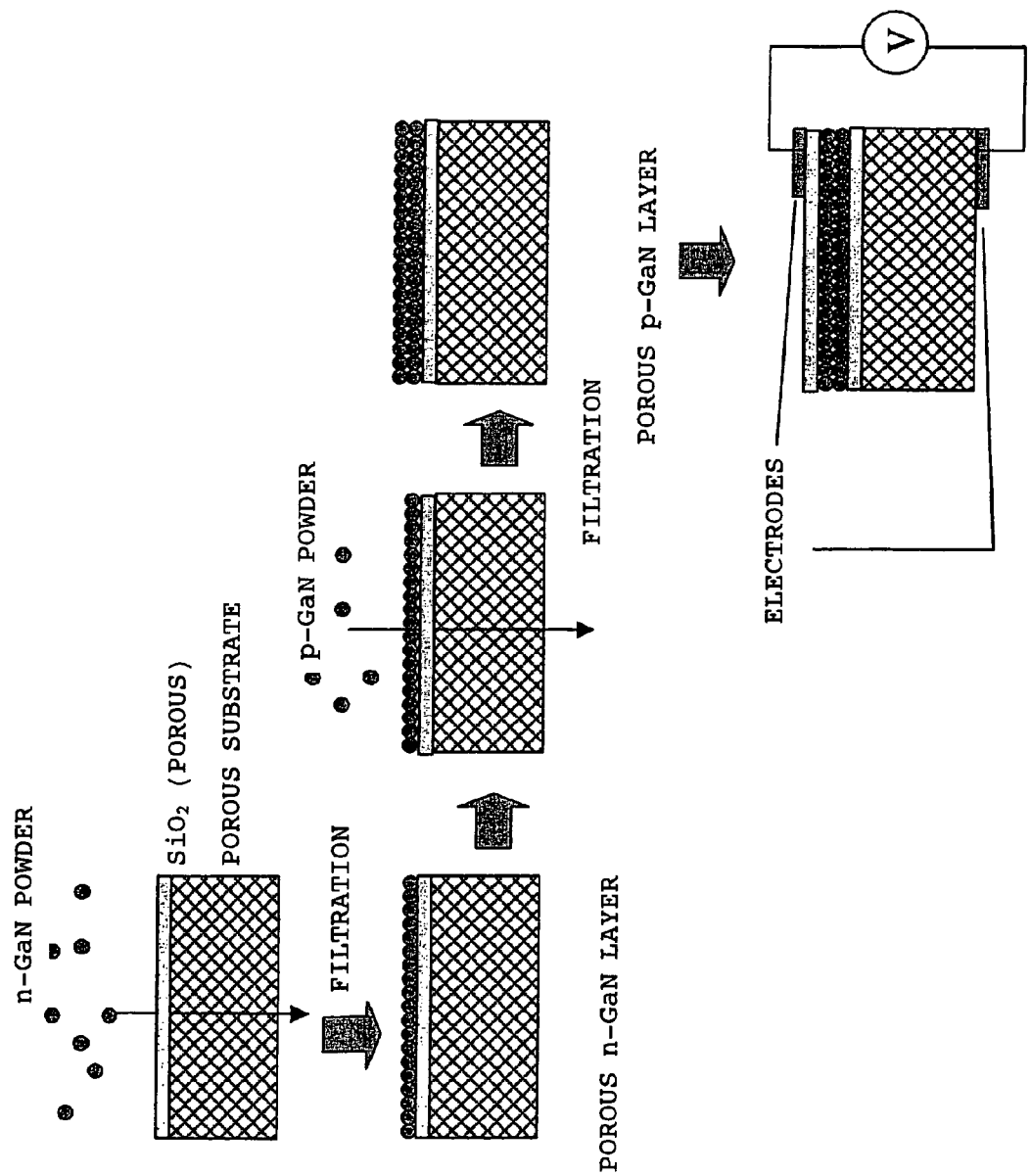
FIG. 25 illustrates the steps involved in the manufacture of a porous semiconductor layer having a pn junction when GaN is used as the semiconductor material.

Using the apparatus shown in FIG. 23, $NO_2$ gas was sprayed into an air cylinder with a volume of 10 liters to produce a gas with a concentration of 50 ppm. While voltage was applied (or not applied), the gas was supplied from the semiconductor layer side of the sample, and circulating filtration was performed for 2 hours. The $NO_2$ concentration in the tank was measured after 2 hours.

When the sample was not heat treated, the $NO_2$ concentration after 2 hours was 25 ppm. With the sample that was heat treated, the $NO_2$ concentration dropped to about zero, and the $NO_2$ had been completely decomposed. This is because the $NO_2$ gas was decomposed by the photocatalyst excited by ultraviolet light as the $NO_2$ gas passed through the porous semiconductor layer. It is believed that the heat treatment results in a higher emission intensity at the band ends, so the $NO_2$ gas is almost completely decomposed. Meanwhile, when no voltage was applied during circulating filtration, the $NO_2$ concentration after 2 hours remained unchanged at 50 ppm.

EXAMPLE 7

The porous semiconductor of Example 7 was produced as follows and used to make a device, which was evaluated. Here, the porous semiconductor layer was formed by deposition of semiconductor particles.

Production of Device (1) Step 1

Porous SiC with a diameter of 25 mm and a thickness of 1 mm was used as the porous substrate. The porosity was 50% and the average pore size was 2 μm.

(2) Step 2

An n-type GaN powder with an average particle size of 3 μm was placed in a sapphire crucible and heat treated for 2 hours at a temperature of 900° C. and in a vacuum (degree of vacuum $10^{-4}$ Pa). A specific amount of GaN powder and 2 wt % (with respect to the powder) methyl cellulose (used as an organic binder) were dispersed in ethanol to produce a suspension A with a concentration of 300 ppm. Next, a p-type GaN powder with an average particle size of 3 μm was placed in a sapphire crucible and heat treated for 2 hours at a temperature of 900° C. and in a vacuum (degree of vacuum $10^{-4}$ Pa). A specific amount of GaN powder and 2 wt % (with respect to the powder) methyl cellulose (used as an organic binder) were dispersed in ethanol to produce a suspension B with a concentration of 300 ppm.

(3) Step 3

Suspension A of Step 2 was filtered through the porous substrate of Step 1 to coat the substrate with an n-type porous GaN layer of 1 μm. The pressure differential before and after filtration was 0.1 MPa. Suspension B of Step 2 was then filtered to coat the substrate with a p-type porous GaN layer of 1 μm. The pressure differential before and after filtration was 0.1 MPa.

(4) Step 4

A solution was prepared by dissolving titanium isopropoxide $(Ti(OC_2H_5)_4)$, which is an alkoxide reagent of titanium, in ethanol. The sample of Step 3 was immersed in this solution, after which it was heated for 1 hour in the air at a temperature of 500° C. to coat the GaN powder surface with $TiO_2$.

(5) Step 5

An electrode was produced by coating the back of the porous substrate and the GaN layer surface with a mesh of gold by sputtering.

Device Evaluation (1) Evaluation of Electroluminescence

Figure 27:
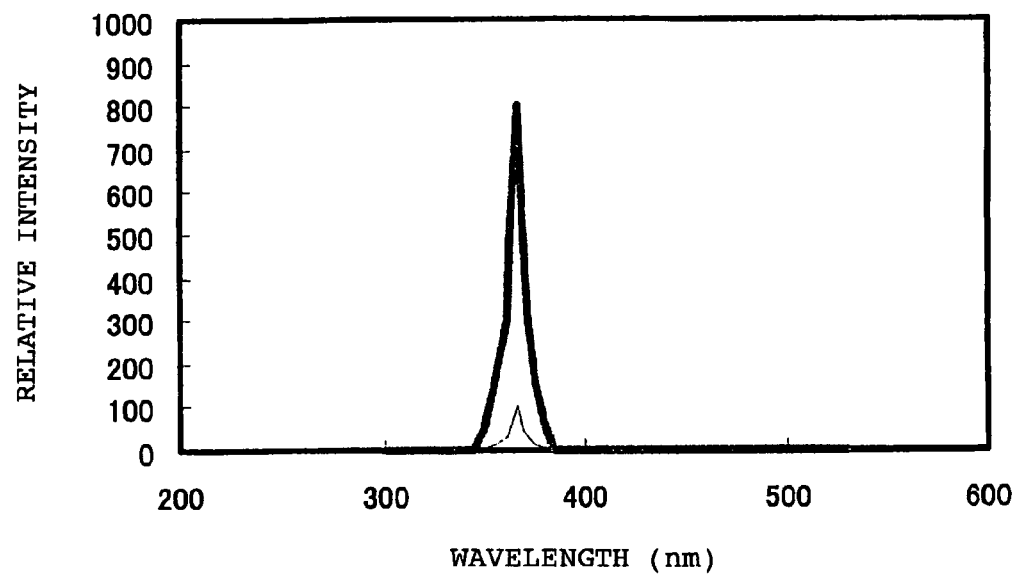
FIG. 27 is a graph of the emission spectrum of the porous semiconductor having a pn junction produced in Example 7.

Current was injected into the device produced above, and the electroluminescence was measured. Current injection was performed by applying an AC voltage of 20 V. FIG. 27 is a graph of the emission spectrum obtained as the measurement result. FIG. 27 also shows the results after the 2 hours of heat treatment performed in Example 6. The result was the same as in Example 6 in that only the band end emission of GaN was seen, but luminous intensity was greatly increased. The reason is believed to be that a pn junction was introduced.

(2) Evaluation of Harmful Substance Removal Performance

Using the apparatus shown in FIG. 23, $SO_2$ gas was sprayed into an air cylinder with a volume of 10 liters to produce a gas with a concentration of 500 ppm. While voltage was applied (or not applied), the gas was supplied from the semiconductor layer side of the sample, and circulating filtration was performed for 2 hours. The $SO_2$ concentration in the tank was measured after 2 hours. The sample of Example 6, which had been heat treated for 2 hours, was similarly measured.

The $SO_2$ concentration had dropped to zero after 2 hours, and the $SO_2$ had been completely decomposed. This is because the $SO_2$ gas was decomposed by the photocatalyst excited by ultraviolet light as the $SO_2$ gas passed through the porous semiconductor layer. With the sample of Example 6, the $SO_2$ concentration decreased to 320 ppm. The reason is believed to be that the pn junction in Example 7 resulted in light of higher luminance being emitted, so the decomposition efficiency was higher. Meanwhile, when no voltage was applied during circulating filtration, the $SO_2$ concentration after 2 hours remained unchanged at 500 ppm.

EXAMPLE 8

The porous semiconductor of Example 8 was produced as follows and used to make a device, which was evaluated. Here, the porous semiconductor layer was formed by deposition of semiconductor particles.

Production of Device (1) Step 1

Porous $Si_3N_4$ with a diameter of 25 mm and a thickness of 1 mm was used as the porous substrate. The porosity was 50% and the average pore size was 1 µm. A gold mesh electrode of 0.5 µm was formed on one side of the porous substrate.

(2) Step 2

An n-type AlN powder with an average particle size of 1.5 µm was placed in a sapphire crucible and heat treated for 2 hours at a temperature of 880° C. and in a vacuum (degree of vacuum $10^{-4}$ Pa). A specific amount of AlN powder and 2 wt % (with respect to the powder) methyl cellulose (used as an organic binder) were dispersed in ethanol to produce a suspension A with a concentration of 300 ppm. Next, a p-type AlN powder with an average particle size of 1.4 µm was placed in a sapphire crucible and heat treated for 2 hours at a temperature of 880° C. and in a vacuum (degree of vacuum $10^{-4}$ Pa). A specific amount of AlN powder and 2 wt % (with respect to the powder) methyl cellulose(used as an organic binder) were dispersed in ethanol to produce a suspension B with a concentration of 300 ppm.

(3) Step 3

Suspension A of Step 2 was filtered from the gold electrode side of the porous substrate of Step 1 to coat the substrate with an n-type porous AlN layer of 1 µm. The pressure differential before and after filtration was 0.1 MPa. Suspension B of Step 2 was then filtered to coat the substrate with a p-type porous AlN layer of 1 µm. The pressure differential before and after filtration was 0.1 MPa.

(4) Step 4

An electrode was produced by coating the AlN layer surface with a mesh of gold by sputtering.

Device Evaluation (1) Evaluation of Electroluminescence

Figure 28:
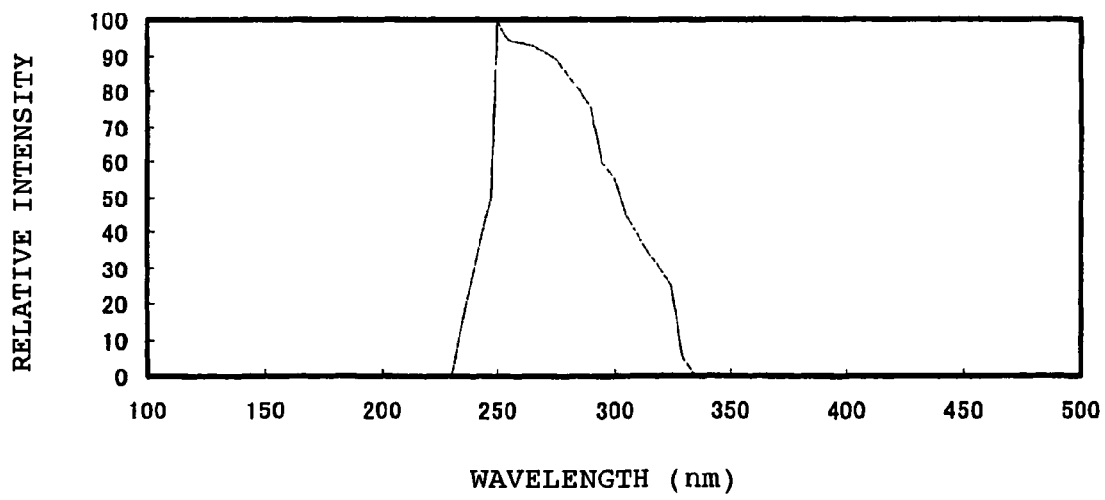
FIG. 28 is a graph of the emission spectrum of the porous semiconductor produced in Example 8.
Figure 29:
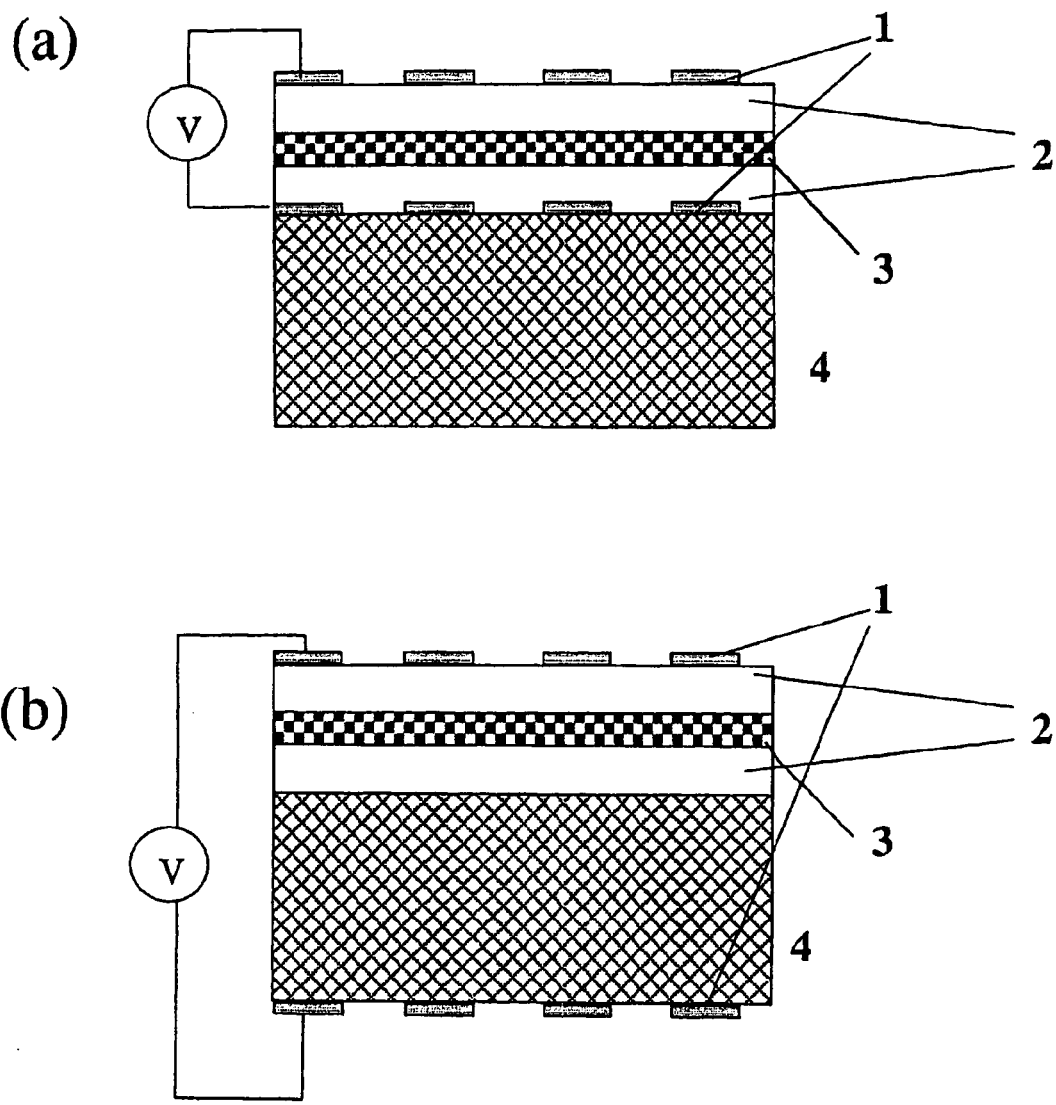
FIG. 29 is a diagram illustrating the basic structure of the porous semiconductor of the present invention.
Figure 30:
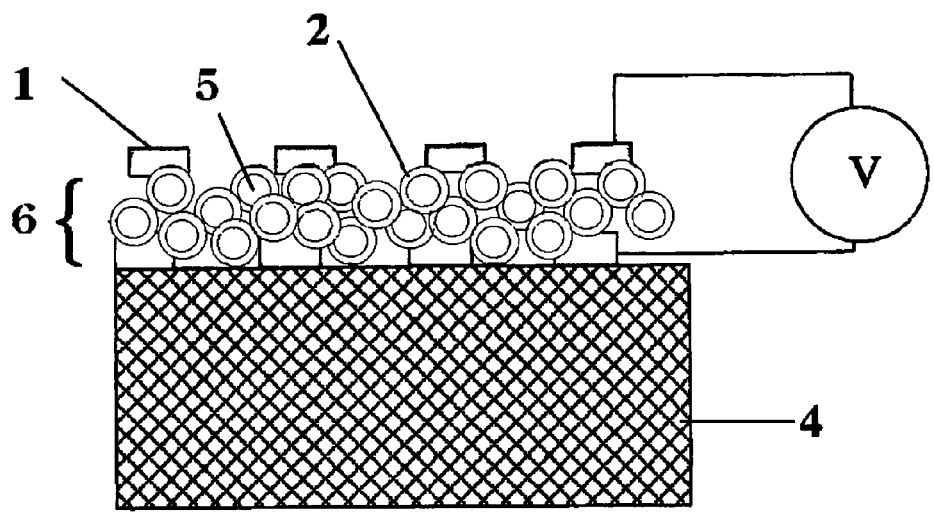
FIG. 30 is another diagram illustrating the basic structure of the porous semiconductor of the present invention.

Current was injected into the device produced above, and the electroluminescence was measured. Current injection was performed by applying an AC voltage of 150 V. FIG. 28 is a graph of the emission spectrum obtained as the measurement result. As can be seen from FIG. 28, a broad emission from 235 to 325 nm was confirmed.

(2) Evaluation of Harmful Substance Removal Performance

Using the apparatus shown in FIG. 23, *E. coli* (average particle size of 0.5 µm) were sprayed into an air cylinder with a volume of 10 liters to produce a gas with a concentration of 150 ppm. While voltage was applied (or not applied), the gas was supplied from the semiconductor layer side of the sample, and circulating filtration was performed for 2 hours. The *E. coli* concentration in the tank was measured after 2 hours.

As a result, the *E. coli* concentration had dropped to zero after 2 hours, and the bacteria had been completely killed. This is because the *E. coli* were killed directly by ultraviolet light as they passed through the porous semiconductor layer. Meanwhile, when no voltage was applied during circulating filtration, the *E. coli* concentration after 2 hours remained unchanged at 150 ppm.

EXAMPLE 9

In this example, a porous semiconductor in which semiconductor particles were dispersed in an insulating layer was manufactured and evaluated as follows.

Production of Device (1) Step 1

Porous SiC with a diameter of 25 mm and a thickness of 1 mm was used as a sheet-form porous substrate. The porosity was 50% and the average pore size was 1 μm.

(2) Step 2

The following semiconductor powders were readied.

① GaN: A GaN powder with an average particle size of 0.9 μm and a purity of 99.999% was placed in a sapphire crucible and heat treated for 2 hours at a temperature of 950° C. and in a vacuum (degree of vacuum $10^{-4}$ Pa) to remove the hydrogen in the GaN.

② ZnO: A ZnO powder with an average particle size of 0.9 μm and a purity of 99.999% was placed in a sapphire crucible and heat treated for 2 hours at a temperature of 950° C. and in oxygen to compensate for oxygen deficiency in the ZnO.

③ ($ZnF_2$:Gd): A $ZnF_2$ powder with an average particle size of 0.1 μm and a purity of 99.999% and a $GdF_3$ powder with an average particle size of 0.1 μm and a purity of 99.999% were mixed in a mortar, after which a reaction was conducted for 2 hours in argon at a temperature of 650° C. to obtain a $ZnF_2$:Gd powder of various particle sizes. Gadolinium accounted for 3 mol % of the total. This product was pulverized to recover powders with average particle sizes of 1 μm, 0.1 μm, and 0.05 μm.

(3) Step 3

The various powders of Step 2 were each dispersed in a 5% ethanol solution of titanium isopropoxide ($Ti(OC_2H_5)_4$), after which just the powder was recovered from the suspension and dried. The powder was then heat treated in the air for 1 hour at 500° C. to coat the semiconductor powder surface with a 0.01 μm porous $TiO_2$ film. A specific amount of $TiO_2$-coated semiconductor was dispersed in ethanol to produce a suspension with a concentration of 300 ppm.

(4) Step 4

The suspension of Step 3 was filtered through the porous substrate of Step 1 to form a semiconductor particle dispersion type of porous semiconductor layer in a thickness of 10 μm on the porous substrate surface. The pressure differential before and after filtration was 0.1 MPa. After this, the product was dried at room temperature, and then heat treated in the air at a temperature of 450° C.

(5) Step 5

An electrode was produced by coating the back of the porous substrate and the light emitting layer surface with a mesh of gold by sputtering. Porous semiconductor samples 9 to 13 made of the materials and having the properties shown in Table 1 below were obtained.

Device Evaluation

As shown in FIG. 23, 0.01 mol of gasified trichloroethylene was sprayed into an air cylinder with a volume of 10 liters. While AC voltage with a frequency of 2.5 kHz and a voltage of 200 V was applied, the gas was supplied from the semiconductor layer side of each sample, and circulating filtration was performed. The time was measured until the trichloroethylene concentration in the tank reached zero. These results are given in Table 1 below.

TABLE 1

| Sample No. | Substrate | Semiconductor material | Semiconductor particle size (μm) | Insulating layer material | Insulating layer thickness (μm) | Porosity (%) | Porous Semiconductor layer thickness (μm) | Time until decomposition (hrs) |
|---|---|---|---|---|---|---|---|---|
| 9 | SiC | GaN | 0.9 | $TiO_2$ | 0.01 | 50 | 10 | 1234.8 |
| 10 | SiC | ZnO | 0.9 | $TiO_2$ | 0.01 | 50 | 10 | 814.3 |
| 11 | SiC | $ZnF_2$:Gd | 1 | $TiO_2$ | 0.01 | 50 | 10 | 145.3 |
| 12 | SiC | $ZnF_2$:Gd | 0.1 | $TiO_2$ | 0.01 | 50 | 10 | 12.3 |
| 13 | SiC | $ZnF_2$:Gd | 0.05 | $TiO_2$ | 0.01 | 50 | 10 | 3 |

As is clear from Table 1, it took less time for the trichloroethylene to be completely decomposed when $ZnF_2$:Gd was used than when GaN or ZnO was used. The smaller was the particle size of the $ZnF_2$:Gd, the less time decomposition took. This is believed to be because the light emission wavelength becomes shorter as the particle size decreases, resulting in a high energy level, and because the quantum size effect increases brightness.

EXAMPLE 10

In this example, a porous semiconductor in which semiconductor particles were dispersed in an insulating layer was manufactured and evaluated as follows.

Production of Device
(1) Step 1
Porous SiC with a diameter of 25 mm and a thickness of 1 mm was used as the substrate. The porosity was 50% and the average pore size was 1 μm.
(2) Step 2
The following semiconductor powders were readied.
① $ZnF_2$:Gd: Same as in Example 9.
② AlN:Gd
An AlN powder with an average particle size of 0.1 μm and a purity of 99.999% and a $GdCl_3$ powder with an average particle size of 0.11 μm and a purity of 99.999% were mixed in a mortar, after which a reaction was conducted for 2 hours in argon at a temperature of 800° C. to obtain an AlN:Gd powder of various particle sizes. Gadolinium accounted for 3 mol % of the total aluminum. This product was pulverized to recover powders with average particle sizes of 1 μm, 0.1 μm, and 0.05 μm.
③ Diamond:Gd
Gadolinium ions were implanted by ion implantation in diamond powders having average particle sizes of 1, 0.1, and 0.05 μm. After this, the product was annealed in a vacuum at a temperature of 800° C. to obtain a diamond:Gd powder of various particle sizes. Gadolinium accounted for 3 mol % of the total.

(3) Step 3
The various powders of Step 2 were each dispersed in a 5% ethanol solution of titanium isopropoxide ($Ti(OC_2H_5)_4$), after which just the powder was recovered from the suspension and dried. The powder was then heat treated in the air for 1 hour at 500° C. to coat the semiconductor powder surface with a 0.01 μm porous $TiO_2$ film. A specific amount of $TiO_2$-coated semiconductor was dispersed in ethanol to produce a suspension with a concentration of 300 ppm.

(4) Step 4
The suspension of Step 3 was filtered through the porous substrate of Step 1 to form a semiconductor particle dispersion type of porous semiconductor layer in a thickness of 10 μm on the porous substrate surface. The pressure differential before and after filtration was 0.1 MPa. After this, the product was dried at room temperature, and then heat treated in the air at a temperature of 450° C.

(5) Step 5
An electrode was produced by coating the back of the porous substrate and the light emitting layer surface with a mesh of gold by sputtering. Porous semiconductor samples 14 to 22 made of the materials and having the properties shown in Table 2 below were obtained.

Device Evaluation
Just as in Example 9, 0.01 mol of gasified trichloroethylene was sprayed into an air cylinder with a volume of 10 liters. While AC voltage with a frequency of 5 kHz and a voltage of 280 V was applied, the gas was supplied from the semiconductor layer side of each sample, and circulating filtration was performed. The time was measured until the trichloroethylene concentration in the tank reached zero. These results are given in Table 2 below.

TABLE 2

| Sample No. | Substrate | Semiconductor material | Semiconductor particle size (μm) | Insulating layer material | Insulating layer thickness (μm) | Porosity (%) | Porous semiconductor layer thickness (μm) | Time until decomposition (hrs) |
|---|---|---|---|---|---|---|---|---|
| 14 | SiC | $ZnF_2$:Gd | 1 | $TiO_2$ | 0.01 | 50 | 10 | 145.3 |
| 15 | SiC | $ZnF_2$:Gd | 0.1 | $TiO_2$ | 0.01 | 50 | 10 | 12.3 |
| 16 | SiC | $ZnF_2$:Gd | 0.05 | $TiO_2$ | 0.01 | 50 | 10 | 3 |
| 17 | SiC | AlN:Gd | 1 | $TiO_2$ | 0.01 | 50 | 10 | 151.4 |
| 18 | SiC | AlN:Gd | 0.1 | $TiO_2$ | 0.01 | 50 | 10 | 14.7 |
| 19 | SiC | AlN:Gd | 0.05 | $TiO_2$ | 0.01 | 50 | 10 | 4.9 |
| 20 | SiC | diamond:Gd | 1 | $TiO_2$ | 0.01 | 50 | 10 | 169 |
| 21 | SiC | diamond:Gd | 0.1 | $TiO_2$ | 0.01 | 50 | 10 | 14.7 |
| 22 | SiC | diamond:Gd | 0.05 | $TiO_2$ | 0.01 | 50 | 10 | 2.6 |

It was confirmed that decomposition is again achieved when AlN or diamond is used instead of $ZnF_2$. It also took less time for the trichloroethylene to be completely decomposed as the particle size decreased.

EXAMPLE 11

In this example, A porous semiconductor having a porous insulating layer/porous semiconductor layer/porous insulating layer structure was manufactured and evaluated.

Device Evaluation

As shown in FIG. 23, 0.01 mol of gasified trichloroethylene was sprayed into an air cylinder with a volume of 10 liters. While AC voltage with a frequency of 2.5 kHz and a voltage of 200 V was applied, gas was supplied from the semiconductor layer side of each sample, and circulating filtration was performed. The time was measured until the trichloroethylene concentration in the tank reached zero. These results are given in Table 3 below.

TABLE 3

| Sample No. | Substrate | Semiconductor material | Semiconductor particle size (μm) | Insulating layer material | Insulator particle size (μm) | Insulator dielectric constant | $TiO_2$ thickness (μm) | Time until decomposition (hrs) |
|---|---|---|---|---|---|---|---|---|
| 23 | SiC | $ZnF_2$:Gd | 1 | $TiO_2$ | 0.1 | 60 | none | 11.6 |
| 24 | SiC | $ZnF_2$:Gd | 1 | $Ta_2O_5$ | 0.1 | 25 | 10 | 17.6 |
| 25 | SiC | $ZnF_2$:Gd | 1 | $Al_2O_3$ | 0.1 | 8 | 10 | 20.8 |
| 26 | SiC | $ZnF_2$:Gd | 1 | $SiO_2$ | 0.1 | 4 | 10 | 21.1 |
| 27 | SiC | $ZnF_2$:Gd | 1 | $PbTiO_3$ | 0.1 | 150 | 10 | 13.6 |

Production of Device (1) Step 1

Porous SiC with a diameter of 25 mm and a thickness of 1 mm was used as the substrate. The porosity was 50% and the average pore size was 1 μm.

(2) Step 2

The following semiconductors, insulators, and photocatalyst powders were readied.

① Semiconductor Powder

Of the $ZnF_2$:Gd powders used in Example 9, the one with an average particle size of 1 μm was used.

② Insulator Powder $TiO_2$ (anatase), $Ta_2O_5$, $Al_2O_3$, $SiO_2$, and $PbTiO_3$ were used, all with a particle size of 0.1 μm.

③ Photocatalyst Powder

Anatase $TiO_2$ with a particle size of 0.01 μm was used.

(3) Step 3

The various powders of Step 2 were each dispersed in ethanol to produce a suspension with a concentration of 300 ppm.

(4) Step 4

The various suspensions of Step 3 were each filtered through the porous substrate of Step 1 to form an insulating layer (10 μm), a semiconductor layer (10 μm), and an insulating layer (1 μm), in that order, on the porous substrate surface. The pressure differential before and after filtration was 0.1 MPa.

(5) Step 5

An electrode was produced by coating the insulating layer surface of Step 4 with a mesh of gold by sputtering.

(6) Step 6

The insulating layer surface of Step 5 (except for the sample in which the insulating layer was $TiO_2$) was coated in a thickness of 10 μm with $TiO_2$ having a particle size of 0.01 μm in the same manner as in Step 4. After this, the product was dried at room temperature, and then heat treated in the air at a temperature of 450° C. This yielded porous semiconductor samples 23 to 27 made of the materials and having the properties shown in Table 3 below.

It was confirmed that that decomposition is again achieved when $Ta_2O_5$, $Al_2O_3$, $SiO_2$, or $PbTiO_3$ is used as the insulating material. The decomposition time can be shortened by using a material with a large dielectric constant such as $PbTiO_3$.

EXAMPLE 12

In this example, a porous semiconductor layer composed of $Si_3N_4$ particles and an oxide-based binder phase containing a rare earth element was formed. The same porous silicon nitride that formed the porous semiconductor layer was used as the substrate.

$Y_2O_3$ and $Gd_2O_3$ powders with an average particle size of 0.5 μm (used as auxiliaries) were added as shown in Table 4 below to an α-type $Si_3N_4$ powder with an average particle size of 0.5 μm or 2.2 μm. The resulting mixed powder was mixed with an organic binder (methyl cellulose) and subjected to uniaxial molding, after which this product was fired for 1 hour in the air at a temperature of 500° C. to remove part of the carbon component of the binder. After this, the product was fired for 2 hours in nitrogen at a temperature of 1600 to 1800° C. and a pressure of 4 atmospheres to produce porous $Si_3N_4$. In Table 4, "auxiliary 1 wt %" and "auxiliary 2 wt %" indicate the proportions of the auxiliaries in the mixed powder (auxiliary 1+auxiliary 2).

The pore size of the porous $Si_3N_4$ thus obtained was measured by mercury porosimetry. The bending strength was measured according to the JIS three-point bending test. The aspect ratio (major diameter/minor diameter) of the $Si_3N_4$ particles was measured by SEM. The porous $Si_3N_4$ was irradiated with an excimer laser with a wavelength of 193 nm, and the wavelength of the light emitted from the porous $Si_3N_4$ was measured with a spectrometer. The brightness was measured by luminance meter, and was calculated as the relative brightness using sample No. 35, which had the highest brightness of all the porous $Si_3N_4$ of sample Nos. 28 to 35, as a base of 100. The results are given in Table 4.

TABLE 4

| No. | $Si_3N_4$ perticle size (μm) | Auxiliary 1 | Auxiliary 2 | Auxiliary 1 wt % | Auxiliary 2 wt % | $Si_3N_4$ wt % | Auxiliary (wt %) |
|---|---|---|---|---|---|---|---|
| 28 | 0.5 | $Y_2O_3$ | $Gd_2O_3$ | 100.0 | 0.0 | 92 | 8 |
| 29 | 0.5 | $Y_2O_3$ | $Gd_2O_3$ | 95.3 | 4.7 | 92 | 8 |
| 30 | 0.5 | $Y_2O_3$ | $Gd_2O_3$ | 84.9 | 15.1 | 92 | 8 |
| 31 | 0.5 | $Y_2O_3$ | $Gd_2O_3$ | 0.0 | 100.0 | 92 | 8 |
| 32 | 0.5 | $Y_2O_3$ | $Gd_2O_3$ | 0.0 | 100.0 | 99 | 2 |
| 33 | 0.5 | $Y_2O_3$ | $Gd_2O_3$ | 0.0 | 100.0 | 92 | 8 |
| 34 | 2.2 | $Y_2O_3$ | $Gd_2O_3$ | 0.0 | 100.0 | 92 | 8 |
| 35 | 0.5 | $Y_2O_3$ | $Gd_2O_3$ | 0.0 | 100.0 | 86 | 14 |

| No. | Sintering temp. (° C.) | Porosity (%) | Aspect ratio | Average pore size (μm) | Emission peak wavelength (nm) | Relative brightness | Bending strength (MPa) |
|---|---|---|---|---|---|---|---|
| 28 | 1800 | 50.0 | 11.0 | 0.80 |  | 0 | 266 |
| 29 | 1800 | 49.5 | 11.0 | 0.79 | 312 | 15 | 265 |
| 30 | 1800 | 49.6 | 10.9 | 0.78 | 310 | 21 | 264 |
| 31 | 1800 | 49.1 | 11.2 | 0.78 | 311 | 51 | 271 |
| 32 | 1800 | 50.0 | 2.8 | 0.40 | 312 | 3 | 88 |
| 33 | 1600 | 50.0 | 1.6 | 0.40 | 312 | 1 | 33 |
| 34 | 1800 | 49.5 | 11.0 | 4.80 | 311 | 52 | 201 |
| 35 | 1800 | 49.1 | 9.2 | 0.78 | 311 | 100 | 166 |

Ultraviolet emission with a peak wavelength at about 311 nm was seen in the porous $Si_3N_4$ of sample Nos. 29 to 35. The more the $Gd_2O_3$ content increased, the higher was the brightness. On the other hand, with No. 33 in which the sintering temperature was low, and with the porous $Si_3N_4$ of No. 32 in which the auxiliary content was low, the aspect ratio of the $Si_3N_4$ particles was less than 3, strength decreased, and brightness also went down. No emission peak was seen with the porous $Si_3N_4$ of No. 28 in which the wavelength was between 300 and 350 nm, but emission with a peak wavelength of 450 nm was seen over 350 nm.

EXAMPLE 13

$Y_2O_3$ and $Eu_2O_3$ powders with an average particle size of 0.5 μm (used as auxiliaries) were added as shown in Table 5 below to an α-type $Si_3N_4$ powder with an average particle size of 0.5 μm. The resulting mixed powder was mixed with an organic binder (methyl cellulose) and subjected to uniaxial molding, after which this product was fired for 1 hour in the air at a temperature of 500° C. to remove part of the carbon component of the binder. After this, the product was fired for 2 hours in nitrogen at a temperature of 1800° C. and a pressure of 4 atmospheres to produce porous $Si_3N_4$. In Table 5, "auxiliary 1 wt %" and "auxiliary 2 wt %" indicate the proportions of the auxiliaries in the mixed powder (auxiliary 1+auxiliary 2).

The pore size of the porous $Si_3N_4$ thus obtained was measured by mercury porosimetry. The bending strength was measured according to the JIS three-point bending test. The aspect ratio (major diameter/minor diameter) of the $Si_3N_4$ particles was measured by SEM. The porous $Si_3N_4$ was irradiated with an He—Cd laser with a wavelength of 325 nm, and the wavelength of the light emitted from the porous $Si_3N_4$ was measured with a spectrometer.

Figure 31:
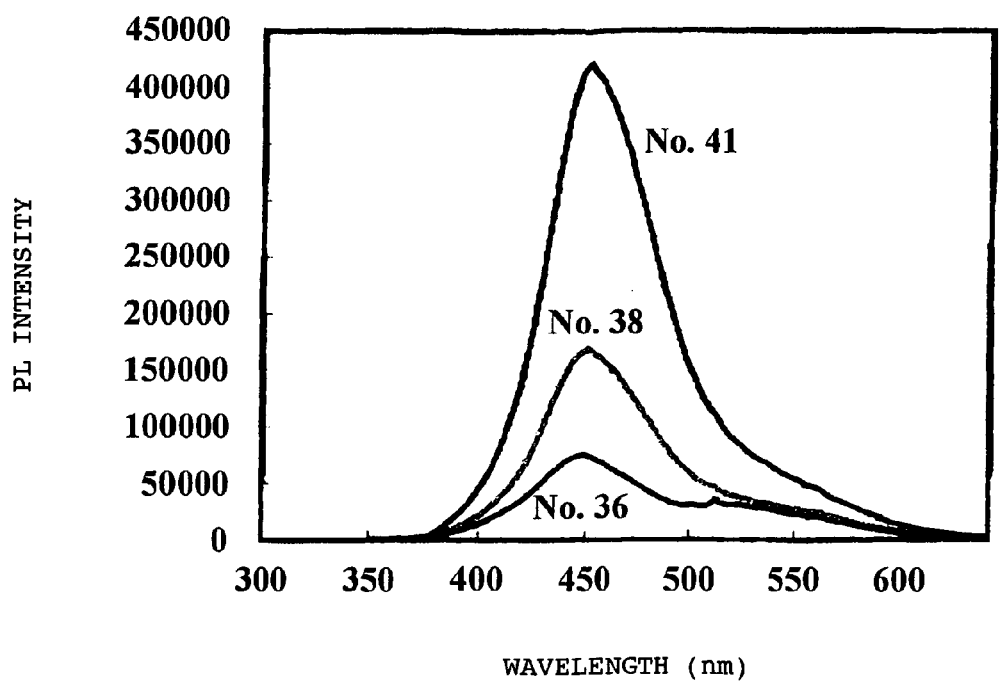
FIG. 31 is a graph of the emission spectrum of the porous $Si_3N_4$ in Nos. 36, 38, and 41 of Example 13.

The brightness was measured by luminance meter, and was calculated as the relative brightness using sample No. 41, which had the highest brightness of all the porous $Si_3N_4$ of sample Nos. 36 to 41, as a base of 100. The results are given in Table 5. The emission spectra for Nos. 36, 38, and 41 are shown in FIG. 31.

TABLE 5

| No. | $Si_3N_4$ particle size (μm) | Auxiliary 1 | Auxiliary 2 | Auxiliary 1 wt % | Auxiliary 2 wt % | $Si_3N_4$ wt % | Auxiliary (wt %) |
|---|---|---|---|---|---|---|---|
| 36 | 0.5 | $Y_2O_3$ | $Eu_2O_3$ | 100.0 | 0.0 | 92 | 8 |
| 37 | 0.5 | $Y_2O_3$ | $Eu_2O_3$ | 95.4 | 4.6 | 92 | 8 |
| 38 | 0.5 | $Y_2O_3$ | $Eu_2O_3$ | 85.2 | 14.8 | 92 | 8 |
| 39 | 0.5 | $Y_2O_3$ | $Eu_2O_3$ | 72.0 | 28.0 | 92 | 8 |
| 40 | 0.5 | $Y_2O_3$ | $Eu_2O_3$ | 39.1 | 60.9 | 92 | 8 |
| 41 | 0.5 | $Y_2O_3$ | $Eu_2O_3$ | 0.0 | 100.0 | 92 | 8 |

| No. | Sintering temp. (° C.) | Porosity (%) | Aspect ratio | Average pore size (μm) | Emission peak wavelength (nm) | Relative brightness | Bending strength (MPa) |
|---|---|---|---|---|---|---|---|
| 36 | 1800 | 50.0 | 10.9 | 0.45 | 449 | 20 | 255 |
| 37 | 1800 | 50.0 | 10.8 | 0.44 | 450 | 29 | 255 |
| 38 | 1800 | 47.0 | 9.7 | 0.42 | 450 | 30 | 265 |
| 39 | 1800 | 43.1 | 8.7 | 0.40 | 450 | 32 | 297 |
| 40 | 1800 | 41.0 | 8.0 | 0.38 | 451 | 33 | 322 |
| 41 | 1800 | 40.0 | 7.8 | 0.35 | 451 | 100 | 355 |

Light with a peak wavelength at approximately 450 nm was seen in the porous $Si_3N_4$ of Nos. 36 to 41. The more the $Eu_2O_3$ content increased, the higher was the brightness.

EXAMPLE 14

Figure 32:
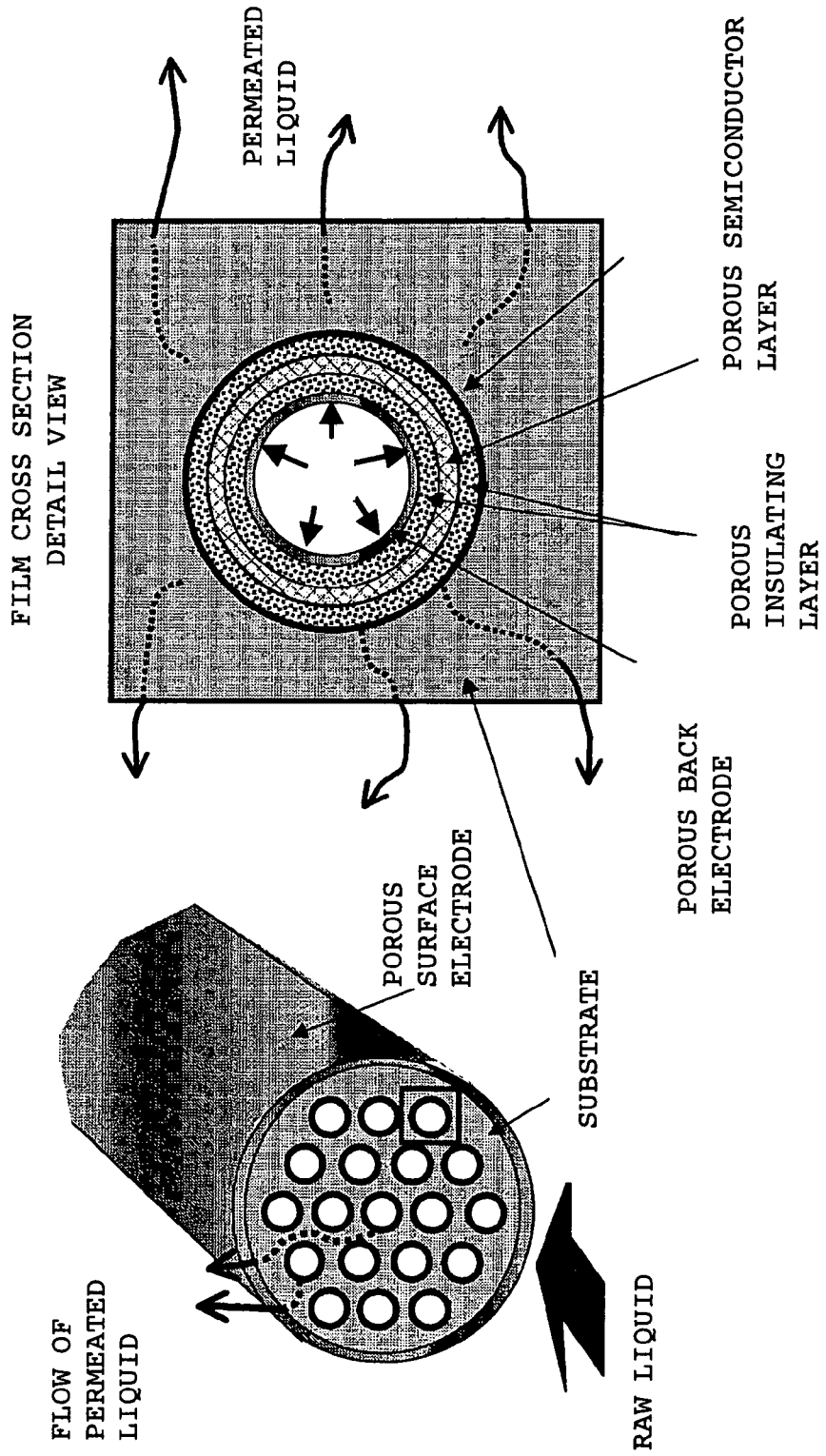
FIG. 32 is a diagram of the basic structure of the monolithic filter manufactured in Example 14.

The monolithic filter shown in FIG. 32 was manufactured in this example. First, as shown on the left in FIG. 32, a ceramic filter substrate was integrally molded from an extrusion mold, in a cylindrical shape with a cross section having circular through-holes (lotus root shape). The right side of the drawing is a detail enlargement of the portion of the cross section within the square on the left side of the drawing. As shown on the right in FIG. 32, a porous back electrode, a porous insulating layer, and a porous semiconductor layer were laminated in that order on the inner walls of the circular through-hole portions. A porous surface electrode was formed over the entire outer surface of the monolith, and the electrode on the inner walls of the passages served as a porous back electrode. This allowed the filter to emit light by electroluminescence. Also, an insulating layer was formed in this example, but a porous ceramic substrate sometimes functions as a kind of insulating layer, in which case there is no need for the insulating layer between the porous ceramic substrate and the porous semiconductor layer.

A raw filtration liquid was allowed to flow into the filter thus manufactured from the front side in FIG. 32, and the permeated liquid came out from the sides of the filter.

INDUSTRIAL APPLICABILITY

The porous semiconductor of the present invention is a semiconductor with a porous structure having continuous pores, with particular emphasis on a material with a large bandgap. When voltage is applied to this, for example, it emits ultraviolet light or short-wavelength visible light, and also provides the function of selectively trapping particles of a specific size present in a gas or liquid.

A filter produced from the porous semiconductor of the present invention traps organic matter, bacteria, viruses, and so forth on the filter surface or in its interior, and furthermore the trapped material can be irradiated with ultraviolet light extremely close-up, the result being a filter with an extremely compact size with which trapped material can be decomposed or sterilized. Organic matter, bacteria, viruses, and so forth can also be decomposed or sterilized by being irradiated with ultraviolet light while passing through the pores of the filter.

A filter produced from the porous semiconductor of the present invention can be used in a wide range of fields, such as decomposing and removing NOx, SOx, CO gas, diesel particulates, pollen, dust, mites, and other contaminants from the air, decomposing and removing organic compounds contained in sewage, sterilization light sources for common bacteria, viruses, and so forth, decomposing harmful gases generated by chemical plants, decomposing malodorous components, illumination-use ultraviolet light sources, photocatalyst light sources, and sterilization light sources used in ultrapure water manufacturing apparatus.

As for product types, the present invention can be utilized in all filters used in the above-mentioned fields, with possible applications including honeycomb structures used for treating automotive exhaust gases, filters for purifying air, sewage filters, gas separation filters, various kinds of water purifiers, insect repellants, large-surface area light emitting glass or walls, and catalyst supports used in hydrogen generation.

Further, ultraviolet light is effective in the cultivation of reptiles, so the present invention is also effective as an ultraviolet light source in the raising of reptiles. If any of various fluorescent materials having a property of emitting light under ultraviolet irradiation is disposed on the surface of the porous semiconductor device of the present invention, then visible light can be generated from the fluorescent material excited by the emitted ultraviolet light, affording a light emitting device that emits both ultraviolet and visible light.

Ultraviolet light is also necessary in the production of vitamin D, and the pores of the porous semiconductor can serve as a hotbed for the efficient synthesis of vitamin D, meaning that the present invention can also be used effectively as a bioreactor.

Finally, the porous semiconductor of the present invention can be used as a light emitting device or filter that affords easy pore control, has high strength, and has high permeation performance. Its function of emitting ultraviolet light is particularly excellent when it contains gadolinium.

The invention claimed is:

1. A method for manufacturing a porous semiconductor device having a light emitting function and comprising a porous substrate having through-holes, and a porous semiconductor layer formed on a surface of this substrate, the method comprising at least steps of:
    (a) preparing a porous substrate and at least one of semiconductor particles having a light emitting function that works by electroluminescence, cathode luminescence, or photoluminescence;
    (b) producing a suspension of the semiconductor particles; and
    (c) filtering the suspension through the porous substrate, thereby forming a deposited layer comprising semiconductor particles on the surface of the porous substrate.

2. A method for manufacturing a porous semiconductor device according to claim 1, further comprising a step of forming an electrode for injecting current into the deposited layer.

3. A method for manufacturing a porous semiconductor device according to claim 1, further comprising a step of performing a treatment for bonding together the individual semiconductor particles that form the deposited layer, after the step (c).

4. A method for manufacturing a porous semiconductor device according to claim 3, wherein the treatment is a heat treatment.

5. A method for manufacturing a porous semiconductor device according to claim 3, wherein the treatment is a treatment in which a semiconductor material is deposited in the vapor phase at the contact portions between the semiconductor particles.

6. A method for manufacturing a porous semiconductor device according to claim 1, comprising a step of coating a surface of the semiconductor particles with an insulating layer or a material having a photocatalytic function, between the steps (a) and (b).

7. A method for manufacturing a porous semiconductor device according to claim 1, wherein a step of coating a porous substrate surface with an insulating layer is added before the step (c), and a step of coating the surface of the deposited layer with an insulating layer is added after the step (c).

8. A method for manufacturing a porous semiconductor device according to claim 1, wherein in the step (b), at least one of suspension of p-type semiconductor particles and at least one of suspension of n-type semiconductor particles are prepared, and in the step (c), these suspensions are alternately filtered through the porous substrate to form a deposited layer with a pn junction structure.

9. A method for manufacturing a porous semiconductor device according to claim 1, wherein an average size of the semiconductor particles is from 0.01 to 5 µm.

10. A porous semiconductor device for filtering, sterilizing and decomposing organic matter, the porous semiconductor device comprising:
a porous substrate having continuous pores; and
a porous semiconductor layer having a light emitting property by electroluminescence, cathode luminescence, or photoluminescence, and having continuous pores,
wherein an electrode is formed on atop or bottom surface of the porous substrate, a porous insulating layer, a porous semiconductor layer, another porous insulating layer, and another electrode are formed sequentially on the porous substrate, the porous semiconductor layer emits ultraviolet light by electroluminescence when AC voltage is applied between the electrodes, and the porous semiconductor layer has a bandgap of at least 3.2 eV and is doped with gadolinium, which is the light emitting center, and
the porous semiconductor layer comprises a material selected from a group consisting of GaN, AlN, ZnO, $ZnF_2$, and diamond.

11. A porous semiconductor device for filtering, sterilizing and decomposing organic matter, the porous semiconductor device comprising:
a porous substrate having continuous pores; and
a porous semiconductor layer having a light emitting function that works by electroluminescence, cathode luminescence, or photoluminescence, and having continuous pores;
wherein an electrode is formed on a top or bottom surface of the porous substrate, the porous semiconductor layer is formed by dispersing semiconductor particles in an insulating layer, an electrode is formed on the porous semiconductor layer, the porous semiconductor layer emits ultraviolet light by electroluminescence when AC voltage is applied between the electrodes, and the semiconductor particles have a bandgap of at least 3.2 eV and are doped with gadolinium. which is the light emitting center.

12. A porous semiconductor device according to claim 10 or 11, wherein a surface of the porous insulating layer or of the porous semiconductor layer formed by dispersing semiconductor particles in the insulating layer is covered by a porous layer having a photocatalytic function, or pore walls of the porous substrate are covered by a material having a photocatalytic function.

13. A porous semiconductor device according to claim 10 or 11, wherein the porous insulating layer or the insulating layer in which the semiconductor particles are dispersed is formed from a material having a photocatalytic function.

14. A porous semiconductor device according to claim 10 or 11, wherein the bandgap of the porous semiconductor layer or the semiconductor particles is at least 4.0 eV.

15. A porous semiconductor device according to claim 10 or 11, wherein either the electrodes are porous or the structure of the electrodes has a porous structure.

16. A porous semiconductor device according to claim 15, wherein the electrodes comprises a porous transparent electroconductive film.

17. A method for manufacturing a porous semiconductor device in which a porous insulating layer, a porous semiconductor layer, and a porous insulating layer are laminated on a porous substrate having continuous pores and having an electrode formed on its top or bottom surface, and another electrode is formed on the top surface, the porous semiconductor device emitting ultraviolet light by electroluminescence when AC voltage is applied between the electrodes, the method comprising at least steps of:

(a) preparing a suspension of gadolinium-doped semiconductor powder and a suspension of a insulator powder;
(b) filtering the suspension of a insulator powder through the porous substrate to deposit a porous insulating layer on the porous substrate surface;
(c) filtering the suspension of the semiconductor powder through the porous substrate to deposit a porous semiconductor layer on the insulating layer; and
(d) further filtering the suspension of the insulator powder through the porous substrate to deposit a porous insulating layer on the semiconductor layer.

18. A method for manufacturing a porous semiconductor device in which a porous semiconductor layer comprising semiconductor particles dispersed in an insulating layer is formed on a porous substrate having continuous pores and having an electrode formed on its top or bottom surface, and another electrode is formed on the top surface, the porous semiconductor device emitting ultraviolet light by electroluminescence when AC voltage is applied between the electrodes, the method comprising at least steps of:

(a) preparing a gadolinium-doped semiconductor powder;
(b) covering the semiconductor powder with an insulating layer and preparing another suspension thereof; and
(c) filtering the suspension through the porous substrate to deposit a porous semiconductor layer on the porous substrate.

19. A filter composed of the porous semiconductor device according to claim 10 or 11.

20. A bioreactor composed of the porous semiconductor device according to claim 10 or 11.

21. An ultraviolet light source that makes use of the porous semiconductor device according to claim 10 or 11.

22. A porous semiconductor device for filtering, sterilizing and decomposing organic matter, the porous semiconductor device comprising:
a porous substrate having continuous pores; and
a porous semiconductor layer having a light emitting function that works by electroluminescence, cathode luminescence, or photoluminescence, and having continuous pores,
wherein the porous semiconductor layer is made of porous silicon nitride comprising columnar $Si_3N_4$ particles wit an average aspect ratio of at least 3 and an oxide-based binder phase containing at least one of rare earth element, and emits visible light or ultraviolet light.

23. A porous semiconductor device according to claim 22, wherein a surface of the columnar $Si_3N_4$ particles is covered with a film or particles having a photocatalytic function.

24. A porous semiconductor device according to claim 22, wherein a film or deposited layer of particles having a photocatalytic function is formed on a surface of the porous semiconductor layer.

25. A porous semiconductor device according to claim 22, which emits ultraviolet light having its peak wavelength in a range of at 300 to 320 nm.

26. A porous semiconductor device according to claim 22, containing at least gadolinium as the rare earth element.

27. A porous semiconductor device according to claim 26, further containing yttrium as the rare earth element.

28. A porous semiconductor device according to claim 22, wherein an average pore size of the porous semiconductor layer is from 0.1 to 5 µm.

29. A porous semiconductor device according to claim 22, wherein a three-point bending strength is at least 100 MPa.

30. A light emitting device having the porous semiconductor device according to claim 22.

31. A filter that makes use of the porous semiconductor device according to claim 22.

32. A porous semiconductor device for filtering, sterilizing and decomposing organic matter, the porous semiconductor device comprising:
  a porous substrate having continuous pores; and
  a porous semiconductor layer having a light emitting function that works by electroluminescence, cathode luminescence, or photo luminescence, and having continuous pores,
  wherein the porous substrate is columnar in shape and has formed therein in an axial direction a plurality of holes serving as passages for a fluid to be treated, the continuous pores lead from an inner wall of the holes to a side of the column, and the porous semiconductor layer is formed on the inner wall.

* * * * *